(12) United States Patent
De La Rosa et al.

(10) Patent No.: US 8,372,807 B2
(45) Date of Patent: Feb. 12, 2013

(54) METHODS OF MODULATING URIC ACID LEVELS

(75) Inventors: Martha De La Rosa, Durham, NC (US); Jean-Luc Girardet, San Diego, CA (US); Karen Watson, Encinitas, CA (US)

(73) Assignee: Ardea Biosciences, Inc., San Diego, CA (US)

( * ) Notice: Subject to any disclaimer, the term of this patent is extended or adjusted under 35 U.S.C. 154(b) by 0 days.

(21) Appl. No.: 13/321,158

(22) PCT Filed: May 20, 2010

(86) PCT No.: PCT/US2010/035580
§ 371 (c)(1),
(2), (4) Date: Jan. 27, 2012

(87) PCT Pub. No.: WO2010/135536
PCT Pub. Date: Nov. 25, 2010

(65) Prior Publication Data
US 2012/0135929 A1  May 31, 2012

Related U.S. Application Data

(60) Provisional application No. 61/180,100, filed on May 20, 2009.

(51) Int. Cl.
| | | |
|---|---|---|
| A61K 38/85 | (2006.01) | |
| A61K 31/56 | (2006.01) | |
| A61K 31/497 | (2006.01) | |
| A61K 31/522 | (2006.01) | |
| A61K 31/44 | (2006.01) | |
| A61K 31/41 | (2006.01) | |
| A61K 31/425 | (2006.01) | |
| A61K 31/415 | (2006.01) | |

(52) U.S. Cl. ............ 514/10.8; 514/171; 514/254.05; 514/263.3; 514/340; 514/359; 514/369; 514/398; 514/407

(58) Field of Classification Search ............ 514/10.8, 514/171, 254.05, 263.3, 340, 359, 361, 365, 514/369, 398, 407
See application file for complete search history.

(56) References Cited

U.S. PATENT DOCUMENTS

| | | | |
|---|---|---|---|
| 4,198,513 | A | 4/1980 | Baldwin et al. |
| 5,939,462 | A | 8/1999 | Connell et al. |
| 6,245,817 | B1 | 6/2001 | Connell et al. |
| 7,435,752 | B2 | 10/2008 | Girardet et al. |
| 7,642,277 | B2 | 1/2010 | Simoneau et al. |
| 7,683,087 | B2 | 3/2010 | Girardet et al. |
| 7,947,721 | B2 | 5/2011 | Girardet et al. |
| 8,003,681 | B2 | 8/2011 | Girardet et al. |
| 8,084,483 | B2 | 12/2011 | Quart et al. |
| 8,106,205 | B2 | 1/2012 | Girardet et al. |
| 2005/0054639 | A1 | 3/2005 | Simoneau et al. |
| 2006/0135556 | A1 | 6/2006 | Girardet et al. |
| 2006/0270725 | A1 | 11/2006 | Girardet et al. |
| 2008/0027048 | A1 | 1/2008 | Miyata et al. |
| 2008/0176850 | A1 | 7/2008 | Girardet et al. |
| 2008/0249131 | A1 | 10/2008 | Girardet et al. |
| 2008/0319201 | A1 | 12/2008 | Girardet et al. |
| 2009/0197825 | A1 | 8/2009 | Quart et al. |
| 2010/0056464 | A1 | 3/2010 | Gunic et al. |
| 2010/0056465 | A1 | 3/2010 | Gunic et al. |
| 2010/0056542 | A1 | 3/2010 | Gunic et al. |
| 2010/0056593 | A1 | 3/2010 | Gunic et al. |
| 2010/0069645 | A1 | 3/2010 | Girardet et al. |
| 2010/0081827 | A1 | 4/2010 | Girardet et al. |
| 2010/0137590 | A1 | 6/2010 | Girardet et al. |
| 2010/0267724 | A2 | 10/2010 | Girardet et al. |
| 2011/0190491 | A1 | 8/2011 | Girardet et al. |
| 2011/0268801 | A1 | 11/2011 | Girardet et al. |
| 2011/0293719 | A1 | 12/2011 | Girardet et al. |
| 2011/0313157 | A1 | 12/2011 | Girardet et al. |
| 2012/0077981 | A1 | 3/2012 | Girardet et al. |

FOREIGN PATENT DOCUMENTS

| | | |
|---|---|---|
| CA | 1050531 | 3/1979 |
| JP | 7215940 | 8/1995 |
| WO | WO-2004-030611 | 4/2004 |
| WO | WO-2004-050643 | 6/2004 |
| WO | WO-2005-087750 | 9/2005 |
| WO | WO-2005-118575 | 12/2005 |
| WO | WO-2006-026356 | 3/2006 |
| WO | WO-2007-050087 | 5/2007 |
| WO | WO-2007-139951 | 12/2007 |
| WO | WO-2007-140002 | 12/2007 |
| WO | WO-2008-057246 | 5/2008 |
| WO | WO 2008/118626 | 10/2008 |
| WO | WO-2009-070740 | 6/2009 |

OTHER PUBLICATIONS

Anzai et al., :The Multivalent PDZ Domain-containing Protein PDZK1 Regulates Transport Activity of Renal Urate-Anion Exchanger URAT1 via Its C Terminus, J. Biol. Chem. 279:45942-45950 (2004).

Chen et al., "Synthesis and Antibacterial Action of 3-(5-(3-Pyridyl)-2H-Tetrazol-2-yl-methyl)-4-Aryl-1,2,4-Triazol-5-Alkysulfide," Chinese Journal of Applied Chemistry, (1990), vol. 7, No. 5, pp. 27-33.

De La Rosa et al., "Tri-substituted triazoles as potent non-nucleoside inhibitors of the HIV-1 reverse transcriptase," Bioorg. Med. Chem. Lett. 16:4444-4449.

Enomoto et al., "Molecular identification of a renal urate-anion exchanger that regulates blood urate levels," Nature 417:447-452 (2002).

(Continued)

Primary Examiner — Raymond Henley, III
(74) Attorney, Agent, or Firm — Wilson, Sonsini, Goodrich & Rosati

(57) ABSTRACT

Described herein are compounds useful in the reduction of blood uric acid levels, formulations containing them and methods of making and using them. In some embodiments, a compound disclosed herein are used in the treatment or prevention of disorders related to aberrant levels of uric acid.

15 Claims, No Drawings

OTHER PUBLICATIONS

Fleishmann, R., et al. "Lesinurad (RDEA594), A Novel Uricosuric Agent, in Combination with Febuxostat Shows Significant Additive Urate Lowering Effects . . . " (May 25-28, 2011).

Gagnon et al. "Investigation on the role of the tetrazole in the binding of thiotetrazolylacetanilides with HIV-1 wild type and K103N/Y181C double mutant reverse transcriptases", Bioorganic & Medicinal Chemistry Letters (2009), 19(4), 1199-1205.

Girardet et al., "The discovery of RDEA806, a potent new HIV NNFTI in phase 1 clinical trials," Poster at 47th Annual Interscience Conference on Antimicrobial Agents and Chemotherapy (ICAAC), Chicago, IL, Sep. 17-20, 2007.

Hamatake et al., "An IQ assessment of RDEA806, a potent NNRTI with an execllent activity profile in the presence of human serum proteins," Poster at 15th Conference on Retroviruses and Opportunistic Infections (CROU), Boston, MA, Feb. 3-6, 2008.

Hamatake et al., "RDEA806, a potent NNRTI with a high genetic barrier to resistance," Poster at 47th Annual Interscience Conference on Antimicrobial Agents and Chemotherapy (ICAAC), Chicago, IL, Sep. 17-20, 2007.

Kerr, B., et al. "Pharmacokinetics and Serum Urate Lowering Effect of RDEA594, A Novel URAT1 Inhibitor, In Gout Patients and Subjects with Varying . . . " (Mar. 2-5, 2011).

Lasko, B., et al. "RDEA594, a Novel Uricosuric Agent, Significantly Reduced Serum Urate Levels and Was Well Tolerated in a Phase 2a Pilot Study in . . . " (Oct. 16-21, 2009).

Ludovici et al., "Evolution of anti-Hiv candidates. Part 3. Diarylpyrimidine (DAPY) analogues," Bioorg. Med. Chem. Lett. 11(17):2235-2239 (2001).

Modi et al., "Synthesis of substituted 1,2 arylhydrazones of 4-aryl-4H-1,2,4-triazolyl-3-thioacetic acid hydrazides," J. Indian Chem. Soc. 54:1087-1089 (1977).

Perez-Ruiz, F., et al. "Efficacy and Safety of RDEA594, a Novel Uricosuric Agent, as Combination Therapy with Allopurinol in Gout Patients: Randomized, . . . " (Jun. 16-19, 2010).

Shen, Z., et al. "A RDEA594, A Novel Uricosuric Agent, Shows Significant Additive Activity in Combination with Allopurinol in Gout Patients" (Mar. 2-5, 2011).

Soliman et al., "Synthesis of some substituted mercaptotriazoles with possible anticonvulsant and monoamine oxidase inhibiting activities," Bull. Fax. Pharm. Cairo Univ. 28(2):53-57 (1990).

Tan, P.K., et al. "Lesinurad (RDEA594), A Investigational Uricosuric Agent for Hyperuricemia and Gout, Blocks OAT4 Transport, Mechanism of . . . " (May 25-28, 2011).

Tantawy, et al. Development of some triazole and oxadiazole derivatives as potential CNS depressant agents, Alexandria Journal of Pharmaceutical Sciences (1988), 2(1), 50-3. (CAS Accession No. 1989:407302).

Wang et al., "Synthesis and Biological evaluations of sulfanyltriazoles as novel HIV-1 non-nucleoside reverse transcriptase inhibitors, " Bioorganic & Medicinal Chemistry Letter, (2006), 16, 4174-4177.

Xu, W., et al. "Resistance to RDEA806 Requires Multiple Mutations Which Have Limited Cross-Resistance to Other NNRTI's" (Oct. 25-28, 2008).

Yang, X., et al. "Evaluation of Drug-Drug Interaction Potential Between RDEA594, Allopurinol and Febuxostat in Preclinical Species" (Oct. 16-21, 2009).

Yeh et al., "RDEA806, a potent non-nucleoside reverse transcriptase inhibitor with less potential for drug-drug interactions," Poster at 47th Annual Interscience Conference on Antimicrobial Agents and Chemotherapy (ICAAC), Chicago, IL, Sep. 17-20, 2007.

Yeh et al., "Safety and pharmacokinetics of ascending single oral doses of RDE806, a novel HIV non-nucleoside reverse transcriptase inhibitor, in healthy volunteers," Poster at 47th Annual Interscience Conference on Antimicrobial Agents and Chemotherapy (ICAAC), Chicago, IL, Sep. 17-20, 2007.

Yeh, L., et al. "RDEA594, a Novel Uricosuric Agent, Shows Impressive Reductions in Serum Urate Levels as a Monotherapy and Substantial Additive Activity . . . " (Jun. 16-19, 2010).

Yeh, L., et al. "RDEA594, a Potential Uric Acid Lowering Agent through Inhibition of Uric Acid Reuptake, Shows Better Pharmacokinetics than its . . . " (Oct. 24-29, 2008).

Yeh, L., et al. "A Novel URAT1 Inhibitor, Shows Significant Additive Urate Lowering Effects in Combination with Febuxostat in Both Healthy Subjects and . . . " (Mar. 2-5, 2011).

Yeh, L.T., et al. "Mode of Action of RDEA594 as a Uric Acid Lowering Agent in Humans Following Multiple Doses of its Prodrug, RDEA806" (Jun. 11-14, 2008).

Yeh, L.T., et al. "Safety, Pharmacokinetics, and Serum Uric Acid Lowering Effect of RDEA594, A Novel, Uricosuric Agent, in Healthy Volunteers" (Jun. 10-13, 2009).

Yeh, L-T., et al. "RDEA594:A Potent URAT1 Inhibitor Without Affecting Other Important Renal Transporters, OAT1 and OAT3" (Jun. 10-13, 2009).

Yeh, L-T., etal "Safety and Uric Acid Lowering Effect in Humans Following Multiple Doses of RDEA806, a Novel Prodrug for the Potential Treatment of . . . " (Jun. 11-14, 2008).

Zhang, Z. et al., "A Novel Nonnucleoside Analogue That Inhibits Human Immunodeficiency Virus Type I Isolates Resistant to Current Nonnucleoside Reverse Transcriptase Inhibitors," Antimicrobial Agents and Chemotherapy 51(2):429-437 (2007).

PCT/US10/35573 Search Report dated Mar. 28, 2011.

PCT/US10/35580 Search Report dated Feb. 21, 2011.

Walker et al., "High serum urate in HIV infected persons: the choice of the antiretroviral matters," AIDS, vol. 20, pp. 1556-1557 (2006).

METHODS OF MODULATING URIC ACID LEVELS

CROSS-REFERENCE

This application is filed pursuant to 35 U.S.C. §371 as a United States National Phase Application of International Application Ser. No. PCT/US 10/035,580, filed May 20, 2010, which claims the benefit of U.S. Provisional Application No. 61/180,100, filed May 20, 2009, both of which are incorporated by reference herein in their entirety.

BACKGROUND OF THE INVENTION

Aberrant uric acid levels are related to several disorders including, but not limited to, gout, gouty arthritis, inflammatory arthritis, kidney disease, nephrolithiasis (kidney stones), joint inflammation, deposition of urate crystals in joints, urolithiasis (formation of calculus in the urinary tract), deposition of urate crystals in renal parenchyma, Lesch-Nyhan syndrome, and Kelley-Seegmiller syndrome.

SUMMARY OF THE INVENTION

Provided herein in some embodiments are methods for decreasing uric acid levels in one or more tissues or organs of a subject, comprising administering to the subject a uric acid level decreasing amount of a compound of Formula (I):

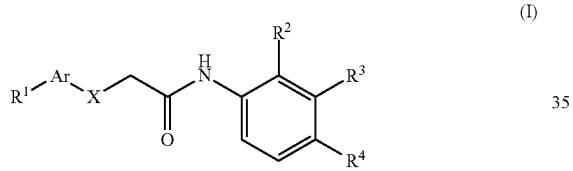

wherein:
Ar is a 5-membered aromatic heterocycle containing 1 to 4 heteroatoms each independently selected from N, O and S; said heterocycle being optionally substituted at a substitutable position with $R^{Ar}$, wherein $R^{Ar}$ is H, $(C_{1-4})$alkyl, $CF_3$ or $(C_{3-7})$cycloalkyl and wherein the groups X and $R^1$ are attached to positions on the Ar ring which are immediately adjacent to each other;
X is selected from O and S;
$R^1$ is a group of Formula:

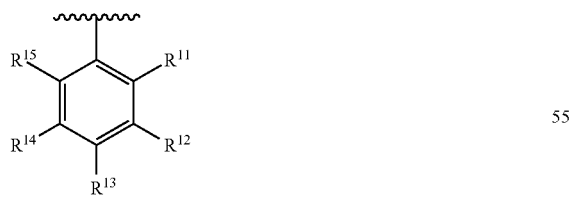

wherein $R^{11}$ is halo; and $R^{12}$, $R^{13}$, $R^{14}$ and $R^{15}$ are each independently selected from H, halo, $(C_{1-4})$alkyl, $CF_3$, $(C_{3-7})$cycloalkyl, $(C_{3-7})$cycloalkyl-$(C_{1-4})$alkyl-, cyano, —O—$(C_{1-4})$alkyl, —$OCF_3$ and —$N((C_{1-4})$alkyl$)_2$, wherein said $(C_{3-7})$cycloalkyl is optionally substituted with $(C_{1-4})$alkyl; or $R^{12}$ and $R^{13}$, $R^{13}$ and $R^{14}$, or $R^{14}$ and $R^{15}$ are linked, together with the carbon atoms to which they are attached, to form a five- or six-membered saturated, unsaturated or aromatic ring which optionally contains from one to three heteroatoms each independently selected from O, S and N, wherein the remaining of $R^{12}$, $R^{13}$, $R^{14}$ and $R^{15}$ are defined as hereinbefore;
$R^2$ is selected from halo, nitro and $(C_{1-4})$alkyl;
$R^3$ is selected from H and halo;
$R^4$ is selected from:
(A)

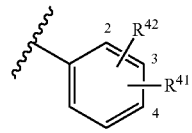

wherein $R^{42}$ is bonded to position 2 or position 3 of the phenyl ring and is selected from H, halo and $(C_{1-4})$alkyl; and $R^{41}$ is bonded to position 3 or position 4 of the phenyl ring and is selected from:
  i) $(C_{1-4})$alkyl substituted with —COOH, —COO$(C_{1-4})$alkyl, —C(=O)$NH_2$, —C(=O)$NHSO_2$—$(C_{1-4})$alkyl, or —OH;
  ii) $(C_{2-4})$alkenyl substituted with —COOH or —COO$(C_{1-4})$alkyl;
  iii) —O—$(C_{1-4})$alkyl optionally substituted with —COOH, Het, or —N$((C_{1-6})$alkyl$)_2$, wherein said Het is optionally substituted with —OH or —COOH and wherein either or both of the $(C_{1-6})$alkyl groups in said —N$((C_{1-6})$alkyl$)_2$ are optionally substituted with —COOH or —COO$(C_{1-4})$alkyl; and
  iv) —OH, —COOH, —COO$(C_{1-4})$alkyl, —$SO_2NH_2$, or —$SO_2$—$(C_{1-4})$alkyl;
  provided that $R^{42}$ and $R^{41}$ is not both be bonded to position 3 of the phenyl ring at the same time;
(B) $(C_{2-4})$alkenyl substituted with —COOH or —COO$(C_{1-4})$alkyl;
(C) Het optionally substituted with $(C_{1-6})$alkyl, —$NH_2$, —COOH, or $(C_{2-4})$alkenyl substituted with —COOH;
(D) —$SO_2N(R^{43})R^{44}$, wherein $R^{43}$ is H or $(C_{1-6})$alkyl and $R^{44}$ is selected from $(C_{1-6})$alkyl, phenyl, phenyl-$(C_{1-4})$alkyl-, —C(=O)NH$(C_{1-4})$alkyl, —C(=O)O$(C_{1-4})$alkyl, and Het; wherein said $(C_{1-6})$alkyl is optionally substituted with —OH or —COOH and wherein said Het is optionally substituted with $(C_{1-6})$alkyl; or $R^{43}$ and $R^{44}$, together with the N to which they are attached, are linked together to form a 5- or 6-membered heterocycle which is saturated or unsaturated and which is optionally contain from one to three further heteroatoms each independently selected from N, O and S; said heterocycle being optionally substituted with $(C_{1-6})$alkyl or —COOH;
(E) —O—$(C_{1-4})$alkyl substituted with —OH, —COOH or Het, wherein said Het is optionally substituted with —COOH or —COO$(C_{1-6})$alkyl; provided that the carbon atom of —O—$(C_{1-4})$alkyl which is directly bonded to 0 is not also directly bonded to —OH;
(F) —C(=O)N$(R^5)R^6$ or —O—$CH_2$—C(=O)N$(R^5)R^6$ wherein $R^5$ is H or $(C_{1-6})$alkyl and $R^6$ is selected from:
  i) phenyl optionally substituted with one or two substituents each independently selected from —OH, —COOH, —N$((C_{1-4})$alkyl$)_2$, $(C_{1-4})$alkyl, $(C_{2-4})$alkenyl and Het; wherein said $(C_{1-4})$alkyl is optionally substituted with —COOH and said $(C_{2-4})$alkenyl is substituted with —COOH;
ii) $(C_{1-4})$alkyl optionally substituted with one or two substituents each independently selected from —COOH, —OH, —S—$(C_{1-6})$alkyl and Het; provided that the carbon atom of $(C_{1-4})$alkyl which is directly bonded to N is not also directly bonded to —OH;
iii) phenyl-$(C_{1-4})$alkyl- wherein the phenyl portion of said phenyl-$(C_{1-4})$alkyl- is optionally substituted with one or two substituents each independently selected from —OH, —NH$_2$, and —COOH;
iv) $(C_{3-7})$cycloalkyl-$(C_{1-4})$alkyl- wherein the cycloalkyl portion of said $(C_{3-7})$cycloalkyl-$(C_{1-4})$alkyl- is optionally substituted with —COOH;
v) Het optionally substituted with one or two substituents each independently selected from $(C_{1-6})$alkyl, phenyl-$(C_{1-4})$alkyl- and —COOH;
vi) $(C_{3-7})$cycloalkyl; and
vii) —SO$_2$—R$^{61}$ wherein R$^{61}$ is $(C_{1-4})$alkyl or phenyl; or
R$^5$ and R$^6$, together with the N to which they are attached, are linked together to form a 5- or 6-membered heterocycle which is saturated or unsaturated and which is optionally contain from one to three further heteroatoms each independently selected from N, O and S; said heterocycle being optionally substituted with one or two substituents each independently selected from $(C_{1-6})$alkyl, —COOH and —COO$(C_{1-6})$alkyl;
(G) —NHC(=O)—R$^7$ wherein R$^7$ is selected from:
i) $(C_{1-6})$alkyl optionally substituted with one or two substituents each independently selected from —COOH, —O—$(C_{1-4})$alkyl, —NHC(=O)—$(C_{1-4})$alkyl, phenyl and Het; wherein said phenyl is optionally substituted with one or two substituents each independently selected from halo, —OH, —O—$(C_{1-4})$alkyl, —NO$_2$, —COOH, —NH$_2$, —NH$(C_{1-4})$alkyl, —N$((C_{1-4})$alkyl$)_2$, and $(C_{1-6})$alkyl optionally substituted with from one to three halo substituents;
ii) phenyl optionally substituted with —OH, halo or —COOH;
iii) —NHR$^{71}$ wherein R$^{71}$ is phenyl or phenyl-$(C_{1-4})$alkyl-, wherein said phenyl is optionally substituted with —COOH or —COO$(C_{1-4})$alkyl; and iv) $(C_{1-6})$alkynyl, $(C_{3-7})$cycloalkyl or $(C_{3-7})$cycloalkyl-$(C_{1-4})$alkyl-;
(H) —NHSO$_2$R$^8$ wherein R$^8$ is selected from phenyl, phenyl-$(C_{1-4})$alkyl- and Het; and
(I) —C≡C—R$^9$ wherein R$^9$ is selected from:
i) H, —COOH, —COO$(C_{1-6})$alkyl, phenyl or $(C_{2-4})$alkenyl;
ii) $(C_{3-7})$cycloalkyl optionally substituted with —OH, —COOH, —COO$(C_{1-6})$alkyl, or $(C_{1-4})$alkyl wherein said $(C_{1-4})$alkyl is optionally substituted with —OH or —N(R$^{91}$)R$^{92}$, wherein R$^{91}$ is H and R$^{92}$ is $(C_{1-4})$alkyl substituted with Het; or R$^{91}$ and R$^{92}$, together with the N to which they are attached, are linked together to form a 5- or 6-membered heterocycle which is saturated, unsaturated or aromatic and which is optionally contain from one to three further heteroatoms each independently selected from N, O and S; said heterocycle being optionally substituted with one or two substituents each independently selected from $(C_{1-6})$alkyl and —OH; and
iii) $(C_{1-6})$alkyl optionally substituted with one, two or three substituents each independently selected from:
a) —OH, —O(C=O)NH$_2$, —O(C=O)NH$(C_{1-4})$alkyl, CF$_3$, —COOH or —COO—$(C_{1-4})$alkyl;
b) Het optionally substituted with $(C_{1-6})$alkyl or —OH;
c) —N(R$^{93}$)R$^{94}$ wherein R$^{93}$ is H or $(C_{1-4})$alkyl and R$^{94}$ is selected from H, —$(C_{1-4})$alkyl optionally substituted with R$^{941}$, —SO$_2$—$(C_{1-4})$alkyl and —C(=O)—R$^{942}$; wherein R$^{941}$ is —COOH, —C(=O)NH$_2$, $(C_{3-7})$cycloalkyl, Het, or phenyl optionally substituted with —OH, and R$^{942}$ is —O—$(C_{1-4})$alkyl, —NH—$(C_{1-4})$alkyl, phenyl, $(C_{3-7})$cycloalkyl or Het, wherein said $(C_{3-7})$cycloalkyl is optionally substituted with —COOH and wherein said Het is optionally substituted with one or two substituents each independently selected from $(C_{1-6})$alkyl and —OH; or R$^{942}$ is $(C_{1-4})$alkyl optionally substituted with —COOH, —NH$_2$, —NH$(C_{1-4})$alkyl, —NH-Het, —N$((C_{1-4})$alkyl$)_2$, or Het; wherein said Het is optionally substituted with one or two substituents each independently selected from —OH, —COOH and $(C_{1-6})$alkyl optionally substituted with Het and wherein the $(C_{1-4})$alkyl portion of said —NH$(C_{1-4})$alkyl is optionally substituted with Het;
d) —C(=O)N(R$^{95}$)R$^{96}$, wherein R$^{95}$ is H and R$^{96}$ is selected from $(C_{3-7})$cycloalkyl, —SO$_2$—R$^{961}$ and —$(C_{1-4})$alkyl-R$^{962}$, wherein R$^{961}$ is $(C_{1-4})$alkyl, phenyl, $(C_{3-7})$cycloalkyl, or —N$((C_{1-4})$alkyl$)_2$; and R$^{962}$ is phenyl, —COOH, —N$((C_{1-4})$alkyl$)_2$, or Het, wherein said phenyl is optionally substituted with —N$((C_{1-4})$alkyl$)_2$ and said Het is optionally substituted with oxo; or R$^{95}$ and R$^{96}$, together with the N to which they are attached, are linked together to form a 5- or 6-membered heterocycle which is saturated or unsaturated and which is optionally contain from one to three further heteroatoms each independently selected from N, O and S; said heterocycle being optionally substituted with —COOH; and
e) —O$(C_{1-4})$alkyl optionally substituted with R$^{97}$ wherein R$^{97}$ is selected from —OH, —COOH, —C(=O)O—(C-4)alkyl-NH$(C_{1-4})$alkyl, —C(=O)N(R$^{97}$)R$^{972}$, —NH$_2$, —NH—$(C_{3-7})$cycloalkyl, —O-Het, and Het;
provided that the carbon atom of —O—$(C_{1-4})$alkyl-which is directly bonded to 0 is not also directly bonded to —OH, —NH$_2$ or —NH—$(C_{3-7})$cycloalkyl;
wherein each of said Het and the Het portion of said —O-Het is optionally substituted with one or two substituents each independently selected from halo, oxo, $(C_{1-4})$alkyl, and —OH;
and wherein R$^{971}$ is H or $(C_{1-4})$alkyl and R$^{972}$ is selected from H, —OH, —NHC(=O)—$(C_{1-4})$alkyl, —NHC(=O)—NH$_2$, $(C_{1-4})$alkyl, $(C_{3-7})$cycloalkyl, phenyl and Het, wherein said $(C_{1-4})$alkyl is optionally substituted with —OH, —COOH, —N$((C_{1-4})$alkyl$)_2$ or Het, provided that when R$^{972}$ is $(C_{1-4})$alkyl, the carbon atom of $(C_{1-4})$alkyl which is directly bonded to N is not also directly bonded to —OH;

and wherein said $(C_{3-7})$cycloalkyl is optionally substituted with —COOH, and wherein said phenyl is optionally substituted with —OH, —COOH, or —$(C_{2-4})$alkenyl-COOH;

or $R^{971}$ and $R^{972}$, together with the N to which they are attached, are linked together to form a 5- or 6-membered heterocycle which is saturated or unsaturated and which is optionally contain from one to three further heteroatoms each independently selected from N, O and S; said heterocycle being optionally substituted with $(C_{1-4})$alkyl or —COOH;

wherein Het is a 4, 5- or 6-membered heterocycle or a 9- or 10-membered heterobicycle, each of which is saturated, unsaturated or aromatic and each of which containing from one to four heteroatoms each independently selected from N, O and S, wherein each said N heteroatom is, independently and where possible, exist in an oxidized state such that it is further bonded to an O atom to form an N-oxide group and wherein each said S heteroatom is, independently and where possible, exist in an oxidized state such that it is further bonded to one or two oxygen atoms to form the groups SO or $SO_2$.

In some embodiments, the compound used in the methods described herein is a metabolite, pharmaceutically acceptable salt, solvate, polymorph, ester, tautomer or prodrug of a compound of Formula I.

Also provided herein in some embodiments, is a method for decreasing uric acid levels in one or more tissues or organs of a subject, comprising administering to the subject a uric acid level decreasing amount of a compound of Formula (II):
$Ar^1$—X'—W—$Ar^2$ (II); wherein $Ar^1$ is:
(i) 5- or 6-membered aromatic heterocycle containing 1 to 4 heteroatoms selected from N, O or sS; said heterocycle optionally substituted with $(C_{1-4})$alkyl, $(C_{3-7})$cycloalkyl, $(C_{3-7})$cycloalkyl-$(C_{1-3})$alkyl-, wherein said alkyl, cycloalkyl or cycloalkylalkyl is monosubstituted with —OH; and/or phenyl when the heterocycle contains 1 to 3 N-atoms; in either instance, the said heterocycle is optionally substituted with: phenyl, phenylmethyl, 5- or 6-membered aromatic heterocycle, fused phenyl-unsaturated or saturated 5- or 6-membered carbocycle, fused phenyl-{unsaturated or saturated 5- or 6-membered carbocycle)}methyl, or fused phenyl-5- or 6-membered aromatic heterocycle; each of said phenyl, phenylmethyl, aromatic heterocycle, fused phenyl-carbocycle, fused phenyl-(carbocycle)methyl or fused phenyl-aromatic heterocycle in turn is substituted optionally with 1 to 3 substituents selected independently from: $(C_{1-6})$alkyl, $(C_{3-7})$cycloalkyl, $(C_{3-7})$cycloalkyl-$(C_{1-3})$alkyl, $(C_{2-6})$alkenyl, O—$(C_{1-4})$alkyl, S—$(C_{1-4})$alkyl, halo, $CF_3$, $OCF_3$, OH, $NO_2$, CN, phenyl optionally substituted with $C_{1-6}$alkyl or nitro, phenylmethyl optionally substituted with $C_{1-6}$alkyl or nitro, $SO_2NH_2$, $SO_2$—$(C_{1-4})$alkyl, $C(O)NH_2$, $C(O)OR^1$, $NR^2R^3$, morpholino or 1-pyrrolyl, wherein $R^1$ is H or $(C_{1-4})$alkyl, and wherein $R^2$ and $R^3$ each independently is H or $(C_{1-4})$alkyl; wherein said substituents are sterically compatible; or
(ii) unsaturated or saturated 5- or 6-membered carbocycle substituted with phenyl or naphthyl, said unsaturated or saturated carbocycle, or the phenyl or naphthyl optionally substituted with the same 1 to 3 substituents as defined for the substituents in section (i); or
(iii) benzimidazole optionally N-substituted with phenyl or a fused phenyl-carbocycle as defined above;

X' is a valence bond, O, S, SO, $SO_2$, $NR^4$ or $CR^{4A}R^{4B}$ wherein $R^4$, $R^{4A}$ and $R^{4B}$ are each independently H or $(C_{1-4})$alkyl; and when X' is O, S, SO, $SO_2$ or $NR^4$: W is a divalent radical selected from:

(A) $(CR^5R^{5A})_{1-2}$—$C(Z^A)NR^6$ wherein $R^5$ and $R^{5A}$ each independently is H or $(C_{1-4})$alkyl, $R^6$ is H or $(C_{1-4})$alkyl, and $Z^A$ is oxo or thioxo;
(B) D-$C(Z^B)$ wherein D is $(C_{1-4})$alkylene, $(C_{1-4})$alkylene-O or $(C_{1-4})$alkylene-$NR^7$ wherein $R^7$ is H or $(C_{1-4})$alkyl, and $Z^B$ is oxo or thioxo;
(C) $CH_2C(Z^C)NR^{7A}(C_{1-4})$alkylene wherein $Z^C$ is oxo or thioxo and $R^{7A}$ is H or $(C_{1-4})$alkyl;
(D) $(C_{1-4})$alkylene-$NR^{7B}C(Z^D)NR^{7C}$ wherein $R^{7B}$ and $R^{7C}$ each independently is H or $(C_{1-4})$alkyl, and $Z^D$ is oxo or thioxo;
(E) $(C_{1-4})$alkylene optionally substituted with OH, or optionally disubstituted with OH when the $(C_{1-4})$ alkylene contains 2 to 4 carbon atoms; $(C_{2-4})$alkenyl optionally substituted with halo; or cis- or trans-

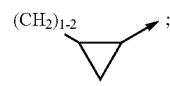

or
(F) {$(C_{1-4})$alkylene}-O optionally substituted on the alkylene portion with OH;
(G) {$(C_{1-4})$alkylene}-$NR^8$ optionally substituted on the alkylene portion with OH, and $R^8$ is H or $(C_{1-4})$alkyl;
(H) $(C_{1-4})$alkylene-$C(Z^E)(C_{1-4})$alkylene wherein $Z^E$ is oxo or thioxo; or
(I)

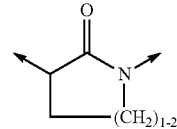

or
(J) $(CR^5R^{5A})_{1-2}$—$NR^6$—$(CR^5R^{5A})_{1-2}$ wherein $R^5$ and $R^{5A}$ each independently is H or $(C_{1-4})$alkyl, $R^6$ is H or $(C_{1-4})$alkyl; and $Ar^2$ is:
(i) a phenyl or pyridinyl selected from the formulas

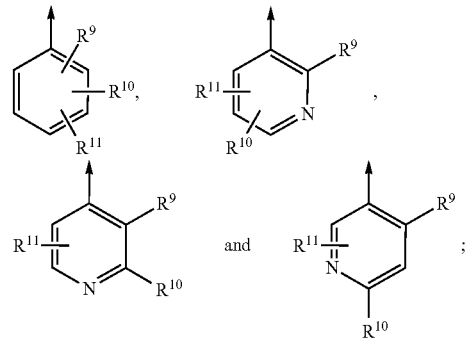

wherein $R^9$, $R^{10}$ and $R^{11}$ each independently represents: H, $(C_{1-6})$alkyl, $(C_{3-7})$cycloalkyl, $(C_{3-7})$cycloalkyl-$(C_{1-3})$alkyl, $(C_{2-6})$alkenyl, O—$(C_{1-6})$alkyl, S—$(C_{1-6})$alkyl, halo, $CF_3$, $OCF_3$, OH, $NO_2$, CN, —$NR^{N1}R^{N2}$, —$C(O)R^{21}$, —$(C_{1-3})$alkyl-$C(O)R^{21}$, —$C(O)OR^{22}$, —$(C_{1-3})$alkyl-$C(O)OR^{22}$, —$SO_2$—$(C_{1-3})$alkyl-$C(O)OR^{22}$, wherein $R^{21}$ is $(C_{1-4})$alkyl; $R^{22}$ is H or $(C_{1-4})$alkyl; $C(O)NH_2$, —$(C_{1-3})$alkyl-$C(O)NH_2$, $S(O)$—$(C_{1-4})$alkyl, $SO_2$—$(C_{1-4})$alkyl, $SO_2NH_2$, phenyl, phenylmethyl, phenyl-$SO_2$—, 2-, 3- or 4-pyridinyl, 1-pyrrolyl, whereby said phenyl, pyridinyl and pyrrolyl have one or more substituents selected from the group consisting of halo, $NO_2$, $C_{1-3}$-alkyl and $CF_3$; wherein the substituents $R^9$, $R^{10}$ and $R^{11}$ are sterically compatible; wherein $R^{N1}$, $R^{N2}$ each independently represent H or $(C_{1-6})$alkyl, whereby $R^{N1}$ and $R^{N2}$ is covalently bonded to each other to form together with the N-atom to which they are attached to a 4 to 7-membered heterocycle whereby the —$CH_2$-group at the position 4 of a 6 or 7-membered heterocycle is replaced by —O—, —S— or —$NR^{N3}$ wherein $R^{N3}$ represents H, —$C(O)OR^{22}$, $(C_{1-6})$alkyl, $(C_{3-7})$cycloalkyl or $(C_{3-7})$cycloalkyl-$(C_{1-3})$alkyl, wherein $R^{22}$ is H or $(C_{1-4})$alkyl; or (ii) $Ar^2$ is a fused phenyl-(saturated or unsaturated 5- or 6-membered carbocyclic ring optionally substituted with 1 to 3 substituents selected independently from $(C_{1-4})$alkyl, O—$(C_{1-4})$alkyl, S—$(C_{1-4})$alkyl, $NO_2$ or halo; or (iii) $Ar^2$ is a 5- or 6-membered aromatic heterocycle containing 1 to 4 heteroatoms selected from N, O or S, or a fused phenyl-5- or 6-membered heterocycle, said aromatic heterocycle or fused phenyl-heterocycle is optionally substituted with 1 to 3 substituents selected independently from $(C_{1-4})$alkyl, O—$(C_{1-4})$alkyl, S—$(C_{1-4})$alkyl, $NO_2$ or halo; or (iv) $Ar^2$ is phthalimido and W is $(C_{1-4})$alkylene.

In some embodiments, X' is a valence bond and W is a $\{(C_{2-4})$alkenyl$\}C(O)NR^{8A}$, cis- or trans-

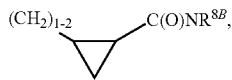

or cis- or trans-

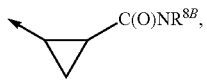

wherein $R^{8A}$ and $R^{8B}$ each is H or $(C_{1-4})$alkyl; or when X' is $CR^{4A}R^{4B}$ as defined above: W is selected from $\{(C_{1-4})$alkylene$\}C(O)NR^{8C}$, S—$\{(C_{1-4})$alkylene$\}C(O)NR^{8D}$, O—$\{(C_{1-4})$-alkylene$\}C(O)NR^{8E}$, or $NR^{8F}$—$\{(C_{1-4})$alkylene$\}$-$NR^{8G}$ wherein $R^{8C}$, $R^{8D}$, $R^{8E}$, $R^{8F}$ and $R^{8G}$ each independently is H or $(C_{1-4})$alkyl.

In some embodiments, the compound used in the methods described herein is a metabolite, pharmaceutically acceptable salt, solvate, polymorph, ester, tautomer or prodrug of a compound of Formula II.

In some specific embodiments, $Ar^1$ is

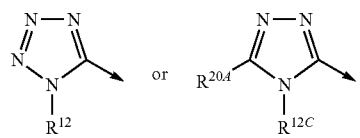

wherein $R^{12}$ is selected from the group consisting of

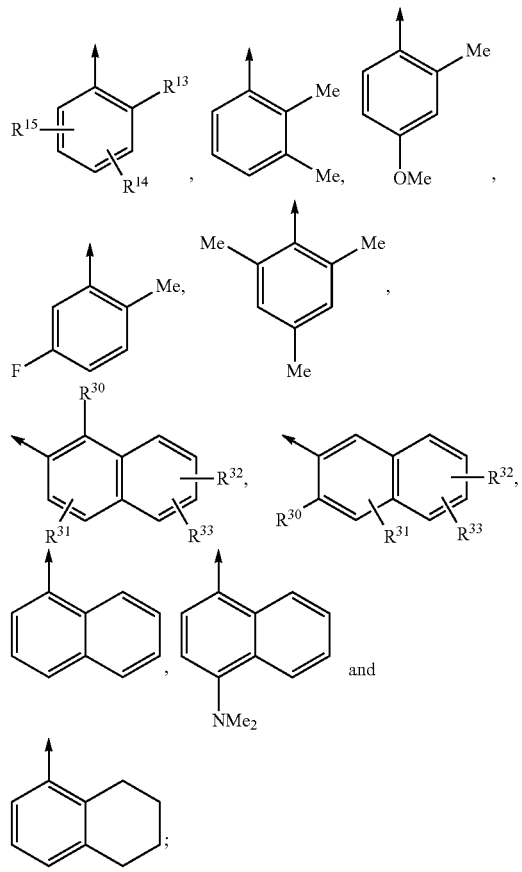

$R^{13}$ represents Cl, Br, $COO(C_{1-4})$alkyl and if $R^9$ is $NO_2$, Cl or Br, then $R^{13}$ also represent F or $CH_3$;

$R^{14}$, $R^{15}$, $R^{31}$, $R^{32}$, $R^{33}$ are each independently selected from the group consisting of H, $(C_{1-6})$alkyl, $(C_{3-7})$cycloalkyl, $(C_{3-7})$cycloalkyl-$(C_{1-3})$alkyl, $(C_{2-6})$alkenyl, O—$(C_{1-4})$alkyl, S—$(C_{1-4})$alkyl, halo, $CF_3$, $OCF_3$, OH, $NO_2$, CN, $SO_2NH_2$, $SO_2$—$(C_{1-4})$alkyl, $C(O)OR^1$ wherein $R^1$ is H or $(C_{1-4})$alkyl, or $NR^2R^3$ wherein $R^2$ and $R^3$ each independently is H or $(C_{1-4})$alkyl;

$R^{30}$ represents H, Cl, Br, $COO(C_{1-4})$alkyl;

$R^{12C}$ is a phenyl of formula

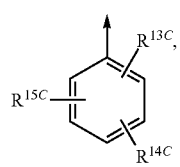

wherein $R^{13C}$, $R^{14C}$ and $R^{15C}$ each independently represents H, $(C_{1-6})$alkyl, $(C_{3-7})$cycloalkyl, $(C_{3-7})$cycloalkyl-$(C_{1-3})$alkyl, $(C_{2-6})$alkenyl, O—$(C_{1-4})$alkyl, S—$(C_{1-4})$alkyl, halo, $CF_3$, $OCF_3$, OH, $NO_2$, CN, $SO_2NH_2$, $SO_2$—$(C_{1-4})$alkyl, $C(O)OR^1$ wherein $R^1$ is H or $(C_{1-4})$alkyl, or $NR^2R^3$ wherein $R^2$ and $R^3$ each independently is H or $(C_{1-4})$alkyl; provided that at least one of $R^{13C}$, $R^{14C}$ and $R^{15C}$ is other than hydrogen;

or $R^{12C}$ is

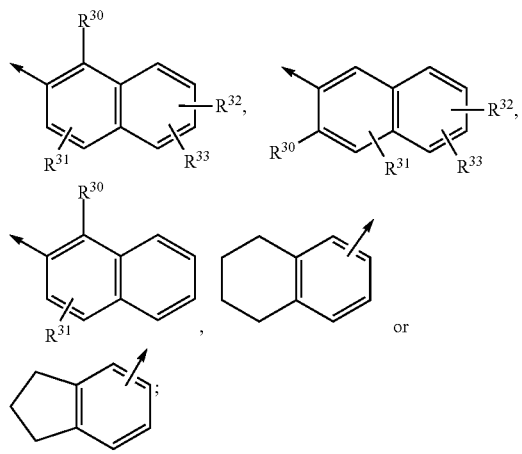

wherein $R^{30}$, $R^{31}$, $R^{32}$, $R^{33}$ are as defined hereinbefore; and $R^{20A}$ is H, $(C_{1-4})$alkyl, $(C_{3-7})$cycloalkyl or $(C_{3-7})$cycloalkyl-$(C_{1-3})$alkyl-, wherein said alkyl, cycloalkyl or cycloalkylalkyl is monosubstituted with —OH.

In other specific embodiments, X' is S or O.

In some specific embodiments, W is $CH_2C(O)NR^6$ wherein $R^6$ is H or $(C_{1-4})$alkyl.

In other specific embodiments, $Ar^2$ is:

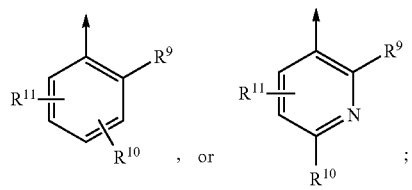

wherein $R^9$ is halo or $NO_2$; and if $R^{13}$ is Cl or Br, then $R^9$ also represents $(C_{1-3})$alkyl; $R^{10}$, $R^{11}$ are independently of each other selected from the group consisting of H, $(C_{1-6})$alkyl, $(C_{3-7})$Cycloalkyl, $(C_{3-7})$Cycloalkyl-$(C_{1-3})$alkyl, $(C_{2-6})$alkenyl, $O(C_{1-6})$alkyl, $S(C_{1-6})$alkyl, halo, $CF_3$, $OCF_3$, OH, $NO_2$, CN, —$NR^{N1}R^{N2}$, —$C(O)R^{21}$, —$(C_{1-3})$alkyl-$C(O)R^{21}$, —$C(O)OR^{22}$, —$(C_{1-3})$alkyl-$C(O)OR^{22}$, —$SO_2$—$(C_{1-3})$alkyl-$C(O)OR^{22}$, wherein $R^{21}$ is $(C_{1-4})$alkyl and $R^{22}$ is H or $(C_{1-4})$alkyl; —$(C_{1-3})$alkyl-$C(O)NH_2$, $C(O)NH_2$, $S(O)$—$(C_{1-6})$alkyl, —$SO_2$—$(C_{1-6})$alkyl, —$SO_2$-phenyl, —$SO_2$—$NH_2$, phenyl, phenylmethyl, 2-, 3- or 4-pyridinyl, 1-pyrrolyl, whereby said phenyl, pyridinyl and pyrrolyl have one or more substituents selected from the group consisting of halo, $NO_2$, $C_{1-3}$-alkyl and $CF_3$.

Also provide herein in various embodiments are method for decreasing uric acid levels in one or more tissues or organs of a subject, comprising administering to the subject a uric acid level decreasing amount of a compound of Formula (III):

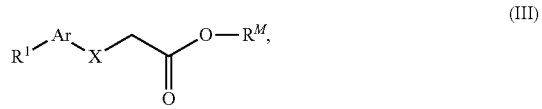

wherein
Ar is a 5-membered aromatic heterocycle containing 1 to 4 heteroatoms each independently selected from N, O and S; said heterocycle being optionally substituted at a substitutable position with $R^{Ar}$; wherein $R^{Ar}$ is H, $(C_{1-4})$alkyl, $CF_3$ or $(C_{3-7})$cycloalkyl, and wherein the groups X and $R^1$ are attached to positions on the Ar ring which are immediately adjacent to each other;

X is O or S;

$R^M$ is H, a pharmaceutically acceptable cation, substituted or unsubstituted $(C_{1-6})$alkyl, substituted or unsubstituted aryl, substituted or unsubstituted heteroaryl, or a prodrug moiety; and $R^1$ is a group of formula:

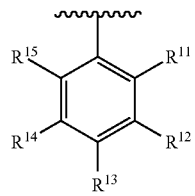

wherein:
$R^{11}$ is F, Cl, Br or I; and
$R^{12}$, $R^{13}$, $R^{14}$ and $R^{15}$ are each independently selected from H, F, Cl, Br, I, CN, $CF_3$, —$OCF_3$, $(C_{1-4})$alkyl, —O—$(C_{1-4})$alkyl, —$N((C_{1-4})$alkyl$)_2$, $(C_{3-7})$cycloalkyl and $(C_{3-7})$cycloalkyl-$(C_{1-4})$alkyl-; wherein said $(C_{3-7})$cycloalkyl is optionally substituted with $(C_{1-4})$alkyl; or $R^{12}$ and $R^{13}$, $R^{13}$ and $R^{14}$, or $R^{14}$ and $R^{15}$ are linked, together with the carbon atoms to which they are attached, to form a five- or six-membered saturated, unsaturated or aromatic ring which optionally contains from one to three heteroatoms each independently selected from O, S and N, wherein the remaining of $R^{12}$, $R^{13}$, $R^{14}$ and $R^{15}$ are defined as hereinbefore.

In some embodiments, the compound used in the methods described herein is a metabolite, pharmaceutically acceptable salt, solvate, polymorph, ester, tautomer or prodrug of a compound of Formula III.

Also provided herein are methods for decreasing uric acid levels in one or more tissues or organs of a subject, comprising administering to the subject a uric acid level decreasing amount of a compound of Formula (IV): $Ar^1$—X'—W—C(O)—O—$R^M$ (IV) wherein:

$R^M$ is H, a pharmaceutically acceptable cation, substituted or unsubstituted $(C_{1-6})$alkyl, substituted or unsubstituted aryl, substituted or unsubstituted heteroaryl, or a prodrug moiety;

$Ar^1$ is:
(i) 5- or 6-membered aromatic heterocycle containing 1 to 4 heteroatoms selected from N, O or S; said heterocycle optionally substituted with $(C_{1-4})$alkyl, $(C_{3-7})$cycloalkyl, $(C_{3-7})$cycloalkyl-$(C_{1-3})$alkyl-, wherein said alkyl, cycloalkyl or cycloalkylalkyl is monosubstituted with —OH; and/or phenyl when the heterocycle contains 1 to 3 N-atoms; in either instance, the said heterocycle is optionally substituted with: phenyl, phenylmethyl, 5- or 6-membered aromatic heterocycle, fused phenyl-unsaturated or saturated 5- or 6-membered carbocycle, fused phenyl-{unsaturated or saturated 5- or 6-membered carbocycle}methyl, or fused phenyl-5- or 6-membered aromatic heterocycle; each of said phenyl, phenylmethyl, aromatic heterocycle, fused phenyl-carbocycle, fused phenyl-(carbocycle)methyl or fused phenyl-aromatic heterocycle in turn is substituted optionally with 1 to 3 substituents selected independently from: $(C_{1-6})$ alkyl, $(C_{3-7})$cycloalkyl, $(C_{3-7})$cycloalkyl-$(C_{1-3})$alkyl, $(C_{2-6})$alkenyl, O—$(C_{1-4})$alkyl, S—$(C_{1-4})$alkyl, halo, $CF_3$, $OCF_3$, OH, $NO_2$, CN, phenyl optionally substituted with $C_{1-6}$alkyl or nitro, phenylmethyl optionally substituted with $C_{1-6}$alkyl or nitro, $SO_2NH_2$, $SO_2$—$(C_{1-4})$alkyl, $C(O)NH_2$, $C(O)OR^1$, $NR^2R^3$, morpholino or 1-pyrrolyl, wherein $R^1$ is H or $(C_{1-4})$alkyl, and wherein $R^2$ and $R^3$ each independently is H or $(C_{1-4})$alkyl; wherein said substituents are sterically compatible; or (ii) unsaturated or saturated 5- or 6-membered carbocycle substituted with phenyl or naphthyl, said unsaturated or saturated carbocycle, or the phenyl or naphthyl optionally substituted with the same 1 to 3 substituents as defined for the substituents in section (i); or (iii) benzimidazole optionally N-substituted with phenyl or a fused phenyl-carbocycle as defined above;

X' is a valence bond, O, S, SO, $SO_2$, $NR^4$ or $CR^{4A}R^{4B}$, wherein $R^4$ is H or $(C_{1-4})$alkyl; $R^{4A}$ and $R^{4B}$ are each independently H or $(C_{1-4})$alkyl; and wherein when X' is O, S, SO, $SO_2$ or $NR^4$, then W is a divalent radical selected from:

(A) $(CR^5R^{5A})_{1-2}$—$C(Z^A)NR^6$; wherein $R^5$ and $R^{5A}$ are each independently H or $(C_{1-4})$alkyl; $R^6$ is H or $(C_{1-4})$alkyl, and $Z^A$ is oxo or thioxo;

(B) $D-C(Z^B)$; wherein D is $(C_{1-4})$alkylene, $(C_{1-4})$alkylene-O or $(C_{1-4})$alkylene-$NR^7$; wherein $R^7$ is H or $(C_{1-4})$alkyl; and $Z^B$ is oxo or thioxo;

(C)$CH_2C(Z^C)NR^{7A}(C_{1-4})$alkylene; wherein $Z^C$ is oxo or thioxo; and $R^{7A}$ is H or $(C_{1-4})$alkyl;

(D) $(C_{1-4})$alkylene-$NR^{7B}C(Z^D)NR^{7C}$; wherein $R^{7B}$ and $R^{7C}$ are each independently H or $(C_{1-4})$alkyl; and $Z^D$ is oxo or thioxo;

(E) $(C_{1-4})$alkylene optionally substituted with OH, or optionally disubstituted with OH when the $(C_{1-4})$ alkylene contains 2 to 4 carbon atoms; $(C_{2-4})$alkenyl optionally substituted with halo; or cis- or trans-

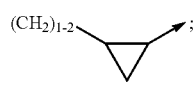

(F) $\{(C_{1-4})$alkylene$\}$-O optionally substituted on the alkylene portion with OH;

(G) $\{(C_{1-4})$alkylene$\}$-$NR^8$ optionally substituted on the alkylene portion with OH; wherein $R^8$ is H or $(C_{1-4})$ alkyl;

(H) $(C_{1-4})$alkylene-$C(Z^E)(C_{1-4})$alkylene; wherein $Z^E$ is oxo or thioxo;

(I)

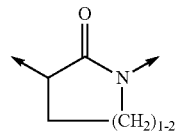

or (J) $(CR^5R^{5A})_{1-2}$—$NR^6$—$(CR^5R^{5A})_{1-2}$; wherein $R^5$ and $R^{5A}$ are each independently H or $(C_{1-4})$alkyl; and $R^6$ is H or $(C_{1-4})$alkyl; or or a metabolite, pharmaceutically acceptable salt, solvate, polymorph, ester, tautomer or prodrug thereof:

In some embodiments, X' is a valence bond, and W is $\{(C_{2-4})$alkenyl$\}C(O)NR^{8A}$; cis- or trans-

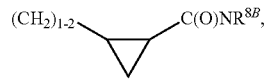

or cis- or trans-

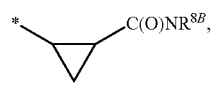

wherein $R^{8A}$ and $R^{8B}$ are each independently H or $(C_{1-4})$alkyl. In other specific embodiments, X' is $CR^{4A}R^{4B}$, and W is $\{(C_{1-4})$alkylene$\}C(O)NR^{8C}$, S-$\{(C_{1-4})$alkylene$\}C(O)NR^{8D}$, O-$\{(C_{1-4})$-alkylene$\}C(O)NR^{8E}$, or $NR^{8F}$—$\{(C_{1-4})$alkylene$\}$-$NR^{8G}$, wherein $R^{8C}$, $R^{8D}$, $R^{8E}$, $R^{8F}$ and $R^{8G}$ are each independently H or $(C_{1-4})$alkyl.

In some specific embodiments, the subject in need of decreased uric acid levels has a disorder characterized by an abnormally high content of uric acid in one or more tissues or organs of the subject. In some specific embodiments, the disorder is characterized by overproduction of uric acid, low excretion of uric acid, tumor lysis, a blood disorder or a combination thereof. In some embodiments, the blood disorder is polycythemia or myeloid metaplasia. In some embodiments, the subject in need of decreased uric acid levels is suffering from gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis or sarcoidosis. In some embodiments, the tissue or organ is blood.

In some embodiments, the blood uric acid level is decreased by at least about 1 mg/dL. In other embodiments, the blood uric acid level is decreased by at least about 2 mg/dL.

In some embodiments, the uric acid levels are decreased by at least about 10% in one or more tissues or organs of the subject. In some embodiments, the uric acid levels are decreased by at least about 25% in one or more tissues or organs of the subject. In some embodiments, the uric acid levels are decreased by at least about 50% in one or more tissues or organs of the subject.

Also provided herein are methods for decreasing uric acid levels in one or more tissues or organs of a subject comprising administering to the subject a uric acid level decreasing amount of a compound of Formula (I), Formula (II), Formula (III) or Formula (IV) or a metabolite, pharmaceutically acceptable salt, solvate, polymorph, ester, tautomer or prodrug thereof, wherein the reduction in uric acid levels results in a reduction in hypertension or cardiovascular events.

Also provided herein are methods for reducing uric acid production, increasing uric acid excretion or both in a subject, comprising administering to the subject a compound of Formula (I), Formula (II), Formula (III) or Formula (IV) or a metabolite, pharmaceutically acceptable salt, solvate, polymorph, ester, tautomer or prodrug thereof.

Also provided herein are methods for treating or preventing hyperuricemia in a subject comprising administering to the subject an effective amount of a compound of Formula (I), Formula (II), Formula (III) or Formula (IV) or a metabolite, pharmaceutically acceptable salt, solvate, polymorph, ester, tautomer or prodrug thereof.

Also provided herein are methods for treating a subject suffering from a condition characterized by abnormal tissue or organ levels of uric acid comprising administering to the subject an effective amount of a compound of Formula (I), Formula (II), Formula (III) or Formula (IV) or a metabolite, pharmaceutically acceptable salt, solvate, polymorph, ester, tautomer or prodrug thereof.

In some embodiments, the condition is characterized by low tissue levels of uric acid, or by high tissue levels of uric acid. In some embodiments, the condition is selected from gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis or sarcoidosis.

In specific embodiments, the condition is gout. In other specific embodiments, the condition is joint inflammation. In some embodiments the joint inflammation is caused by deposits of uric acid crystals in the joint. In some embodiments the uric acid crystals are deposited in the joint fluid (synovial fluid) or joint lining (synovial lining).

Also provided herein are methods comprising administering an agent effective for the treatment of the condition. In some embodiments, the agent is effective in reducing tissue levels of uric acid. In some specific embodiments, the agent is a nonsteroidal anti-inflammatory drugs (NSAIDs), colchicine, a corticosteroid, adrenocorticotropic hormone (ACTH), probenecid, sulfinpyrazone or allopurinol.

Also provided herein are methods for preventing a condition characterized by abnormal tissue levels of uric acid in a subject at increased risk of developing the condition, comprising administering to the subject an effective amount of a compound of Formula (I), Formula (II), Formula (III) or Formula (IV) or a metabolite, pharmaceutically acceptable salt, solvate, polymorph, ester, tautomer or prodrug thereof.

In some embodiments, the condition is selected from gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis or sarcoidosis.

Provided herein are methods for treating gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis or sarcoidosis in a subject comprising administering to the subject an effective amount of a compound of Formula (I), Formula (II), Formula (III) or Formula (IV) or a metabolite, pharmaceutically acceptable salt, solvate, polymorph, ester, tautomer or prodrug thereof.

Also provided herein are methods for treating gout in a subject comprising administering to the subject an effective amount of a compound of Formula (I), Formula (II), Formula (III) or Formula (IV) or a metabolite, pharmaceutically acceptable salt, solvate, polymorph, ester, tautomer or prodrug thereof.

Provided herein are methods for preventing the formation or reducing the size of tophi/tophus in a subject, comprising administering to the subject an effective amount of a compound of Formula (I), Formula (II), Formula (III) or Formula (IV) or a metabolite, pharmaceutically acceptable salt, solvate, polymorph, ester, tautomer or prodrug thereof.

Also provided herein are methods for treating hypoxanthine-guanine phosphoribosyltransferase (HPRT) deficiency in a subject comprising administering to the subject a compound of Formula (I), Formula (II), Formula (III) or Formula (IV) or a metabolite, pharmaceutically acceptable salt, solvate, polymorph, ester, tautomer or prodrug thereof.

Also provided herein are methods for inhibiting a URAT-1 transporter, comprising contacting the URAT-1 transporter with a compound of Formula (I), Formula (II), Formula (III) or Formula (IV) or a metabolite, pharmaceutically acceptable salt, solvate, polymorph, ester, tautomer or prodrug thereof.

Provided herein in specific embodiments are pharmaceutical compositions comprising: i) a compound of Formula (I), Formula (II), Formula (III) or Formula (IV) or a metabolite, pharmaceutically acceptable salt, solvate, polymorph, ester, tautomer or prodrug thereof; ii) allopurinol; and iii) optionally one or more pharmaceutically acceptable carriers.

Also provided herein are pharmaceutical compositions comprising: i) a compound of Formula (I), Formula (II), Formula (III) or Formula (IV) or a metabolite, pharmaceutically acceptable salt, solvate, polymorph, ester, tautomer or prodrug thereof; ii) at least one agent selected from the group consisting of a nonsteroidal anti-inflammatory drug (NSAID), Ibuprofen, Naproxen, Colchicine, Probenecid and Sulfinpyrazone; and iii) optionally one or more pharmaceutically acceptable carriers.

Also provided herein are pharmaceutical compositions useful in the treatment of edema and hypertension which also maintains uric acid levels at pretreatment levels or causes a decrease in uric acid levels comprising: i) at least one antihypertensive agent; ii) a uric acid level maintaining or lowering amount of a compound of the Formula (I) or a metabolite, pharmaceutically acceptable salt, solvate, polymorph, ester, tautomer or prodrug thereof; and iii) optionally one or more pharmaceutically acceptable carriers.

Provided herein are also pharmaceutical compositions useful in the treatment of cancer which also maintains uric acid levels at pretreatment levels or causes a decrease in uric acid levels comprising: i) at least one anticancer agent;
ii) a uric acid level maintaining or lowering amount of a compound of Formula (I), Formula (II), Formula (III) or Formula (IV) or a metabolite, pharmaceutically acceptable salt, solvate, polymorph, ester, tautomer or prodrug thereof; and iii) optionally one or more pharmaceutically acceptable carriers.

Further provided herein are pharmaceutical compositions useful for reducing the side effects of chemotherapy in a cancer patient, comprising: i) a uric acid level maintaining or lowering amount of a compound of Formula (I), Formula (II), Formula (III) or Formula (IV) or a metabolite, pharmaceutically acceptable salt, solvate, polymorph, ester, tautomer or prodrug thereof; and ii) optionally one or more pharmaceutically acceptable carriers.

DETAILED DESCRIPTION OF THE INVENTION

The novel features of the invention are set forth with particularity in the appended claims. A better understanding of the features and advantages of the present invention will be obtained by reference to the following detailed description that sets forth illustrative embodiments, in which the principles of the invention are utilized.

While preferred embodiments of the present invention have been shown and described herein, such embodiments are provided by way of example only. Various alternatives to the embodiments of the invention described herein may be employed in practicing the invention. It is intended that the following claims define the scope of the invention and that methods and structures within the scope of these claims and their equivalents be covered thereby.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference for the purposes stated herein.

Methods: Aberrant Uric Acid Levels

The present invention also provides methods useful for diseases or disorders related to aberrant uric acid levels. The method includes administering an effective amount of a composition as described herein to a subject with aberrant levels of uric acid such as to restore acceptable or non-aberrant levels of uric acid. The present invention also provides methods useful for decreasing uric acid levels in one or more tissues or organs of a subject in need of decreased uric acid levels, comprising administering to the subject a uric acid level decreasing amount of a composition as described herein. The present invention also provides methods useful for reducing uric acid production, increasing uric acid excretion or both in a subject, comprising administering to the subject an effective amount of a composition as described herein. The present invention also provides methods useful for treating or preventing hyperuricemia in a subject comprising administering to the subject an effective amount of a composition as described herein. The present invention also provides methods useful for treating a subject suffering from a condition characterized by abnormal tissue or organ levels of uric acid comprising administering to the subject an effective amount of a composition as described herein The present invention also provides methods useful for treating a subject suffering from gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis or sarcoidosis, comprising administering to the subject an effective amount of a composition as described herein. The present invention also provides methods useful for preventing a condition characterized by abnormal tissue levels of uric acid in a subject at increased risk of developing the condition, comprising administering to the subject an effective amount of a composition as described herein. The present invention also provides methods useful for treating gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis or sarcoidosisin a subject comprising administering to the subject an effective amount of a composition as described herein. The present invention also provides methods useful for treating gout in a subject comprising administering to the subject an effective amount of a composition as described herein. The present invention also provides methods useful for preventing the formation or reducing the size of tophi/tophus in a subject, comprising administering to the subject an effective amount of a composition as described herein.

Certain Chemical Terminology

Unless defined otherwise, all technical and scientific terms used herein have the same meaning as is commonly understood by one of skill in the art to which the claimed subject matter belongs. In the event that there is a plurality of definitions for terms herein, those in this section prevail. Where reference is made to a URL or other such identifier or address, it is understood that such identifiers can change and particular information on the internet can come and go, but equivalent information can be found by searching the internet or other appropriate reference source. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting.

Definition of standard chemistry terms are found in reference works, including Carey and Sundberg "ADVANCED ORGANIC CHEMISTRY $4^{th}$ ED." Vols. A (2000) and B (2001), Plenum Press, New York. Unless otherwise indicated, conventional methods of mass spectroscopy, NMR, HPLC, IR and UV/Vis spectroscopy and pharmacology, are employed.

Where substituent groups are specified by their conventional chemical formulas, written from left to right, they equally encompass the chemically identical substituents that would result from writing the structure from right to left. As a non-limiting example, —$CH_2O$— is equivalent to —$OCH_2$—.

Unless otherwise noted, the use of general chemical terms, such as though not limited to "alkyl," "amine," "aryl," are equivalent to their optionally substituted forms. For example, "alkyl," as used herein, includes optionally substituted alkyl.

In some embodiments, the compounds presented herein possess one or more stereocenters. In some embodiments, each center exists in the R or S configuration, or combinations thereof. In some embodiments, the compounds presented herein possess one or more double bonds. In some embodiments, each double bond exists in the E (trans) or Z (cis) configuration, or combinations thereof. Presentation of one particular stereoisomer, regioisomer, diastereomer, enantiomer or epimer should be understood to include all possible stereoisomers, regioisomers, diastereomers, enantiomers or epimers and mixtures thereof. Thus, the compounds presented herein include all separate configurational stereoisomeric, regioisomeric, diastereomeric, enantiomeric, and epimeric forms as well as the corresponding mixtures thereof. Techniques for inverting or leaving unchanged a particular stereocenter, and those for resolving mixtures of stereoisomers are found, for example, Furniss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; and Heller, *Acc. Chem. Res.* 1990, 23, 128.

The terms "moiety", "chemical moiety", "group" and "chemical group", as used herein refer to a specific segment or functional group of a molecule. Chemical moieties are often recognized chemical entities embedded in or appended to a molecule.

The term "reactant," as used herein, refers to a nucleophile or electrophile used to create covalent linkages.

The term "bond" or "single bond" refers to a chemical bond between two atoms, or two moieties when the atoms joined by the bond are considered to be part of larger substructure.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl". Further, an optionally substituted group means un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc). With respect to any group containing one or more substituents, such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons (except in those instances where macromolecular substituents are clearly intended, e.g., polypeptides, polysaccharides, polyethylene glycols, DNA, RNA and the like).

As used herein, C$_1$-C$_x$ includes C$_1$-C$_2$, C$_1$-C$_3$ ... C$_1$-C$_x$. By way of example only, a group designated as "C$_1$-C$_4$" indicates that there are one to four carbon atoms in the moiety, i.e. groups containing 1 carbon atom, 2 carbon atoms, 3 carbon atoms or 4 carbon atoms, as well as the ranges C$_1$-C$_2$ and C$_1$-C$_3$. Thus, by way of example only, "C$_1$-C$_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl. Whenever it appears herein, a numerical range such as "1 to 10" refers to each integer in the given range; e.g., "1 to 10 carbon atoms" means 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms.

The term "lower" as used herein in combination with terms such as alkyl, alkenyl or alkynyl, (i.e. "lower alkyl", "lower alkenyl" or "lower alkynyl") refers to an optionally substituted straight-chain, or optionally substituted branched-chain saturated hydrocarbon monoradical having from one to about six carbon atoms, more preferably one to three carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, 2-ethyl-1-butyl, n-butyl, isobutyl, sec-butyl, t-butyl, n-pentyl, isopentyl, neopentyl, tert-amyl and hexyl.

The term "hydrocarbon" as used herein, alone or in combination, refers to a compound or chemical group containing only carbon and hydrogen atoms.

The terms "heteroatom" or "hetero" as used herein, alone or in combination, refer to an atom other than carbon or hydrogen. Heteroatoms include, but are not limited to, oxygen, nitrogen, sulfur, phosphorous, silicon, selenium and tin, but are not limited to these atoms. Where two or more heteroatoms are present, in some embodiments, the two or more heteroatoms are the same as each another. Where two or more heteroatoms are present, in some embodiments, the two or more heteroatoms are different from the others.

The term "alkyl" as used herein, alone or in combination, refers to an optionally substituted straight-chain, or optionally substituted branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "C$_1$-C$_6$ alkyl" or "C$_{1-6}$ alkyl", means that: in some embodiments, the alkyl group consists of 1 carbon atom; in some embodiments, 2 carbon atoms; in some embodiments, 3 carbon atoms; in some embodiments, 4 carbon atoms; in some embodiments, 5 carbon atoms; in some embodiments, 6 carbon atoms. The present definition also covers the occurrence of the term "alkyl" where no numerical range is designated.

The term "alkylene" as used herein, alone or in combination, refers to a diradical derived from the above-defined monoradical, alkyl. Examples include, but are not limited to methylene (—CH$_2$—), ethylene (—CH$_2$CH$_2$—), propylene (—CH$_2$CH$_2$CH$_2$—), isopropylene (—CH(CH$_3$)CH$_2$—) and the like.

The term "alkenyl" as used herein, alone or in combination, refers to an optionally substituted straight-chain, or optionally substituted branched-chain hydrocarbon monoradical having one or more carbon-carbon double-bonds and having from two to about ten carbon atoms, more preferably two to about six carbon atoms. The group includes either the cis or trans conformation about the double bond(s), and should be understood to include both isomers. Examples include, but are not limited to ethenyl (—CH=CH$_2$), 1-propenyl(—CH$_2$CH=CH$_2$), isopropenyl[-C(CH$_3$)=CH$_2$], butenyl, 1,3-butadienyl and the like. Whenever it appears herein, a numerical range such as "C$_2$-C$_6$ alkenyl" or "C$_{2-6}$ alkenyl", means that: in some embodiments, the alkenyl group consists of 2 carbon atoms; in some embodiments, 3 carbon atoms; in some embodiments, 4 carbon atoms; in some embodiments, 5 carbon atoms; in some embodiments, 6 carbon atoms. The present definition also covers the occurrence of the term "alkenyl" where no numerical range is designated.

The term "alkenylene" as used herein, alone or in combination, refers to a diradical derived from the above-defined monoradical alkenyl. Examples include, but are not limited to ethenylene (—CH=CH—), the propenylene isomers (e.g., —CH$_2$CH=CH— and —C(CH$_3$)=CH—) and the like.

The term "alkynyl" as used herein, alone or in combination, refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$ alkynyl", means: in some embodiments, the alkynyl group consists of 2 carbon atoms; in some embodiments, 3 carbon atoms; in some embodiments, 4 carbon atoms; in some embodiments, 5 carbon atoms; in some embodiments, 6 carbon atoms. The present definition also covers the occurrence of the term "alkynyl" where no numerical range is designated.

The term "alkynylene" as used herein, alone or in combination, refers to a diradical derived from the above-defined monoradical, alkynyl. Examples include, but are not limited to ethynylene (—C≡C—), propargylene (—CH$_2$—C≡C—) and the like.

The term "aliphatic" as used herein, alone or in combination, refers to an optionally substituted, straight-chain or branched-chain, non-cyclic, saturated, partially unsaturated, or fully unsaturated nonaromatic hydrocarbon. Thus, the term collectively includes alkyl, alkenyl and alkynyl groups.

The terms "heteroalkyl", "heteroalkenyl" and "heteroalkynyl" as used herein, alone or in combination, refer to optionally substituted alkyl, alkenyl and alkynyl structures respectively, as described above, in which one or more of the skeletal chain carbon atoms (and any associated hydrogen atoms, as appropriate) are each independently replaced with a heteroatom (i.e. an atom other than carbon, such as though not limited to oxygen, nitrogen, sulfur, silicon, phosphorous, tin or combinations thereof), or heteroatomic group such as though not limited to —O—O—, —S—S—, —O—S—, —S—O—, =N—N=, —N=N—, —N=N—NH—, —P(O)$_2$—, —O—P(O)$_2$—, —P(O)$_2$—O—, —S(O)—, —S(O)$_2$—, —SnH$_2$— and the like.

The terms "haloalkyl", "haloalkenyl" and "haloalkynyl" as used herein, alone or in combination, refer to optionally substituted alkyl, alkenyl and alkynyl groups respectively, as defined above, in which one or more hydrogen atoms is replaced by fluorine, chlorine, bromine or iodine atoms, or combinations thereof. In some embodiments, two or more hydrogen atoms are replaced with halogen atoms that are the same as each another (e.g. difluoromethyl); in other embodiments, two or more hydrogen atoms are replaced with halogen atoms that are not all the same as each other (e.g. 1-chloro-1-fluoro-1-iodoethyl). Non-limiting examples of haloalkyl groups are fluoromethyl and bromoethyl. A non-limiting example of a haloalkenyl group is bromoethenyl. A non-limiting example of a haloalkynyl group is chloroethynyl.

The term "perhalo" as used herein, alone or in combination, refers to groups in which all of the hydrogen atoms are replaced by fluorines, chlorines, bromines, iodines, or combinations thereof. Thus, as a non-limiting example, the term "perhaloalkyl" refers to an alkyl group, as defined herein, in which all of the H atoms have been replaced by fluorines, chlorines, bromines or iodines, or combinations thereof. A non-limiting example of a perhaloalkyl group is bromo,chloro,fluoromethyl. A non-limiting example of a perhaloalkenyl group is trichloroethenyl. A non-limiting example of a perhaloalkynyl group is tribromopropynyl.

The term "carbon chain" as used herein, alone or in combination, refers to any alkyl, alkenyl, alkynyl, heteroalkyl, heteroalkenyl or heteroalkynyl group, which is linear, cyclic, or any combination thereof. If the chain is part of a linker and that linker comprises one or more rings as part of the core backbone, for purposes of calculating chain length, the "chain" only includes those carbon atoms that compose the bottom or top of a given ring and not both, and where the top and bottom of the ring(s) are not equivalent in length, the shorter distance shall be used in determining the chain length. If the chain contains heteroatoms as part of the backbone, those atoms are not calculated as part of the carbon chain length.

The terms "cycle", "cyclic", "ring" and "membered ring" as used herein, alone or in combination, refer to any covalently closed structure, including alicyclic, heterocyclic, aromatic, heteroaromatic and polycyclic fused or non-fused ring systems as described herein. In some embodiments, rings are optionally substituted. In some embodiments, rings form part of a fused ring system. The term "membered" is meant to denote the number of skeletal atoms that constitute the ring. Thus, by way of example only, cyclohexane, pyridine, pyran and pyrimidine are six-membered rings and cyclopentane, pyrrole, tetrahydrofuran and thiophene are five-membered rings.

The term "fused" as used herein, alone or in combination, refers to cyclic structures in which two or more rings share one or more bonds.

The term "cycloalkyl" as used herein, alone or in combination, refers to an optionally substituted, saturated, hydrocarbon monoradical ring, containing from three to about fifteen ring carbon atoms or from three to about ten ring carbon atoms. In some embodiments, the compound includes additional, non-ring carbon atoms as substituents (e.g. methylcyclopropyl). Whenever it appears herein, a numerical range such as "$C_3$-$C_6$ cycloalkyl" or "$C_{3-6}$ cycloalkyl", means: in some embodiments, the cycloalkyl group consists of 3 carbon atoms (e.g., cyclopropyl); in some embodiments, 4 carbon atoms (e.g., cyclobutyl); in some embodiments, 5 carbon atoms (e.g., cyclopentyl); in some embodiments, 6 carbon atoms (e.g., cyclohexyl); in some embodiments, 7 carbon atoms (e.g., cyclohepty). The present definition also covers the occurrence of the term "cycloalkyl" where no numerical range is designated. Further, the term includes fused, non-fused, bridged and spiro radicals. A fused cycloalkyl contains from two to four fused rings where the ring of attachment is a cycloalkyl ring, and the other individual rings are alicyclic, heterocyclic, aromatic, heteroaromatic or any combination thereof. Examples include, but are not limited to cyclopropyl, cyclopentyl, cyclohexyl, decalinyl, and bicyclo[2.2.1]heptyl and adamantyl ring systems. Illustrative examples include, but are not limited to the following moieties:

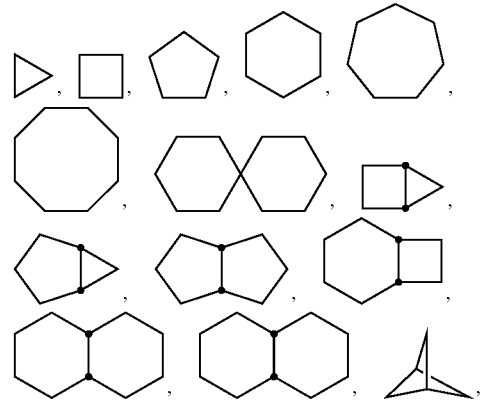

-continued

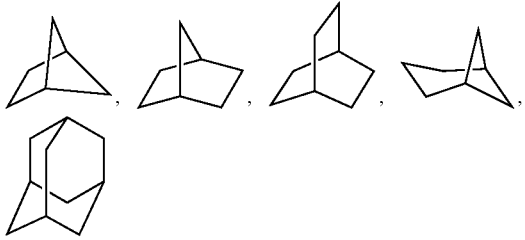

and the like.

The term "cycloalkenyl" as used herein, alone or in combination, refers to an optionally substituted hydrocarbon non-aromatic, monoradical ring, having one or more carbon-carbon double-bonds and from three to about twenty ring carbon atoms, three to about twelve ring carbon atoms, or from three to about ten ring carbon atoms. The term includes fused, non-fused, bridged and spiro radicals. A fused cycloalkenyl contains from two to four fused rings where the ring of attachment is a cycloalkenyl ring, and the other individual rings are alicyclic, heterocyclic, aromatic, heteroaromatic or any combination thereof. In some embodiments, fused ring systems are fused across a bond that is a carbon-carbon single bond or a carbon-carbon double bond. Examples of cycloalkenyls include, but are not limited to cyclohexenyl, cyclopentadienyl and bicyclo[2.2.1]hept-2-ene ring systems. Illustrative examples include, but are not limited to the following moieties:

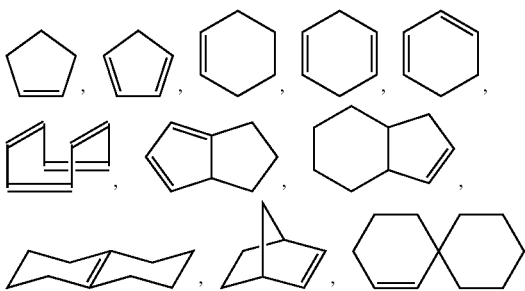

and the like.

The terms "alicyclyl" or "alicyclic" as used herein, alone or in combination, refer to an optionally substituted, saturated, partially unsaturated, or fully unsaturated nonaromatic hydrocarbon ring systems containing from three to about twenty ring carbon atoms, three to about twelve ring carbon atoms, or from three to about ten ring carbon atoms. Thus, the terms collectively include cycloalkyl and cycloalkenyl groups.

The terms "non-aromatic heterocyclyl" and "heteroalicyclyl" as used herein, alone or in combination, refer to optionally substituted, saturated, partially unsaturated, or fully unsaturated nonaromatic ring monoradicals containing from three to about twenty ring atoms, where one or more of the ring atoms are an atom other than carbon, independently selected from among oxygen, nitrogen, sulfur, phosphorous, silicon, selenium and tin but are not limited to these atoms. Where two or more heteroatoms are present in the ring, in some embodiments, the two or more heteroatoms are the same as each another; in some embodiments, some or all of the two or more heteroatoms are different from the others. The terms include fused, non-fused, bridged and spiro radicals. A fused non-aromatic heterocyclic radical contains from two to four fused rings where the attaching ring is a non-aromatic heterocycle, and the other individual rings are alicyclic, heterocyclic, aromatic, heteroaromatic or any combination thereof. Fused ring systems are fused across a single bond or a double bond, as well as across bonds that are carbon-carbon, carbon-hetero atom or hetero atom-hetero atom. The terms also include radicals having from three to about twelve skeletal ring atoms, as well as those having from three to about ten skeletal ring atoms. In some embodiments, attachment of a non-aromatic heterocyclic subunit to its parent molecule is via a heteroatom; in some embodiments, via a carbon atom. In some embodiments, additional substitution is via a heteroatom or a carbon atom. As a non-limiting example, an imidazolidine non-aromatic heterocycle is attached to a parent molecule via either of its N atoms (imidazolidin-1-yl or imidazolidin-3-yl) or any of its carbon atoms (imidazolidin-2-yl, imidazolidin-4-yl or imidazolidin-5-yl). In certain embodiments, non-aromatic heterocycles contain one or more carbonyl or thiocarbonyl groups such as, for example, oxo- and thio-containing groups. Examples include, but are not limited to pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Illustrative examples of heterocycloalkyl groups, also referred to as non-aromatic heterocycles, include:

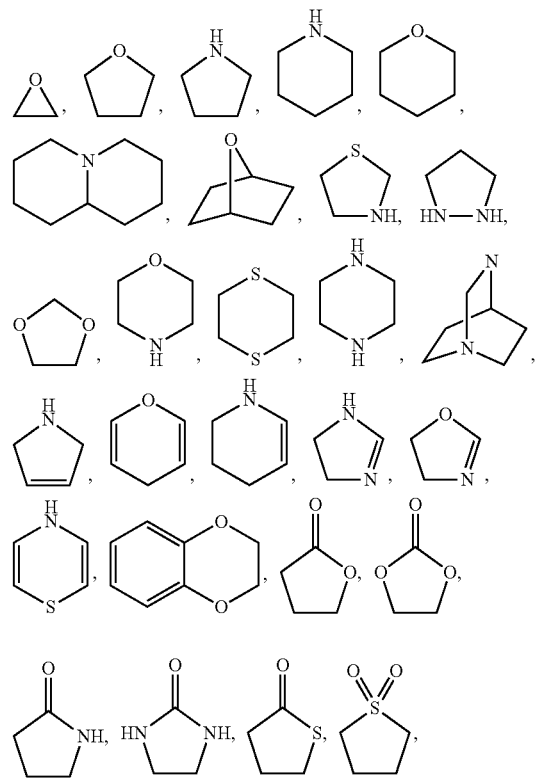

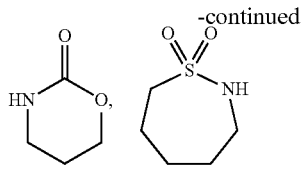

and the like.

The terms also include all ring forms of the carbohydrates, including but not limited to the monosaccharides, the disaccharides and the oligosaccharides.

The term "aromatic" as used herein, refers to a planar, cyclic or polycyclic, ring moiety having a delocalized π-electron system containing 4n+2π electrons, where n is an integer. In some embodiments, aromatic rings are formed by five atoms; in some embodiments, six atoms; in some embodiments, seven atoms; in some embodiments, eight atoms; in some embodiments, nine atoms; in some embodiments, more than nine atoms. Aromatics are optionally substituted and are monocyclic or fused-ring polycyclic. The term aromatic encompasses both all carbon containing rings (e.g., phenyl) and those rings containing one or more heteroatoms (e.g., pyridine).

The term "aryl" as used herein, alone or in combination, refers to an optionally substituted aromatic hydrocarbon radical of six to about twenty ring carbon atoms, and includes fused and non-fused aryl rings. A fused aryl ring radical contains from two to four fused rings, where the ring of attachment is an aryl ring, and the other individual rings are alicyclic, heterocyclic, aromatic, heteroaromatic or any combination thereof. Further, the term aryl includes fused and non-fused rings containing from six to about twelve ring carbon atoms, as well as those containing from six to about ten ring carbon atoms. A non-limiting example of a single ring aryl group includes phenyl; a fused ring aryl group includes naphthyl, phenanthrenyl, anthracenyl, azulenyl; and a non-fused bi-aryl group includes biphenyl.

The term "arylene" as used herein, alone or in combination, refers to a diradical derived from the above-defined monoradical, aryl. Examples include, but are not limited to 1,2-phenylene, 1,3-phenylene, 1,4-phenylene, 1,2-naphthylene and the like.

The term "heteroaryl" as used herein, alone or in combination, refers to optionally substituted aromatic monoradicals containing from about five to about twenty skeletal ring atoms, where one or more of the ring atoms is a heteroatom independently selected from among oxygen, nitrogen, sulfur, phosphorous, silicon, selenium and tin but not limited to these atoms and with the proviso that the ring of said group does not contain two adjacent O or S atoms. Where two or more heteroatoms are present in the ring, in some embodiments, the two or more heteroatoms are the same as each another; in some embodiments, some or all of the two or more heteroatoms are be different from the others. The term heteroaryl includes optionally substituted fused and non-fused heteroaryl radicals having at least one heteroatom. The term heteroaryl also includes fused and non-fused heteroaryls having from five to about twelve skeletal ring atoms, as well as those having from five to about ten skeletal ring atoms. In some embodiments, bonding to a heteroaryl group is via a carbon atom; in some embodiments, via a heteroatom. Thus, as a non-limiting example, an imidiazole group is attached to a parent molecule via any of its carbon atoms (imidazol-2-yl, imidazol-4-yl or imidazol-5-yl), or its nitrogen atoms (imidazol-1-yl or imidazol-3-yl). Further, in some embodiments, a heteroaryl group is substituted via any or all of its carbon atoms, and/or any or all of its heteroatoms. A fused heteroaryl radical contains from two to four fused rings, where the ring of attachment is a heteroaromatic ring. In some embodiments, the other individual rings are alicyclic, heterocyclic, aromatic, heteroaromatic or any combination thereof. A non-limiting example of a single ring heteroaryl group includes pyridyl; fused ring heteroaryl groups include benzimidazolyl, quinolinyl, acridinyl; and a non-fused bi-heteroaryl group includes bipyridinyl. Further examples of heteroaryls include, without limitation, furanyl, thienyl, oxazolyl, acridinyl, phenazinyl, benzimidazolyl, benzofuranyl, benzoxazolyl, benzothiazolyl, benzothiadiazolyl, benzothiophenyl, benzoxadiazolyl, benzotriazolyl, imidazolyl, indolyl, isoxazolyl, isoquinolinyl, indolizinyl, isothiazolyl, isoindolyloxadiazolyl, indazolyl, pyridyl, pyridazyl, pyrimidyl, pyrazinyl, pyrrolyl, pyrazinyl, pyrazolyl, purinyl, phthalazinyl, pteridinyl, quinolinyl, quinazolinyl, quinoxalinyl, triazolyl, tetrazolyl, thiazolyl, triazinyl, thiadiazolyl and the like, and their oxides, such as for example pyridyl-N-oxide. Illustrative examples of heteroaryl groups include the following moieties:

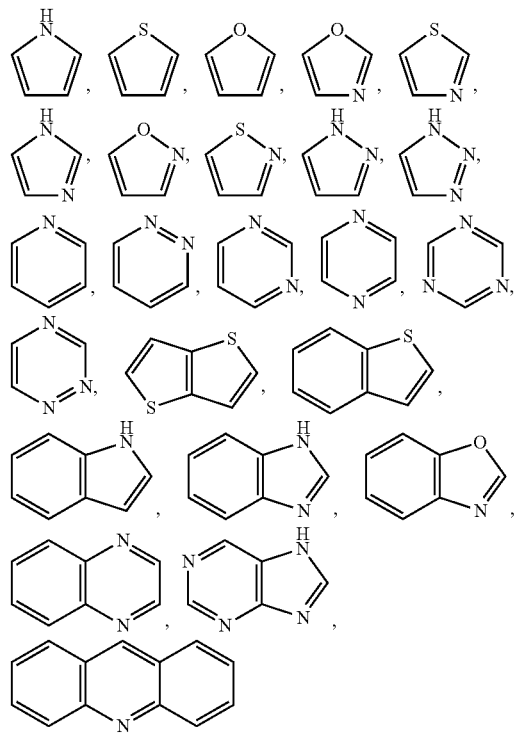

and the like.

The term "heteroarylene" as used herein, alone or in combination, refers to a diradical derived from the above-defined monoradical heteroaryl. Examples include, but are not limited to pyridinyl and pyrimidinyl.

The term "heterocyclyl" as used herein, alone or in combination, refers collectively to heteroalicyclyl and heteroaryl groups. Herein, whenever the number of carbon atoms in a heterocycle is indicated (e.g., $C_1$-$C_6$ heterocycle), at least one non-carbon atom (the heteroatom) must be present in the ring. Designations such as "$C_1$-$C_6$ heterocycle" refer only to the number of carbon atoms in the ring and do not refer to the total number of atoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). For heterocycles having two or more heteroatoms, in some embodiments, those two or more heteroatoms are the same; in some embodiments, they are different from one another. In some embodiments, heterocycles are substituted. Non-aromatic heterocyclic groups include groups having only three atoms in the ring, while aromatic heterocyclic groups must have at least five atoms in the ring. In some embodiments, bonding (i.e. attachment to a parent molecule or further substitution) to a heterocycle is via a heteroatom; in some embodiments, via a carbon atom.

The term "carbocyclyl" as used herein, alone or in combination, refers collectively to alicyclyl and aryl groups; i.e. all carbon, covalently closed ring structures. In some embodiments, the carbocyclyl is saturated, partially unsaturated, fully unsaturated or aromatic. In some embodiments, carbocyclic rings are formed by three, carbon atoms; in some embodiments, four carbon atoms; in some embodiments, five carbon atoms; in some embodiments, six carbon atoms; in some embodiment, seven carbon atoms; in some embodiments, eight carbon atoms; in some embodiments, nine carbon atoms; in some embodiments, more than nine carbon atoms. Carbocycles are optionally substituted. The term distinguishes carbocyclic from heterocyclic rings in which the ring backbone contains at least one atom which is different from carbon.

The terms "halogen", "halo" or "halide" as used herein, alone or in combination refer to fluoro, chloro, bromo and iodo.

The term "hydroxy" as used herein, alone or in combination, refers to the monoradical —OH.

The term "cyano" as used herein, alone or in combination, refers to the monoradical —CN.

The term "cyanomethyl" as used herein, alone or in combination, refers to the monoradical —CH$_2$CN.

The term "nitro" as used herein, alone or in combination, refers to the monoradical —NO$_2$.

The term "oxy" as used herein, alone or in combination, refers to the diradical —O—.

The term "oxo" as used herein, alone or in combination, refers to the diradical =O.

The term "carbonyl" as used herein, alone or in combination, refers to the diradical —C(=O)—, which is also written as —C(O)—.

The terms "carboxy" or "carboxyl" as used herein, alone or in combination, refer to the moiety —C(O)OH, which is alternatively written as —COOH.

The term "alkoxy" as used herein, alone or in combination, refers to an alkyl ether radical, —O-alkyl, including the groups —O-aliphatic and —O-carbocyclyl, wherein the alkyl, aliphatic and carbocyclyl groups are optionally substituted, and wherein the terms alkyl, aliphatic and carbocyclyl are as defined herein. Non-limiting examples of alkoxy radicals include methoxy, ethoxy, n-propoxy, isopropoxy, n-butoxy, iso-butoxy, sec-butoxy, tert-butoxy and the like.

The term "sulfinyl" as used herein, alone or in combination, refers to the diradical —S(=O)—.

The term "sulfonyl" as used herein, alone or in combination, refers to the diradical —S(=O)$_2$—.

The terms "sulfonamide", "sulfonamido" and "sulfonamidyl" as used herein, alone or in combination, refer to the diradical groups —S(=O)$_2$—NH— and —NH—S(=O)$_2$—.

The terms "sulfamide", "sulfamido" and "sulfamidyl" as used herein, alone or in combination, refer to the diradical group —NH—S(=O)$_2$—NH—.

It is to be understood that in instances where two or more radicals are used in succession to define a substituent attached to a structure, the first named radical is considered to be terminal and the last named radical is considered to be attached to the structure in question. Thus, for example, the radical arylalkyl is attached to the structure in question by the alkyl group.

Certain Pharmaceutical Terminology

The term "subject", "patient" or "individual" as used herein in reference to individuals suffering from a disorder, and the like, encompasses mammals and non-mammals. Mammals are any member of the Mammalian class, including but not limited to humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In some embodiments of the methods and compositions provided herein, the subject is a mammal. In preferred embodiments, the subject is a human.

The terms "treat," "treating" or "treatment," and other grammatical equivalents as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that, in some embodiments, the patient is still afflicted with the underlying disorder. For prophylactic benefit, the compositions are administered to a patient at risk of developing a particular disease, or to a patient reporting one or more of the physiological symptoms of a disease, even if a diagnosis of the disease has not been made.

The terms "administer," "administering", "administration," and the like, as used herein, refer to the methods that are used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. In preferred embodiments, the compounds and compositions described herein are administered orally.

The terms "effective amount", "therapeutically effective amount" or "pharmaceutically effective amount" as used herein, refer to a sufficient amount of at least one agent or compound being administered which will relieve to some extent one or more of the symptoms of the disease or condition being treated. In some embodiments, the result is a reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. In some embodiments, the "effective" amount differs from one individual to another. In some embodiments, an appropriate "effective" amount is determined using any suitable technique (e.g., a dose escalation study).

The term "acceptable" as used herein, with respect to a formulation, composition or ingredient, means having no persistent detrimental effect on the general health of the subject being treated.

The term "pharmaceutically acceptable" as used herein, refers to a material, such as a carrier or diluent, which does not abrogate the biological activity or properties of a compound disclosed herein, and is relatively nontoxic (i.e., when the material is administered to an individual it does not cause undesirable biological effects nor does it interact in a deleterious manner with any of the components of the composition in which it is contained).

The term "prodrug" as used herein, refers to a drug precursor that, following administration to a subject and subsequent absorption, is converted to an active, or a more active species via some process, such as conversion by a metabolic pathway. Thus, the term encompasses any derivative of a compound, which, upon administration to a recipient, is capable of providing, either directly or indirectly, a compound of this invention or a pharmaceutically active metabolite or residue thereof. Some prodrugs have a chemical group present on the prodrug that renders it less active and/or confers solubility or some other property to the drug. Once the chemical group has been cleaved and/or modified from the prodrug the active drug is generated. Particularly favored derivatives or prodrugs are those that increase the bioavailability of the compounds of this invention when such compounds are administered to a patient (e.g. by allowing an orally administered compound to be more readily absorbed into the blood) or which enhance delivery of the parent compound to a biological compartment (e.g. the brain or lymphatic system).

The term "pharmaceutically acceptable salt" as used herein, refers to salts that retain the biological effectiveness of the free acids and bases of the specified compound and that are not biologically or otherwise undesirable. In some embodiments, a compound disclosed herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free base form with a suitable organic or inorganic acid, and isolating the salt thus formed.

The term "pharmaceutical composition," as used herein, refers to a biologically active compound, optionally mixed with at least one pharmaceutically acceptable chemical component, such as, though not limited to carriers, stabilizers, diluents, dispersing agents, suspending agents, thickening agents, excipients and the like.

The term "carrier" as used herein, refers to relatively nontoxic chemical compounds or agents that facilitate the incorporation of a compound into cells or tissues.

The terms "pharmaceutical combination", "administering an additional therapy", "administering an additional therapeutic agent" and the like, as used herein, refer to a pharmaceutical therapy resulting from the mixing or combining of more than one active ingredient and includes both fixed and non-fixed combinations of a compound or composition disclosed herein. The term "fixed combination" means that at least one of a compound disclosed herein, and at least one co-agent, are both administered to a patient simultaneously in the form of a single entity or dosage. The term "non-fixed combination" means that at least one of a compound disclosed herein, and at least one co-agent, are administered to a patient as separate entities either simultaneously, concurrently or sequentially with variable intervening time limits, wherein such administration provides effective levels of the two or more compounds in the body of the patient. These also apply to cocktail therapies, e.g. the administration of three or more active ingredients.

The terms "co-administration", "administered in combination with" and their grammatical equivalents or the like, as used herein, are meant to encompass administration of the selected therapeutic agents to a single patient, and are intended to include treatment regimens in which the agents are administered by the same or different route of administration or at the same or different times. In some embodiments, a compound disclosed herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the compounds of the invention and the other agent(s) are administered in a single composition. In some embodiments, compounds of the invention and the other agent(s) are admixed in the composition.

The term "metabolite," as used herein, refers to a derivative of a compound which is formed when the compound is metabolized.

The term "active metabolite," as used herein, refers to a biologically active derivative of a compound that is formed when the compound is metabolized.

The term "metabolized," as used herein, refers to the sum of the processes (including, but not limited to, hydrolysis reactions and reactions catalyzed by enzymes) by which a particular substance is changed by an organism. In some embodiments, enzymes produce structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism is found in *The Pharmacological Basis of Therapeutics*, 9th Edition, McGraw-Hill (1996).

Compounds

Provided herein are compounds of Formula (I):

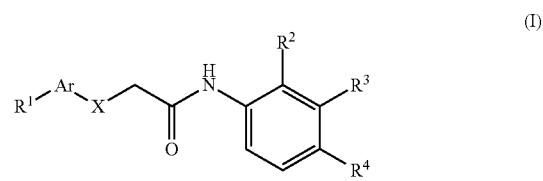

wherein:
  Ar is a 5-membered aromatic heterocycle containing 1 to 4 heteroatoms each independently selected from N, O and S; said heterocycle being optionally substituted at a substitutable position with $R^{Ar}$, wherein $R^{Ar}$ is H, $(C_{1-4})$ alkyl, $CF_3$ or $(C_{3-7})$cycloalkyl and wherein the groups X and $R^1$ are attached to positions on the Ar ring which are immediately adjacent to each other;
  X is selected from O and S;

$R^1$ is a group of formula:

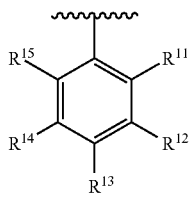

wherein $R^{11}$ is halo; and $R^{12}$, $R^{13}$, $R^{14}$ and $R^{15}$ are each independently selected from H, halo, $(C_{1-4})$alkyl, $CF_3$, $(C_{3-7})$cycloalkyl, $(C_{3-7})$cycloalkyl-$(C_{1-4})$alkyl-, cyano, —O—$(C_{1-4})$alkyl, —$OCF_3$ and —$N((C_{1-4})$alkyl$)_2$, wherein said $(C_{3-7})$cycloalkyl is optionally substituted with $(C_{1-4})$alkyl; or $R^{12}$ and $R^{13}$, $R^{13}$ and $R^{14}$, or $R^{14}$ and $R^{15}$ are linked, together with the carbon atoms to which they are attached, to form a five- or six-membered saturated, unsaturated or aromatic ring which optionally contains from one to three heteroatoms each independently selected from O, S and N, wherein the remaining of $R^{12}$, $R^{13}$, $R^{14}$ and $R^{15}$ are defined as hereinbefore;

$R^2$ is selected from halo, nitro and $(C_{1-4})$alkyl;
$R^3$ is selected from H and halo;
$R^4$ is selected from:
(A)

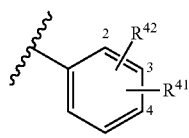

wherein $R^{42}$ is bonded to position 2 or position 3 of the phenyl ring and is selected from H, halo and $(C_{1-4})$alkyl; and $R^{41}$ is bonded to position 3 or position 4 of the phenyl ring and is selected from:
  i) $(C_{1-4})$alkyl substituted with —COOH, —COO$(C_{1-4})$alkyl, —C(=O)$NH_2$, —C(=O)$NHSO_2$—$(C_{1-4})$alkyl, or —OH;
  ii) $(C_{2-4})$alkenyl substituted with —COOH or —COO$(C_{1-4})$alkyl;
  iii) —O—$(C_{1-4})$alkyl optionally substituted with —COOH, Het, or —N$((C_{1-6})$alkyl$)_2$, wherein said Het is optionally substituted with —OH or —COOH and wherein either or both of the $(C_{1-6})$alkyl groups in said —N$((C_{1-6})$alkyl$)_2$ are optionally substituted with —COOH or —COO$(C_{1-4})$alkyl; and
  iv) —OH, —COOH, —COO$(C_{1-4})$alkyl, —$SO_2NH_2$, or —$SO_2$—$(C_{1-4})$alkyl;
  provided that $R^{42}$ and $R^{41}$ is not both be bonded to position 3 of the phenyl ring at the same time;
(B) $(C_{2-4})$alkenyl substituted with —COOH or —COO$(C_{1-4})$alkyl;
(C) Het optionally substituted with $(C_{1-6})$alkyl, —$NH_2$, —COOH, or $(C_{2-4})$alkenyl substituted with —COOH;
(D)-$SO_2N(R^{43})R^{44}$, wherein $R^{43}$ is H or $(C_{1-6})$alkyl and $R^{44}$ is selected from $(C_{1-6})$alkyl, phenyl, phenyl-$(C_{1-4})$alkyl-, —C(=O)NH$(C_{1-4})$alkyl, —C(=O)O$(C_{1-4})$alkyl, and Het; wherein said $(C_{1-6})$alkyl is optionally substituted with —OH or —COOH and wherein said Het is optionally substituted with $(C_{1-6})$alkyl; or $R^{43}$ and $R^{44}$, together with the N to which they are attached, are linked together to form a 5- or 6-membered heterocycle which is saturated or unsaturated and which is optionally contain from one to three further heteroatoms each independently selected from N, O and S; said heterocycle being optionally substituted with $(C_{1-6})$alkyl or —COOH;
(E) —O—$(C_{1-4})$alkyl substituted with —OH, —COOH or Het, wherein said Het is optionally substituted with —COOH or —COO$(C_{1-6})$alkyl; provided that the carbon atom of —O—$(C_{1-4})$alkyl which is directly bonded to 0 is not also directly bonded to —OH;
(F) —C(=O)N($R^5$)$R^6$ or —O—$CH_2$—C(=O)N($R^5$)$R^6$ wherein $R^5$ is H or $(C_{1-6})$alkyl and $R^6$ is selected from:
  i) phenyl optionally substituted with one or two substituents each independently selected from —OH, —COOH, —N($(C_{1-4})$alkyl$)_2$, $(C_{1-4})$alkyl, $(C_{2-4})$alkenyl and Het; wherein said $(C_{1-4})$alkyl is optionally substituted with —COOH and said $(C_{2-4})$alkenyl is substituted with —COOH;
  ii) $(C_{1-4})$alkyl optionally substituted with one or two substituents each independently selected from —COOH, —OH, —S—$(C_{1-6})$alkyl and Het; provided that the carbon atom of $(C_{1-4})$alkyl which is directly bonded to N is not also directly bonded to —OH;
  iii) phenyl-$(C_{1-4})$alkyl- wherein the phenyl portion of said phenyl-$(C_{1-4})$alkyl- is optionally substituted with one or two substituents each independently selected from —OH, —$NH_2$, and —COOH;
  iv) $(C_{3-7})$cycloalkyl-$(C_{1-4})$alkyl- wherein the cycloalkyl portion of said $(C_{3-7})$cycloalkyl-$(C_{1-4})$alkyl- is optionally substituted with —COOH;
  v) Het optionally substituted with one or two substituents each independently selected from $(C_{1-6})$alkyl, phenyl-$(C_{1-4})$alkyl- and —COOH;
  vi) $(C_{3-7})$cycloalkyl; and
  vii) —$SO_2$—$R^{61}$ wherein $R^{61}$ is $(C_{1-4})$alkyl or phenyl; or
  $R^5$ and $R^6$, together with the N to which they are attached, are linked together to form a 5- or 6-membered heterocycle which is saturated or unsaturated and which is optionally contain from one to three further heteroatoms each independently selected from N, O and S; said heterocycle being optionally substituted with one or two substituents each independently selected from $(C_{1-6})$alkyl, —COOH and —COO$(C_{1-6})$alkyl;
(G) —NHC(=O)—$R^7$ wherein $R^7$ is selected from:
  i) $(C_{1-6})$alkyl optionally substituted with one or two substituents each independently selected from —COOH, —O—$(C_{1-4})$alkyl, —NHC(=O)—$(C_{1-4})$alkyl, phenyl and Het; wherein said phenyl is optionally substituted with one or two substituents each independently selected from halo, —OH, —O—$(C_{1-4})$alkyl, —$NO_2$, —COOH, —$NH_2$, —NH$(C_{1-4})$alkyl, —N$((C_{1-4})$alkyl$)_2$, and $(C_{1-6})$alkyl optionally substituted with from one to three halo substituents;
  ii) phenyl optionally substituted with —OH, halo or —COOH;
  iii) —NH$R^{71}$ wherein $R^{71}$ is phenyl or phenyl-$(C_{1-4})$alkyl-, wherein said phenyl is optionally substituted with —COOH or —COO(C$_{1-4}$)alkyl; and iv) (C$_{1-6}$)alkynyl, (C$_{3-7}$)cycloalkyl or (C$_{3-7}$)cycloalkyl-(C$_{1-4}$)alkyl-;

(H) —NHSO$_2$R$^8$ wherein R$^8$ is selected from phenyl, phenyl-(C$_{1-4}$)alkyl- and Het; and (I) —C≡C—R$^9$ wherein R$^9$ is selected from:
  i) H, —COOH, —COO(C$_{1-6}$)alkyl, phenyl or (C$_{2-4}$)alkenyl;
  ii) (C$_{3-7}$)cycloalkyl optionally substituted with —OH, —COOH, —COO(C$_{1-6}$)alkyl, or (C$_{1-4}$)alkyl wherein said (C$_{1-4}$)alkyl is optionally substituted with —OH or —N(R$^{91}$)R$^{92}$, wherein R$^{91}$ is H and R$^{92}$ is (C$_{1-4}$)alkyl substituted with Het; or R$^{91}$ and R$^{92}$, together with the N to which they are attached, are linked together to form a 5- or 6-membered heterocycle which is saturated, unsaturated or aromatic and which is optionally contain from one to three further heteroatoms each independently selected from N, O and S; said heterocycle being optionally substituted with one or two substituents each independently selected from (C$_{1-6}$)alkyl and —OH; and
  iii) (C$_{1-6}$)alkyl optionally substituted with one, two or three substituents each independently selected from:
    a) —OH, —O(C═O)NH$_2$, —O(C═O)NH(C$_{1-4}$)alkyl, CF$_3$, —COOH or —COO—(C$_{1-4}$)alkyl;
    b) Het optionally substituted with (C$_{1-6}$)alkyl or —OH;
    c) —N(R$^{93}$)R$^{94}$ wherein R$^{93}$ is H or (C$_{1-4}$)alkyl and R$^{94}$ is selected from H, —(C$_{1-4}$)alkyl optionally substituted with R$^{941}$, —SO$_2$—(C$_{1-4}$)alkyl and —C(═O)—R$^{942}$; wherein R$^{941}$ is —COOH, —C(═O)NH$_2$, (C$_{3-7}$)cycloalkyl, Het, or phenyl optionally substituted with —OH, and R$^{942}$ is —O—(C$_{1-4}$)alkyl, —NH—(C$_{1-4}$)alkyl, phenyl, (C$_{3-7}$)cycloalkyl or Het, wherein said (C$_{3-7}$)cycloalkyl is optionally substituted with —COOH and wherein said Het is optionally substituted with one or two substituents each independently selected from (C$_{1-6}$)alkyl and —OH; or R$^{942}$ is (C$_{1-4}$)alkyl optionally substituted with —COOH, —NH$_2$, —NH(C$_{1-4}$)alkyl, —NH-Het, —N((C$_{1-4}$)alkyl)$_2$, or Het; wherein said Het is optionally substituted with one or two substituents each independently selected from —OH, —COOH and (C$_{1-6}$)alkyl optionally substituted with Het and wherein the (C$_{1-4}$)alkyl portion of said —NH(C$_{1-4}$)alkyl is optionally substituted with Het;
    d) —C(═O)N(R$^{95}$)R$^{96}$, wherein R$^{95}$ is H and R$^{96}$ is selected from (C$_{3-7}$)cycloalkyl, —SO$_2$—R$^{961}$ and —(C$_{1-4}$)alkyl-R$^{962}$, wherein R$^{961}$ is (C$_{1-4}$)alkyl, phenyl, (C$_{3-7}$)cycloalkyl, or —N((C$_{1-4}$)alkyl)$_2$; and R$^{962}$ is phenyl, —COOH, —N((C$_{1-4}$)alkyl)$_2$, or Het, wherein said phenyl is optionally substituted with —N((C$_{1-4}$)alkyl)$_2$ and said Het is optionally substituted with oxo; or R$^{95}$ and R$^{96}$, together with the N to which they are attached, are linked together to form a 5- or 6-membered heterocycle which is saturated or unsaturated and which is optionally contain from one to three further heteroatoms each independently selected from N, O and S; said heterocycle being optionally substituted with —COOH; and
    e) —O(C$_{1-4}$)alkyl optionally substituted with R$^{97}$ wherein R$^{97}$ is selected from —OH, —COOH, —C(═O)O—(C-4)alkyl-NH(C$_{1-4}$)alkyl, —C(═O)N(R$^{971}$)R$^{972}$, —NH$_2$, —NH—(C$_{3-7}$)cycloalkyl, —O-Het, and Het;
    provided that the carbon atom of —O—(C$_{1-4}$)alkyl- which is directly bonded to O is not also directly bonded to —OH, —NH$_2$ or —NH—(C$_{3-7}$)cycloalkyl;
    wherein each of said Het and the Het portion of said —O-Het is optionally substituted with one or two substituents each independently selected from halo, oxo, (C$_{1-4}$)alkyl, and —OH;
    and wherein R$^{971}$ is H or (C$_{1-4}$)alkyl and R$^{972}$ is selected from H, —OH, —NHC(═O)—(C$_{1-4}$)alkyl, —NHC(═O)—NH$_2$, (C$_{1-4}$)alkyl, (C$_{3-7}$)cycloalkyl, phenyl and Het, wherein said (C$_{1-4}$)alkyl is optionally substituted with —OH, —COOH, —N((C$_{1-4}$)alkyl)$_2$ or Het, provided that when R$^{972}$ is (C$_{1-4}$)alkyl, the carbon atom of (C$_{1-4}$)alkyl which is directly bonded to N is not also directly bonded to —OH;
    and wherein said (C$_{3-7}$)cycloalkyl is optionally substituted with —COOH, and wherein said phenyl is optionally substituted with —OH, —COOH, or —(C$_{2-4}$)alkenyl-COOH;
    or R$^{971}$ and R$^{972}$, together with the N to which they are attached, are linked together to form a 5- or 6-membered heterocycle which is saturated or unsaturated and which is optionally contain from one to three further heteroatoms each independently selected from N, O and S; said heterocycle being optionally substituted with (C$_{1-4}$)alkyl or —COOH;
    wherein Het is a 4,5- or 6-membered heterocycle or a 9- or 10-membered heterobicycle, each of which is saturated, unsaturated or aromatic and each of which containing from one to four heteroatoms each independently selected from N, O and S, wherein each said N heteroatom is, independently and where possible, exist in an oxidized state such that it is further bonded to an O atom to form an N-oxide group and wherein each said S heteroatom is, independently and where possible, exist in an oxidized state such that it is further bonded to one or two oxygen atoms to form the groups SO or SO$_2$.

Provided herein are compounds of Formula (II): Ar$^1$—X$^1$—W—Ar$^2$ (II); wherein Ar$^1$ is:
  (i) 5- or 6-membered aromatic heterocycle containing 1 to 4 heteroatoms selected from N, O or sS; said heterocycle optionally substituted with (C$_{1-4}$)alkyl, (C$_{3-7}$)cycloalkyl, (C$_{3-7}$)cycloalkyl-(C$_{1-3}$)alkyl-, wherein said alkyl, cycloalkyl or cycloalkylalkyl is monosubstituted with —OH; and/or phenyl when the heterocycle contains 1 to 3 N-atoms; in either instance, the said heterocycle is optionally substituted with: phenyl, phenylmethyl, 5- or 6-membered aromatic heterocycle, fused phenyl-unsaturated or saturated 5- or 6-membered carbocycle, fused phenyl-{unsaturated or saturated 5- or 6-membered carbocycle}methyl, or fused phenyl-5- or 6-membered aromatic heterocycle; each of said phenyl, phenylmethyl, aromatic heterocycle, fused phenyl-carbocycle, fused phenyl-(carbocycle)methyl or fused phenyl-aromatic heterocycle in turn is substituted optionally with 1 to 3 substituents selected independently from: (C$_{1-6}$)alkyl, (C$_{3-7}$)cycloalkyl, (C$_{3-7}$)cycloalkyl-(C$_{1-3}$)alkyl, (C$_{2-6}$)alkenyl, O—(C$_{1-4}$)alkyl, S—$(C_{1-4})$alkyl, halo, $CF_3$, $OCF_3$, OH, $NO_2$, CN, phenyl optionally substituted with $C_{1-6}$alkyl or nitro, phenylmethyl optionally substituted with $C_{1-6}$alkyl or nitro, $SO_2NH_2$, $SO_2$—$(C_{1-4})$alkyl, $C(O)NH_2$, $C(O)OR^1$, $NR^2R^3$, morpholino or 1-pyrrolyl, wherein $R^1$ is H or $(C_{1-4})$alkyl, and wherein $R^2$ and $R^3$ each independently is H or $(C_{1-4})$alkyl; wherein said substituents are sterically compatible; or (ii) unsaturated or saturated 5- or 6-membered carbocycle substituted with phenyl or naphthyl, said unsaturated or saturated carbocycle, or the phenyl or naphthyl optionally substituted with the same 1 to 3 substituents as defined for the substituents in section (i); or (iii) benzimidazole optionally N-substituted with phenyl or a fused phenyl-carbocycle as defined above;

X' is a valence bond, O, S, SO, $SO_2$, $NR^4$ or $CR^{4A}R^{4B}$ wherein $R^4$, $R^{4A}$ and $R^{4B}$ are each independently H or $(C_{1-4})$alkyl; and when X' is O, S, SO, $SO_2$ or $NR^4$: W is a divalent radical selected from:

(A) $(CR^5R^{5A})_{1-2}$—$C(Z^A)NR^6$ wherein $R^5$ and $R^{5A}$ each independently is H or $(C_{1-4})$alkyl, $R^6$ is H or $(C_{1-4})$alkyl, and $Z^A$ is oxo or thioxo;

(B) D-$C(Z^B)$ wherein D is $(C_{1-4})$alkylene, $(C_{1-4})$alkylene-O or $(C_{1-4})$alkylene-$NR^7$ wherein $R^7$ is H or $(C_{1-4})$alkyl, and $Z^B$ is oxo or thioxo;

(C) $CH_2C(Z^C)NR^{7A}(C_{1-4})$alkylene wherein $Z^C$ is oxo or thioxo and $R^{7A}$ is H or $(C_{1-4})$alkyl;

(D) $(C_{1-4})$alkylene-$NR^{7B}C(Z^D)NR^{7C}$ wherein $R^{7B}$ and $R^{7C}$ each independently is H or $(C_{1-4})$alkyl, and $Z^D$ is oxo or thioxo;

(E) $(C_{1-4})$alkylene optionally substituted with OH, or optionally disubstituted with OH when the $(C_{1-4})$alkylene contains 2 to 4 carbon atoms; $(C_{2-4})$alkenyl optionally substituted with halo; or cis- or trans-

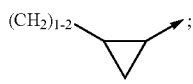

or (F) {$(C_{1-4})$alkylene}-O optionally substituted on the alkylene portion with OH;

(G) {$(C_{1-4})$alkylene}-$NR^8$ optionally substituted on the alkylene portion with OH, and $R^8$ is H or $(C_{1-4})$alkyl;

(H) $(C_{1-4})$alkylene-$C(Z^E)(C_{1-4})$alkylene wherein $Z^E$ is oxo or thioxo; or (I)

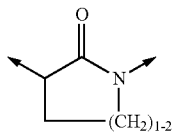

or (J) $(CR^5R^{5A})_{1-2}$—$NR^6$—$(CR^5R^{5A})_{1-2}$ wherein $R^5$ and $R^{5A}$ each independently is H or $(C_{1-4})$alkyl, $R^6$ is H or $(C_{1-4})$alkyl; and $Ar^2$ is:

(i) a phenyl or pyridinyl selected from the formulas

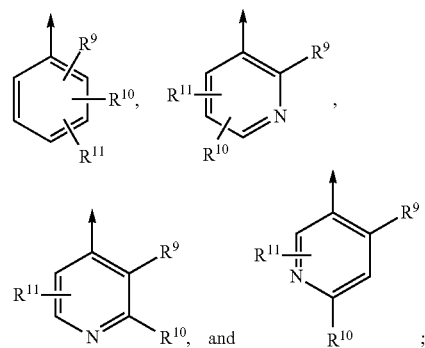

wherein $R^9$, $R^{10}$ and $R^{11}$ each independently represents: H, $(C_{1-6})$alkyl, $(C_{3-7})$cycloalkyl, $(C_{3-7})$cycloalkyl-$(C_{1-3})$alkyl, $(C_{2-6})$alkenyl, O—$(C_{1-6})$alkyl, S—$(C_{1-6})$alkyl, halo, $CF_3$, $OCF_3$, OH, $NO_2$, CN, —$NR^{N1}R^{N2}$, —$C(O)R^{21}$, —$(C_{1-3})$alkyl-$C(O)R^{21}$, —$C(O)OR^{22}$, —$(C_{1-3})$alkyl-$C(O)OR^{22}$, —$SO_2$—$(C_{1-3})$alkyl-$C(O)OR^{22}$, wherein $R^{21}$ is $(C_{1-4})$alkyl; $R^{22}$ is H or $(C_{1-4})$alkyl; $C(O)NH_2$, —$(C_{1-3})$alkyl-$C(O)NH_2$, $S(O)$—$(C_{1-4})$alkyl, $SO_2$—$(C_{1-4})$alkyl, $SO_2NH_2$, phenyl, phenylmethyl, phenyl-$SO_2$—, 2-, 3- or 4-pyridinyl, 1-pyrrolyl, whereby said phenyl, pyridinyl and pyrrolyl have one or more substituents selected from the group consisting of halo, $NO_2$, $C_{1-3}$-alkyl and $CF_3$; wherein the substituents $R^9$, $R^{10}$ and $R^{11}$ are sterically compatible; wherein $R^{N1}$, $R^{N2}$ each independently represent H or $(C_{1-6})$alkyl, whereby $R^{N1}$ and $R^{N2}$ is covalently bonded to each other to form together with the N-atom to which they are attached to a 4 to 7-membered heterocycle whereby the —$CH_2$-group at the position 4 of a 6 or 7-membered heterocycle is replaced by —O—, —S— or —$NR^{N3}$ wherein $R^{N3}$ represents H, —$C(O)OR^{22}$, $(C_{1-6})$alkyl, $(C_{3-7})$cycloalkyl or $(C_{3-7})$cycloalkyl-$(C_{1-3})$alkyl, wherein $R^{22}$ is H or $(C_{1-4})$alkyl; or (ii) $Ar^2$ is a fused phenyl-(saturated or unsaturated 5- or 6-membered carbocyclic ring optionally substituted with 1 to 3 substituents selected independently from $(C_{1-4})$alkyl, O—$(C_{1-4})$alkyl, S—$(C_{1-4})$alkyl, $NO_2$ or halo; or (iii) $Ar^2$ is a 5- or 6-membered aromatic heterocycle containing 1 to 4 heteroatoms selected from N, O or S, or a fused phenyl-5- or 6-membered heterocycle, said aromatic heterocycle or fused phenyl-heterocycle is optionally substituted with 1 to 3 substituents selected independently from $(C_{1-4})$alkyl, O—$(C_{1-4})$alkyl, S—$(C_{1-4})$alkyl, $NO_2$ or halo; or (iv) $Ar^2$ is phthalimido and W is $(C_{1-4})$alkylene.

Provided herein are compounds of Formula II wherein X' is a valence bond and W is a {$(C_{2-4})$alkenyl}$C(O)NR^{8A}$, cis- or trans-

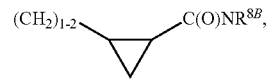

or cis- or trans-

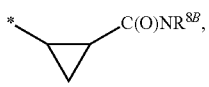

wherein $R^{8A}$ and $R^{8B}$ each is H or $(C_{1-4})$alkyl; or when X' is $CR^{4A}R^{4B}$ as defined above: W is selected from {$(C_{1-4})$alkylene}$C(O)NR^{8C}$, S-{$(C_{1-4})$alkylene}$C(O)NR^{8D}$, O—{$(C_{1-4})$-alkylene}$C(O)NR^{8E}$, or $NR^{8F}$—{$(C_{1-4})$alkylene}-$NR^{8G}$ wherein $R^{8C}$, $R^{8D}$, $R^{8E}$, $R^{8F}$ and $R^{8G}$ each independently is H or $(C_{1-4})$alkyl.

Provided herein are compounds of Formula II wherein $Ar^1$ is

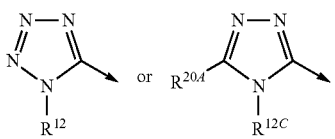

wherein $R^{12}$ is selected from the group consisting of

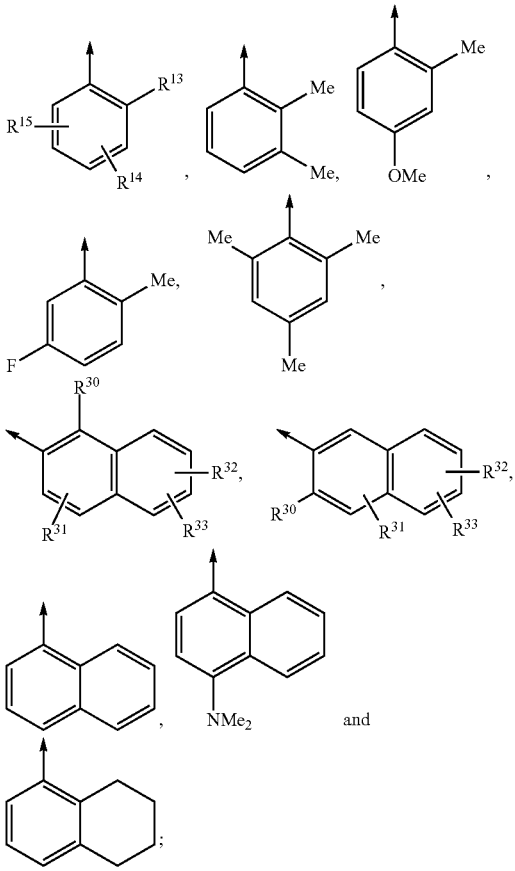

$R^{13}$ represents Cl, Br, COO$(C_{1-4})$alkyl and if $R^9$ is $NO_2$, Cl or Br, then $R^{13}$ also represent F or $CH_3$;

$R^{14}$, $R^{15}$, $R^{31}$, $R^{32}$, $R^{33}$ are each independently selected from the group consisting of H, $(C_{1-6})$alkyl, $(C_{3-7})$cycloalkyl, $(C_{3-7})$cycloalkyl-$(C_{1-3})$alkyl, $(C_{2-6})$alkenyl, O—$(C_{1-4})$alkyl, S—$(C_{1-4})$alkyl, halo, $CF_3$, $OCF_3$, OH, $NO_2$, CN, $SO_2NH_2$, $SO_2$—$(C_{1-4})$alkyl, $C(O)OR^1$ wherein $R^1$ is H or $(C_{1-4})$alkyl, or $NR^2R^3$ wherein $R^2$ and $R^3$ each independently is H or $(C_{1-4})$alkyl;

$R^{30}$ represents H, Cl, Br, COO$(C_{1-4})$alkyl;

$R^{12C}$ is a phenyl of formula

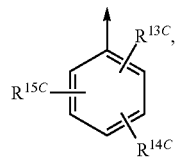

wherein $R^{13C}$, $R^{14C}$ and $R^{15C}$ each independently represents H, $(C_{1-6})$alkyl, $(C_{3-7})$cycloalkyl, $(C_{3-7})$cycloalkyl-$(C_{1-3})$alkyl, $(C_{2-6})$alkenyl, O—$(C_{1-4})$alkyl, S—$(C_{1-4})$alkyl, halo, $CF_3$, $OCF_3$, OH, $NO_2$, CN, $SO_2NH_2$, $SO_2$—$(C_{1-4})$alkyl, $C(O)OR^1$ wherein $R^1$ is H or $(C_{1-4})$alkyl, or $NR^2R^3$ wherein $R^2$ and $R^3$ each independently is H or $(C_{1-4})$alkyl; provided that at least one of $R^{13C}$, $R^{14C}$ and $R^{15C}$ is other than hydrogen;

or $R^{12C}$ is

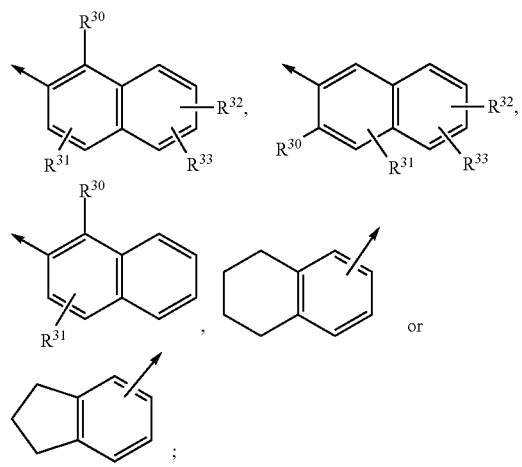

wherein $R^{30}$, $R^{31}$, $R^{32}$, $R^{33}$ are as defined hereinbefore; and $R^{20A}$ is H, $(C_{1-4})$alkyl, $(C_{3-7})$cycloalkyl or $(C_{3-7})$cycloalkyl-$(C_{1-3})$alkyl-, wherein said alkyl, cycloalkyl or cycloalkylalkyl is monosubstituted with —OH.

Provided herein are compounds of Formula II wherein X' is S or O.

Provided herein are compounds of Formula II wherein W is $CH_2C(O)NR^6$ wherein $R^6$ is H or $(C_{1-4})$alkyl.

Provided herein are compounds of Formula II wherein $Ar^2$ is:

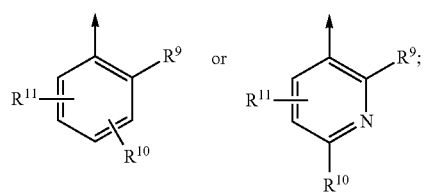

wherein $R^9$ is halo or $NO_2$; and if $R^{13}$ is Cl or Br, then $R^9$ also represents $(C_{1-3})$alkyl; $R^{10}$, $R^{11}$ are independently of each other selected from the group consisting of H, (C$_{1-6}$)alkyl, (C$_{3-7}$)Cycloalkyl, (C$_{3-7}$)Cycloalkyl-(C$_{1-3}$)alkyl, (C$_{2-6}$)alkenyl, O(C$_{1-6}$)alkyl, S(C$_{1-6}$)alkyl, halo, CF$_3$, OCF$_3$, OH, NO$_2$, CN, —NR$^{N1}$R$^{N2}$, —C(O)R$^{21}$, —(C$_{1-3}$)alkyl-C(O)R$^{21}$, —C(O)OR$^{22}$, —(C$_{1-3}$)alkyl-C(O)OR$^{22}$, —SO$_2$—(C$_{1-3}$)alkyl-C(O)OR$^{22}$, wherein R$^{21}$ is (C$_{1-4}$)alkyl and R$^{22}$ is H or (C$_{1-4}$)alkyl; —(C$_{1-3}$)alkyl-C(O)NH$_2$, C(O)NH$_2$, S(O)—(C$_{1-6}$)alkyl, —SO$_2$—(C$_{1-6}$)alkyl, —SO$_2$-phenyl, —SO$_2$—NH$_2$, phenyl, phenylmethyl, 2-, 3- or 4-pyridinyl, 1-pyrrolyl, whereby said phenyl, pyridinyl and pyrrolyl have one or more substituents selected from the group consisting of halo, NO$_2$, C$_{1-3}$-alkyl and CF$_3$.

Provided herein are compounds of Formula (III):

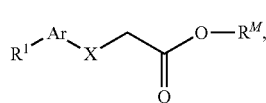

(III)

wherein
Ar is a 5-membered aromatic heterocycle containing 1 to 4 heteroatoms each independently selected from N, O and S; said heterocycle being optionally substituted at a substitutable position with R$^{Ar}$; wherein R$^{Ar}$ is H, (C$_{1-4}$)alkyl, CF$_3$ or (C$_{3-7}$)cycloalkyl, and wherein the groups X and R$^1$ are attached to positions on the Ar ring which are immediately adjacent to each other;
X is O or S;
R$^M$ is H, a pharmaceutically acceptable cation, substituted or unsubstituted (C$_{1-6}$)alkyl, substituted or unsubstituted aryl, substituted or unsubstituted heteroaryl, or a prodrug moiety; and
R$^1$ is a group of formula:

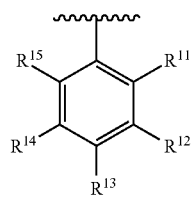

wherein:
R$^{11}$ is F, Cl, Br or I; and
R$^{12}$, R$^{13}$, R$^{14}$ and R$^{15}$ are each independently selected from H, F, Cl, Br, I, CN, CF$_3$, —OCF$_3$, (C$_{1-4}$)alkyl, —O—(C$_{1-4}$)alkyl, —N((C$_{1-4}$)alkyl)$_2$, (C$_{3-7}$)cycloalkyl and (C$_{3-7}$)cycloalkyl-(C$_{1-4}$)alkyl-; wherein said (C$_{3-7}$)cycloalkyl is optionally substituted with (C$_{1-4}$)alkyl; or
R$^{12}$ and R$^{13}$, R$^{13}$ and R$^{14}$, or R$^{14}$ and R$^{15}$ are linked, together with the carbon atoms to which they are attached, to form a five- or six-membered saturated, unsaturated or aromatic ring which optionally contains from one to three heteroatoms each independently selected from O, S and N, wherein the remaining of R$^{12}$, R$^{13}$, R$^{14}$ and R$^{15}$ are defined as hereinbefore.

Provided herein are compounds of Formula (IV): Ar$^1$—X'—W—C(O)—O—R$^M$ (IV)
wherein:
R$^M$ is H, a pharmaceutically acceptable cation, substituted or unsubstituted (C$_{1-6}$)alkyl, substituted or unsubstituted aryl, substituted or unsubstituted heteroaryl, or a prodrug moiety;

Ar$^1$ is:
(i) 5- or 6-membered aromatic heterocycle containing 1 to 4 heteroatoms selected from N, O or S; said heterocycle optionally substituted with (C$_{1-4}$)alkyl, (C$_{3-7}$) cycloalkyl, (C$_{3-7}$)cycloalkyl-(C$_{1-3}$)alkyl-, wherein said alkyl, cycloalkyl or cycloalkylalkyl is monosubstituted with —OH; and/or phenyl when the heterocycle contains 1 to 3 N-atoms; in either instance, the said heterocycle is optionally substituted with: phenyl, phenylmethyl, 5- or 6-membered aromatic heterocycle, fused phenyl-unsaturated or saturated 5- or 6-membered carbocycle, fused phenyl-{unsaturated or saturated 5- or 6-membered carbocycle)}methyl, or fused phenyl-5- or 6-membered aromatic heterocycle; each of said phenyl, phenylmethyl, aromatic heterocycle, fused phenyl-carbocycle, fused phenyl-(carbocycle)methyl or fused phenyl-aromatic heterocycle in turn is substituted optionally with 1 to 3 substituents selected independently from: (C$_{1-6}$) alkyl, (C$_{3-7}$)cycloalkyl, (C$_{3-7}$)cycloalkyl-(C$_{1-3}$)alkyl, (C$_{2-6}$)alkenyl, O—(C$_{1-4}$)alkyl, S—(C$_{1-4}$)alkyl, halo, CF$_3$, OCF$_3$, OH, NO$_2$, CN, phenyl optionally substituted with C$_{1-6}$alkyl or nitro, phenylmethyl optionally substituted with C$_{1-6}$alkyl or nitro, SO$_2$NH$_2$, SO$_2$—(C$_{1-4}$)alkyl, C(O)NH$_2$, C(O)OR$^1$, NR$^2$R$^3$, morpholino or 1-pyrrolyl, wherein R$^1$ is H or (C$_{1-4}$)alkyl, and wherein R$^2$ and R$^3$ each independently is H or (C$_{1-4}$)alkyl; wherein said substituents are sterically compatible; or
(ii) unsaturated or saturated 5- or 6-membered carbocycle substituted with phenyl or naphthyl, said unsaturated or saturated carbocycle, or the phenyl or naphthyl optionally substituted with the same 1 to 3 substituents as defined for the substituents in section (i); or
(iii) benzimidazole optionally N-substituted with phenyl or a fused phenyl-carbocycle as defined above;
X' is a valence bond, O, S, SO, SO$_2$, NR$^4$ or CR$^{4A}$R$^{4B}$, wherein R$^4$ is H or (C$_{1-4}$)alkyl; R$^{4A}$ and R$^{4B}$ are each independently H or (C$_{1-4}$)alkyl; and wherein when X' is O, S, SO, SO$_2$ or NR$^4$, then W is a divalent radical selected from:
(A) (CR$^5$R$^{5A}$)$_{1-2}$—C(Z$^A$)NR$^6$; wherein R$^5$ and R$^{5A}$ are each independently H or (C$_{1-4}$)alkyl; R$^6$ is H or (C$_{1-4}$)alkyl, and Z$^A$ is oxo or thioxo;
(B) D-C(Z$^B$); wherein D is (C$_{1-4}$)alkylene, (C$_{1-4}$)alkylene-O or (C$_{1-4}$)alkylene-NR$^7$; wherein R$^7$ is H or (C$_{1-4}$)alkyl; and Z$^B$ is oxo or thioxo;
(C) CH$_2$C(Z$^C$)NR$^{7A}$(C$_{1-4}$)alkylene; wherein Z$^C$ is oxo or thioxo; and R$^{7A}$ is H or (C$_{1-4}$)alkyl;
(D) (C$_{1-4}$)alkylene-NR$^{7B}$C(Z$^D$)NR$^{7C}$; wherein R$^{7B}$ and R$^{7C}$ are each independently H or (C$_{1-4}$)alkyl; and Z$^D$ is oxo or thioxo;
(E) (C$_{1-4}$)alkylene optionally substituted with OH, or optionally disubstituted with OH when the (C$_{1-4}$) alkylene contains 2 to 4 carbon atoms; (C$_{2-4}$)alkenyl optionally substituted with halo; or cis- or trans-

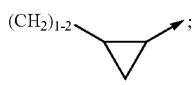

(F) {(C$_{1-4}$)alkylene}-O optionally substituted on the alkylene portion with OH;

(G) {(C$_{1-4}$)alkylene}-NR$^8$ optionally substituted on the alkylene portion with OH; wherein R$^8$ is H or (C$_{1-4}$)alkyl;

(H) (C$_{1-4}$)alkylene-C(Z$^E$)(C$_{1-4}$)alkylene; wherein Z$^E$ is oxo or thioxo;

(I)

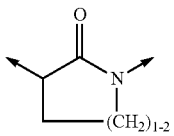

or (J) (CR$^5$R$^{5A}$)$_{1-2}$—NR$^6$—(CR$^5$R$^{5A}$)$_{1-2}$; wherein R$^5$ and R$^{5A}$ are each independently H or (C$_{1-4}$)alkyl; and R$^6$ is H or (C$_{1-4}$)alkyl.

Provided herein are compounds of Formula IV wherein X' is a valence bond, and W is {(C$_{2-4}$)alkenyl}C(O)NR$^{8A}$; cis- or trans-

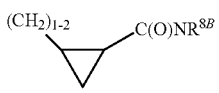

or cis- or trans-

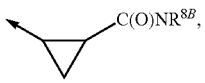

wherein R$^{8A}$ and R$^{8B}$ are each independently H or (C$_{1-4}$)alkyl. In other specific embodiments, X is CR$^{4A}$R$^{4B}$, and W is {(C$_{1-4}$)alkylene}C(O)NR$^{8C}$, S-{(C$_{1-4}$)alkylene}C(O)NR$^{8D}$, O-{(C$_{1-4}$)-alkylene}C(O)NR$^{8E}$, or NR$^{8F}$—{(C$_{1-4}$)alkylene}-NR$^{8G}$, wherein R$^{8C}$, R$^{8D}$, R$^{8E}$, R$^{8F}$ and R$^{8G}$ are each independently H or (C$_{1-4}$)alkyl.

Synthetic Procedures

In another aspect, methods for synthesizing a compound disclosed herein are provided. A compound disclosed herein is prepared by any of the methods described below. The procedures and examples below are intended to illustrate those methods. Neither the procedures nor the examples should be construed as limiting the invention in any way. A compound disclosed herein is also synthesized using standard synthetic techniques or using such methods in combination with methods described herein.

In some embodiments, the starting materials used for the synthesis of the compounds as described herein are obtained from commercial sources, such as Aldrich Chemical Co. (Milwaukee, Wis.), Sigma Chemical Co. (St. Louis, Mo.). In some embodiments, the starting materials are synthesized.

A compound disclosed herein, and other related compounds having different substituents is synthesized using any suitable technique, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3$^{rd}$ Ed., (Wiley 1999) (all of which are incorporated by reference for such disclosures). The various moieties found in the formulae as provided herein are obtained using any suitable method. The following synthetic methods serve as a guide for synthesizing a compound disclosed herein.

Formation of Covalent Linkages by Reaction of an Electrophile with a Nucleophile In some embodiments, a compound disclosed herein is modified using various electrophiles or nucleophiles to form new functional groups or substituents. The table below entitled "Examples of Covalent Linkages and Precursors Thereof" lists selected examples of covalent linkages and precursor functional groups. Precursor functional groups are shown as electrophilic groups and nucleophilic groups.

| Covalent Linkage Product | Electrophile | Nucleophile |
| --- | --- | --- |
| Carboxamides | Activated esters | Amines/anilines |
| Carboxamides | Acyl azides | Amines/anilines |
| Carboxamides | Acyl halides | Amines/anilines |
| Esters | Acyl halides | Alcohols/phenols |
| Esters | Acyl nitriles | Alcohols/phenols |
| Carboxamides | Acyl nitriles | Amines/anilines |
| Imines | Aldehydes | Amines/anilines |
| Hydrazones | Aldehydes or ketones | Hydrazines |
| Oximes | Aldehydes or ketones | Hydroxylamines |
| Alkyl amines | Alkyl halides | Amines/anilines |
| Esters | Alkyl halides | Carboxylic acids |
| Thioethers | Alkyl halides | Thiols |
| Ethers | Alkyl halides | Alcohols/phenols |
| Thioethers | Alkyl sulfonates | Thiols |
| Esters | Alkyl sulfonates | Carboxylic acids |
| Ethers | Alkyl sulfonates | Alcohols/phenols |
| Esters | Anhydrides | Alcohols/phenols |
| Carboxamides | Anhydrides | Amines/anilines |
| Thiophenols | Aryl halides | Thiols |
| Aryl amines | Aryl halides | Amines |
| Thioethers | Aziridines | Thiols |
| Boronate esters | Boronates | Glycols |
| Carboxamides | Carboxylic acids | Amines/anilines |
| Esters | Carboxylic acids | Alcohols |
| Hydrazines | Hydrazides | Carboxylic acids |
| N-acylureas or Anhydrides | Carbodiimides | Carboxylic acids |
| Esters | Diazoalkanes | Carboxylic acids |
| Thioethers | Epoxides | Thiols |
| Thioethers | Haloacetamides | Thiols |
| Ammotriazines | Halotriazines | Amines/anilines |
| Triazinyl ethers | Halotriazines | Alcohols/phenols |
| Amidines | Imido esters | Amines/anilines |
| Ureas | Isocyanates | Amines/anilines |
| Urethanes | Isocyanates | Alcohols/phenols |
| Thioureas | Isothiocyanates | Amines/anilines |
| Thioethers | Maleimides | Thiols |
| Phosphite esters | Phosphoramidites | Alcohols |
| Silyl ethers | Silyl halides | Alcohols |
| Alkyl amines | Sulfonate esters | Amines/anilines |
| Thioethers | Sulfonate esters | Thiols |
| Esters | Sulfonate esters | Carboxylic acids |
| Ethers | Sulfonate esters | Alcohols |
| Sulfonamides | Sulfonyl halides | Amines/anilines |
| Sulfonate esters | Sulfonyl halides | Phenols/alcohols |

Examples of Covalent Linkages and Precursors Thereof

Use of Protecting Groups

In some embodiments, it is necessary to protect reactive functional groups, for example hydroxy, amino, imino, thio or carboxy groups, where these are desired in the final product, to avoid their unwanted participation in the reactions. Protecting groups are used to block some or all reactive moieties and prevent such groups from participating in chemical reactions until the protective group is removed. It is preferred that each protective group be removable by a different means.

Protective groups that are cleaved under totally disparate reaction conditions fulfill the requirement of differential removal. In some embodiments, protective groups are removed by acid, base, hydrogenolysis, or combinations thereof. In some embodiments, groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. In some embodiments, carboxylic acid and hydroxy reactive moieties are blocked with base labile groups such as, but not limited to, methyl, ethyl, and acetyl in the presence of amines blocked with acid labile groups such as t-butyl carbamate or with carbamates that are both acid and base stable but hydrolytically removable.

In some embodiments, carboxylic acid and hydroxy reactive moieties are blocked with hydrolytically removable protective groups such as the benzyl group. In some embodiments, amine groups capable of hydrogen bonding with acids are blocked with base labile groups such as Fmoc.

In some embodiments, carboxylic acid reactive moieties are protected by conversion to simple ester compounds as exemplified herein. In some embodiments, carboxylic acid reactive moieties are blocked with oxidatively-removable protective groups such as 2,4-dimethoxybenzyl, while co-existing amino groups are blocked with fluoride labile silyl carbamates.

In some embodiments, allyl blocking groups are used in the presence of acid- and base-protecting groups since the former are stable. In some embodiments, allyl blocking groups are subsequently removed by metal or pi-acid catalysts. For example, an allyl-blocked carboxylic acid is deprotected with a Pd-catalyzed reaction in the presence of acid labile t-butyl carbamate or base-labile acetate amine protecting groups.

In some embodiments, the protecting group is a resin to which a compound or intermediate is attached. In certain instances, as long as the residue is attached to the resin, the functional group is blocked and cannot react. Once released from the resin, the functional group is available to react.

In some embodiments, the protecting group is:

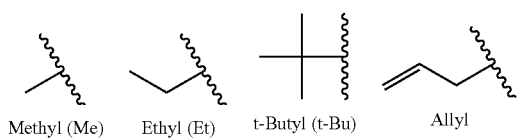

Methyl (Me)   Ethyl (Et)   t-Butyl (t-Bu)   Allyl

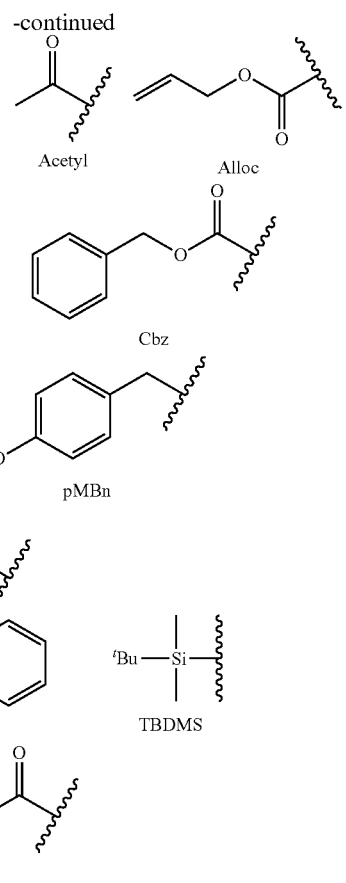

Benzyl (Bn)   Acetyl   Alloc

Boc   Cbz

Trityl   pMBn

Fmoc   TBDMS

Teoc

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosures.

Preparation of Compounds

General methods for preparing a compound of Formula (I), wherein Y is halo (e.g. Cl, Br or I), P is a protecting group, $R^1$, $R^2$, $R^3$, $R^4$, $R^5$, $R^6$, $R^7$, Ar, and X are as defined herein and $R^{4a}$ is a precursor of $R^4$ (or identical to $R^4$), are described in Scheme 1.

Scheme 1: General method for the synthesis of compound of Formula (I)

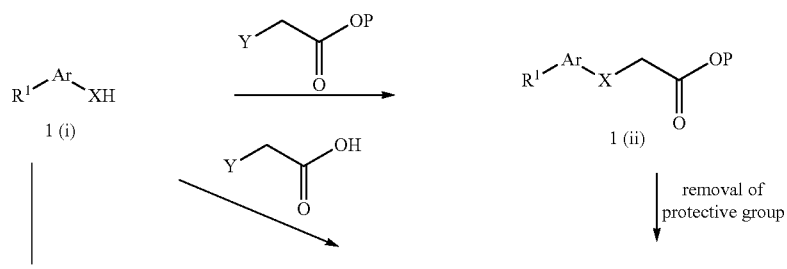

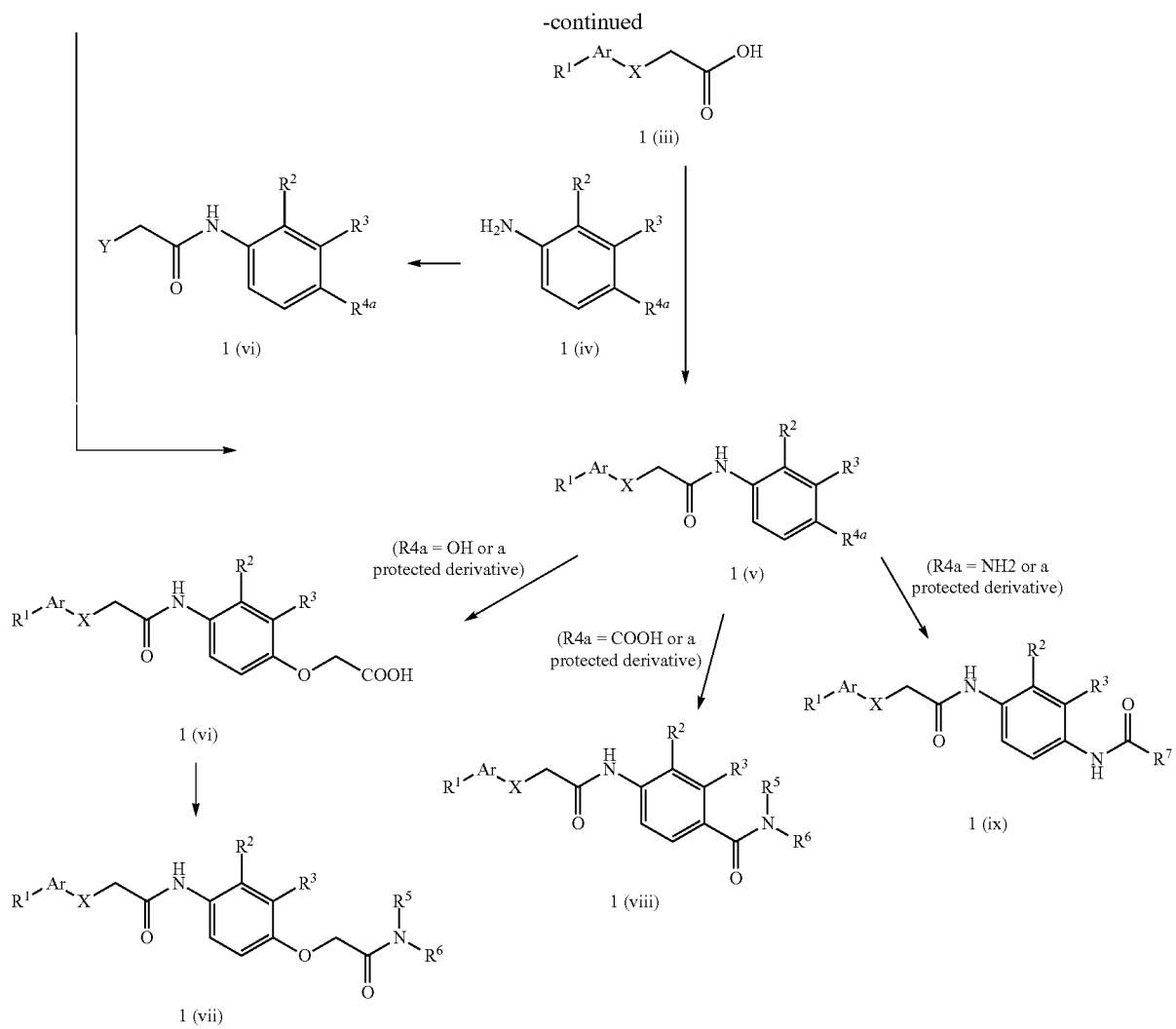

In some embodiments, thiol or alcohol 1(i) is alkylated with an α-haloacetic acid ester in the presence of a base to give 1(ii), which is transformed to acid 1(iii) after hydrolysis of the ester protecting group.

Alternatively, in some embodiments, 1(iii) is obtained directly by alkylation with α-haloacetic acid. In some embodiments, the reaction of acid 1(iii) with aniline 1(iv) provides amide 1(v) using the standard methods for preparing amides.

Alternatively, in some embodiments, amide 1(v) is obtained by the alkylation of 1(i) with 1(vi), which is readily available from aniline 1(iv) and α-haloacetyl chloride or bromide.

In some embodiments, amide 1(v) is transformed to a compound of Formula (I), if $R^{4a}$ is different from $R^4$, using methods known to the skilled in the art. In some embodiments, when $R^{4a}$ is —OH, or a protected form thereof, the group $R^{4a}$ is transformed to an —OCH$_2$COOH group by alkylation with an α-haloacetic ester fragment, followed by deprotection of the ester, to give compound 1 (vi). Coupling of the acid with amines of the formula HN(R$^5$)R$^6$, using methods well known in the art, provide compounds of general Formula 1(vii). In some embodiments, when $R^{4a}$ is —COOH or a protected form thereof, the group $R^{4a}$ is transformed to a group of formula —CON(R$^5$)R$^6$ by coupling with amines of the formula HN(R$^5$)R$^6$ to provide compounds of general Formula 1(viii). In some embodiments, when $R^{4a}$ is NH$_2$, or a protected form thereof, the group $R^{4a}$ is transformed to a group of formula —NH(C=O)R$^7$ by well known acylation procedures, to give compounds of general Formula 1(ix). In addition, protecting group removal, alkylation, coupling, amide formation or functional group modifications are contemplated, to carry out other transformations of compound 1(v) to other compounds of Formula (I).

In some embodiments, anilines (e.g., 1(iv)) are either commercially available. In some embodiments, an aniline (e.g., 1(iv)) is prepared according to any suitable method. By way of non-limiting example, substituted anilines 2(ii) and 2(iii), wherein Y is halo (e.g. Br or I), $R^2$, $R^3$, $R^9$, $R^{41}$ and $R^{42}$ are as defined herein and $R^{9a}$ and $R^{41a}$ are precursors of (or identical to) $R^9$ and $R^{41}$, respectively, are prepared according to Scheme 2.

Scheme 2: Synthesis of substituted anilines

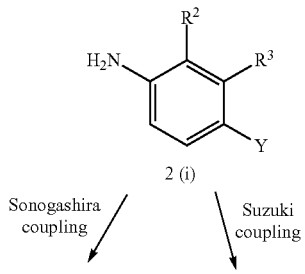

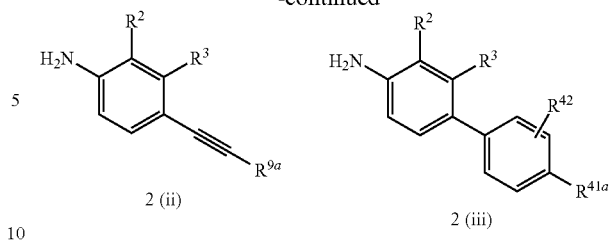

In some embodiments, 4-bromo or 4-iodoaniline 2(i) is transformed to anilines 2(ii) or 2(iii) using the typical conditions of the Sonogashira reaction or the Suzuki coupling.

The preparation of compounds of Formula (I) wherein Ar is tetrazole, 1,2,4-triazole, imidazole or 1,2,3-triazole and $R^{11}$, $R^{12}$, $R^{13}$, $R^{14}$, $R^{15}$ and $R^{Ar}$ are as defined herein is described in Scheme 3.

Scheme 3: Synthesis of tetrazole, 1,2,4-triazole, imidazole and 1,2,3-triazole derivatives

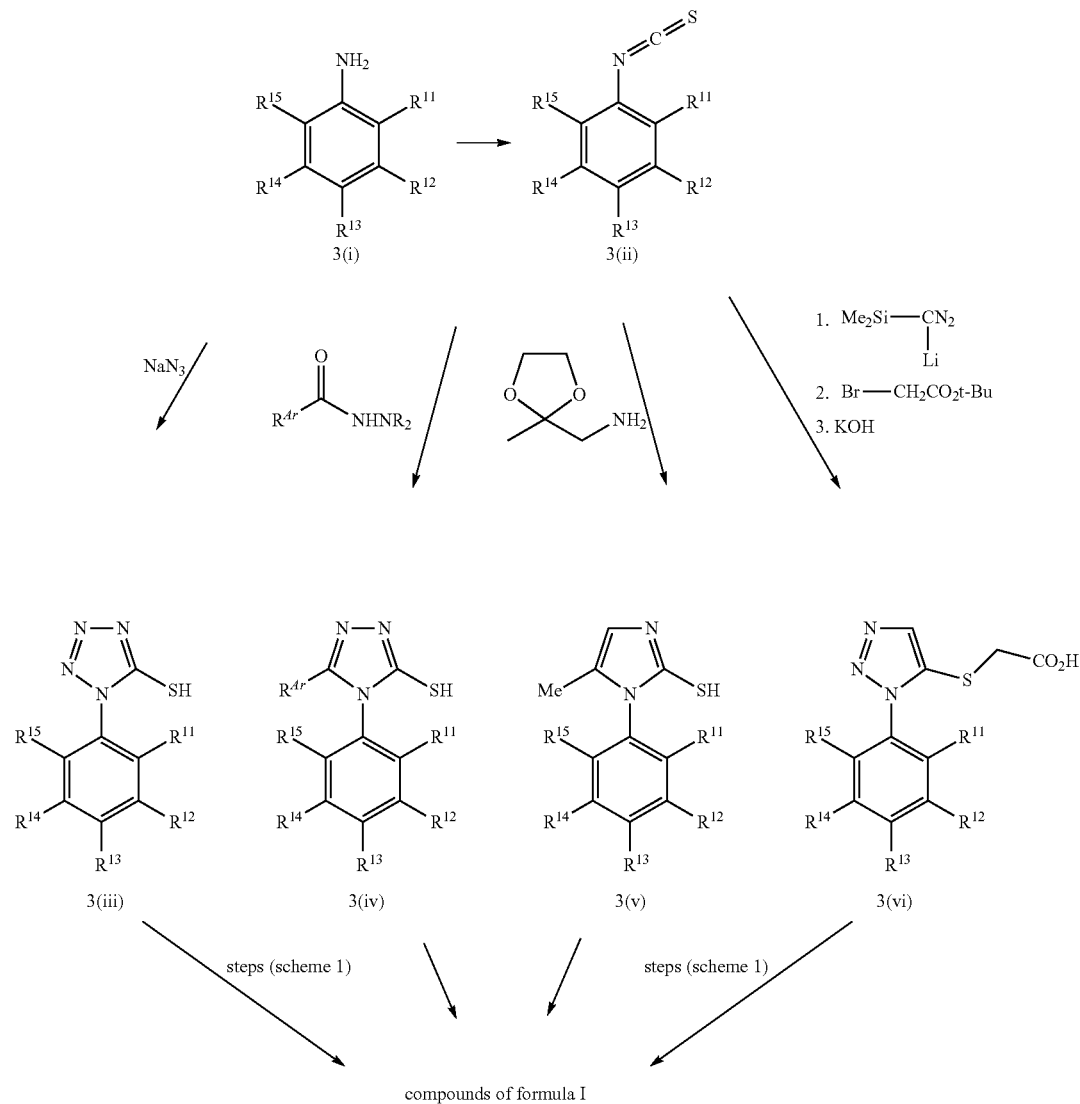

In some embodiments, isocyanate 3(ii) is purchased from a commercial supplier. In some embodiments, isocyanate 3(ii) is prepared by any suitable method from aniline 3(i).

In some embodiments, tetrazole 3(iii) is prepared by reacting isocyanate 3(ii) with sodium azide.

In some embodiments, triazole 3(iv) is obtained from the condensation of isocyanate 3(ii) with acylhydrazide, followed by treatment with base or acid.

In some embodiments, imidazole 3(v) is obtained from 3(ii) by treatment with 1-amino-2,2-ethylenedioxypropane.

In some embodiments, triazole 3(vi) is prepared by reacting the lithium salt of trimethylsilyldiazomethane with 3(ii) followed by the alkylation with tert-butyl bromoacetate and potassium hydroxide treatment.

Finally, in some embodiments, the compounds of Formula (I) are obtained from 3(iii), 3(iv), 3(v) and 3(vi) using the steps described in Scheme 1.

The preparation of compounds of Formula (I) wherein Ar is thiazole or thiadiazole, P is a protecting group and $R^{11}$, $R^{12}$, $R^{13}$, $R^{14}$ and $R^{15}$ are as defined herein is described in Scheme 4.

Scheme 4: Preparation of thiazole and thiadiazole derivatives

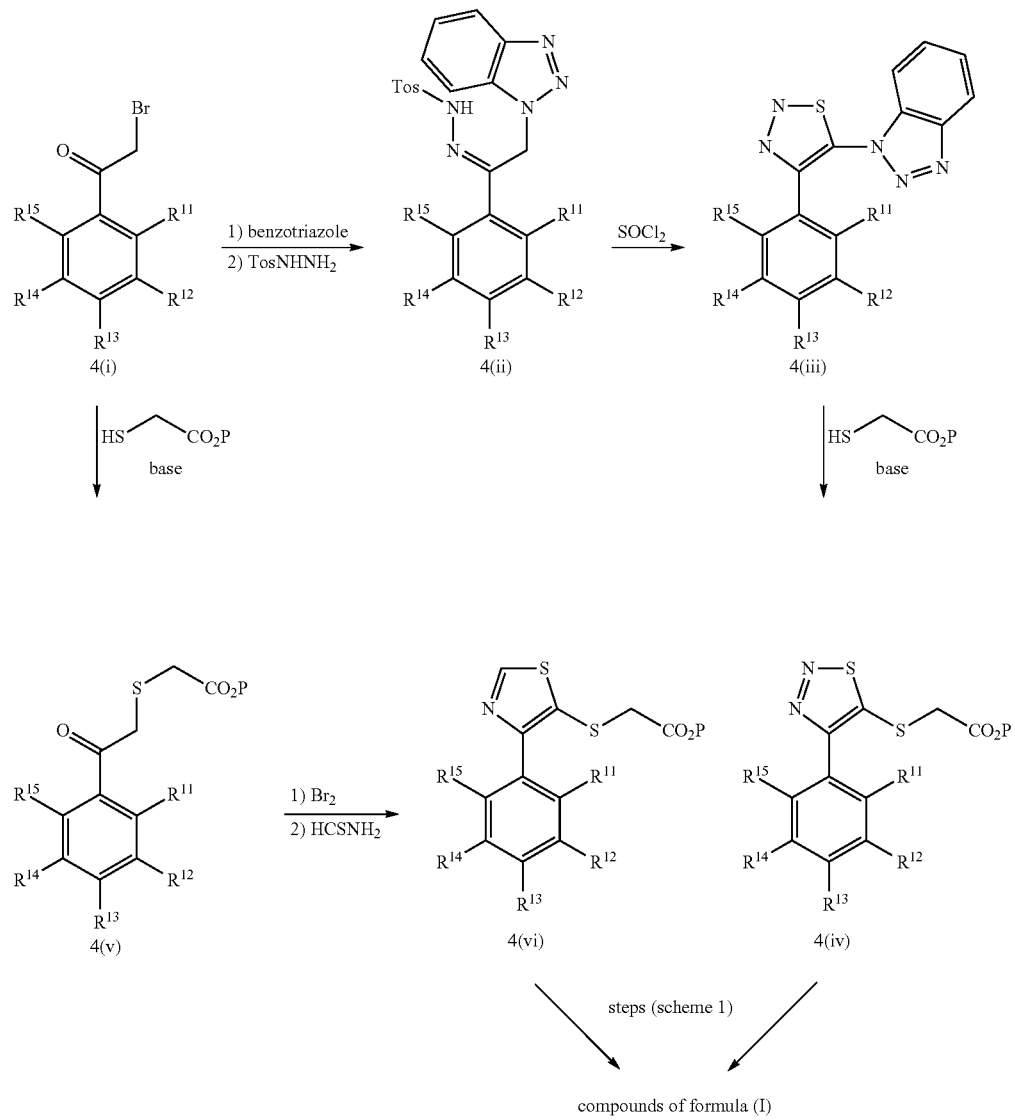

In some embodiments, the reaction of bromomethylketone 4(i) with benzotriazole followed with the treatment with p-toluenesulfonyl hydrazide gives intermediate 4(ii).

In some embodiments, the thiadiazole 4(iii) is prepared from 4(ii) by contacting it with thionyl chloride.

In some embodiments, contacting 4(iii) with thioglycolate yields 4(iv) and finally a compound of Formula (I) using the sequence described in Scheme 1.

In some embodiments, the bromomethylketone 4(i) is transformed to sulfide 4(v) by reacting it with thioglycolate in the presence of a base.

In some embodiments, the bromination of 4(v), followed by the treatment with thioformamide, gives 4(vi). In some embodiments, 4(vi) is transformed to a compound of Formula (I) using the sequence described in Scheme 1.

The preparation of compounds of Formula (I) wherein Ar is pyrazole, P is a protecting group, and $R^{11}$, $R^{12}$, $R^{13}$, $R^{14}$ and $R^{15}$ are as defined herein is described in Schemes 5-7.

Scheme 5: Preparation of pyrazole derivatives (method 1)

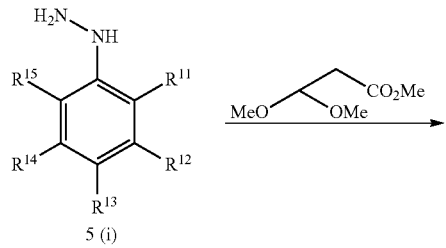

5 (i)

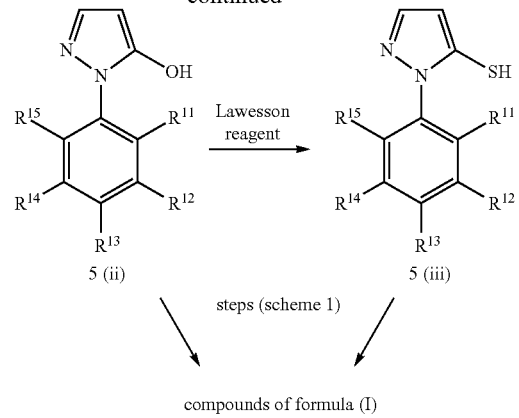

In some embodiments, pyrazole 5(ii) is obtained by reacting hydrazine 5(i) with methyl 3,3-dimethoxypropionate.

In some embodiments, hydroxypyrazole 5(ii) is transformed to the corresponding thiol derivative 5(iii) with the Lawesson reagent.

In some embodiments, pyrazole derivatives 5(ii) and 5(iii) are converted to compounds of Formula (I) by using the sequence described in Scheme 1.

Scheme 6: Preparation of pyrazole derivatives (method 2)

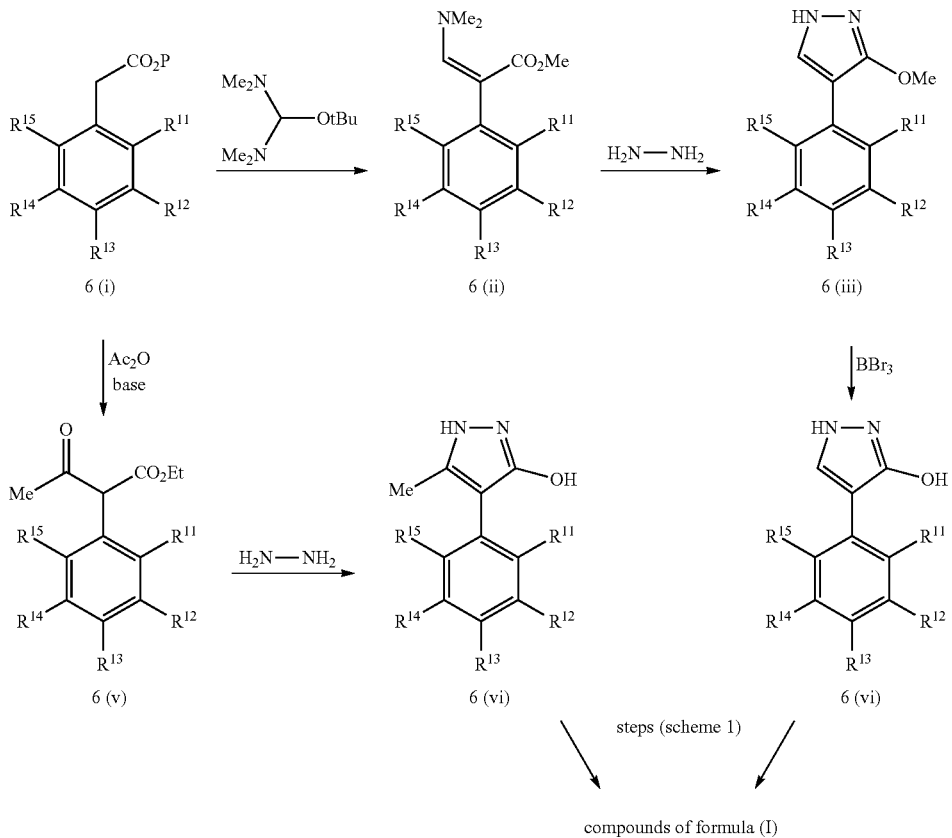

In some embodiments, the pyrazole derivatives 6(iv) and 6(vi) are obtained starting with phenylacetate 6(i). In some embodiments, the reaction of 6(i) with the appropriate electrophile, tert-butoxybis(dimethylamino)methane or acetic anhydride, yields intermediates 6(ii) and 6(v). In some embodiments, 6(ii) and 6(v) are transformed to pyrazoles 6(iii) and 6(vi) respectively upon treatment with hydrazine.

In some embodiments, the methyl ether derivative 6(iii) is transformed to the corresponding hydroxypyrazole 6(iv).

In some embodiments, using the steps described in Scheme 1, 6(iv) and 6(vi) are converted to compounds of Formula (I).

Further Forms
Isomers

In some embodiments, a compound disclosed herein exists as geometric isomers. In some embodiments, a compound disclosed herein possesses one or more double bonds. The compounds presented herein include all cis, trans, syn, anti, entgegen (E), and zusammen (Z) isomers as well as the corresponding mixtures thereof.

In some embodiments, compounds disclosed herein exist as tautomers. A compound disclosed herein includes all possible tautomers within the formulas described herein. In some Scheme 7: Preparation of pyrazole derivatives (method 3)

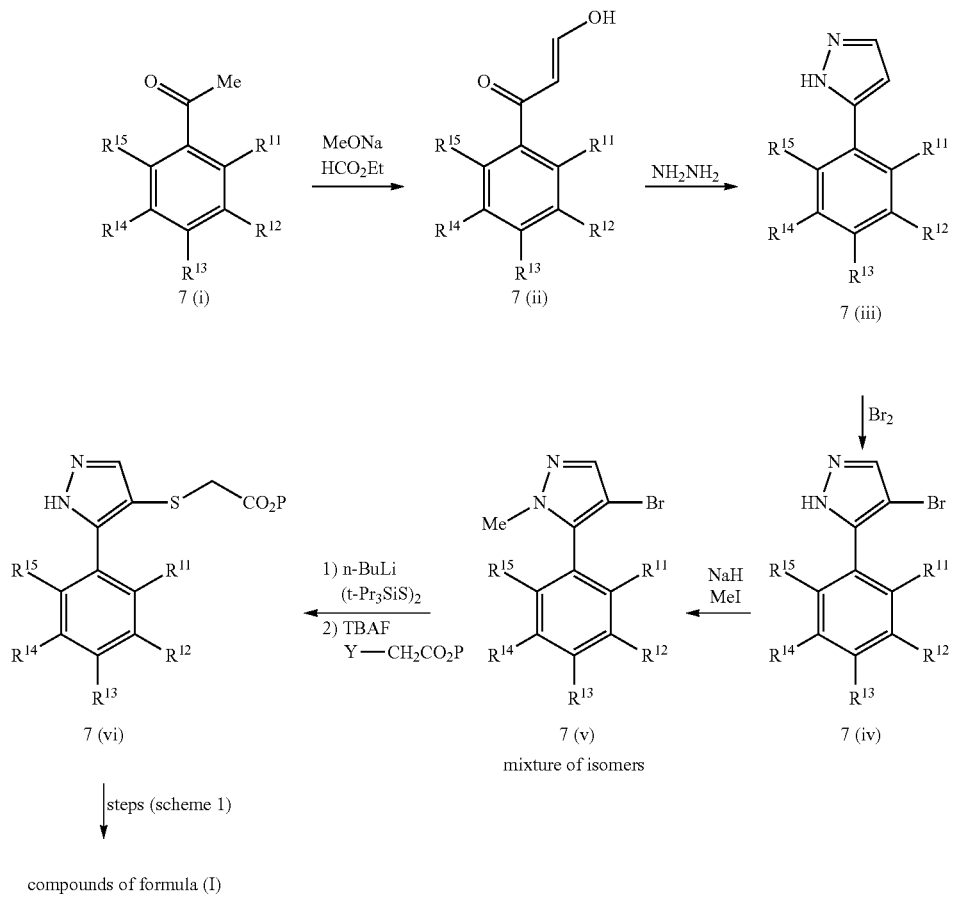

In some embodiments, pyrazole 7(ii) is obtained from the Claisen condensation of acetophenone 7(i) with ethyl formate in the presence of a base such as sodium methoxide. In some embodiments, pyrazole 7(iii) is obtained by condensating 7(ii) with hydrazine.

In some embodiments, pyrazole 7(iii) is converted to the bromo derivative 7(iv) upon treatment with bromine.

In some embodiments, pyrazole 7(iv) is transformed to a mixture of isomers (7(v) and isomer), which upon treatment with n-butyl lithium in the presence of $(^iPr_3Si—S)_2$, followed by the reaction with tetrabutylammonium fluoride in the presence of α-haloacetic acid ester is converted to 7(vi).

In some embodiments, using the sequence of steps described in Scheme 1, 7(vi) is be transformed to compounds of Formula (I).

embodiments, a compound disclosed herein possesses one or more chiral centers. In some embodiments, each center exists in the R or S configuration. A compound disclosed herein includes all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein.

In some embodiments, a compound disclosed herein is prepared as their individual stereoisomers by reacting a racemic mixture of the compound with an optically active resolving agent to form a pair of diastereoisomeric compounds, separating the diastereomers and recovering the optically pure enantiomers. In some embodiments, resolution of enantiomers is carried out using covalent diastereomeric derivatives of a compound disclosed herein. In some embodiments, resolution of enantiomers is carried out using dissociable complexes (e.g., crystalline diastereomeric salts). In certain instances, diastereomers have distinct physical properties (e.g., melting points, boiling points, solubilities, reactivity, etc.). In some embodiments, diastereomers are separated by taking advantage of these dissimilarities. In some embodiments, diastereomers are separated by chiral chromatography, or preferably, by separation/resolution techniques based upon differences in solubility. The optically pure enantiomer is then recovered, along with the resolving agent, by any practical means that would not result in racemization.

Labeled Compounds

In some embodiments, a compound disclosed herein exists in its isotopically-labeled forms. The invention provides for methods of treating diseases by administering such isotopically-labeled compounds. The invention further provides for methods of treating diseases by administering such isotopically-labeled compounds as pharmaceutical compositions. Thus, compounds of Formula I also include isotopically-labeled compounds, which are identical to those recited herein, but for the fact that one or more atoms are replaced by an atom having an atomic mass or mass number different from the atomic mass or mass number usually found in nature. Isotopes for use with a method or compound disclosed herein include, but are not limited to, include isotopes of hydrogen, carbon, nitrogen, oxygen, phosphorous, sulfur, fluorine and chloride, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. A compound disclosed herein, and the metabolites, pharmaceutically acceptable salts, esters, prodrugs, solvate, hydrates or derivatives thereof which contain the aforementioned isotopes and/or other isotopes of other atoms are within the scope of this invention. Certain isotopically-labeled compounds, for example those into which radioactive isotopes such as $^3$H and $^{14}$C are incorporated, are useful in drug and/or substrate tissue distribution assays. Tritiated, i.e., $^3$H and carbon-14, i.e., $^{14}$C, isotopes are particularly preferred for their ease of preparation and detectability. In some embodiments, substitution with heavy isotopes (e.g., deuterium, i.e., $^2$H) is utilized with a method or compound disclosed herein. In certain instances, substitution with heavy isotopes affords certain therapeutic advantages resulting from greater metabolic stability, for example increased in vivo half-life or reduced dosage requirements. In some embodiments, a compound, pharmaceutically acceptable salt, ester, prodrug, solvate, hydrate or derivative thereof is isotopically labeled by substituting a readily available isotopically labeled reagent for a non-isotopically labeled reagent in any procedure disclosed herein.

In some embodiments, a compound described herein is labeled by other means, including, but not limited to, the use of chromophores or fluorescent moieties, bioluminescent labels, or chemiluminescent labels.

Metabolites

In some embodiments, a compound disclosed herein exists as a metabolite. The invention provides for methods of treating diseases by administering such metabolites. The invention further provides for methods of treating diseases by administering such metabolites as pharmaceutical compositions.

In some embodiments, a compound disclosed herein is metabolized by a variety of metabolic mechanisms, such as hydrolysis, oxidation, glycolysis, phosphorylation, alkylation, dehalogenation, or combinations thereof.

Pharmaceutically Acceptable Salts

In some embodiments, a compound disclosed herein exists as a pharmaceutically acceptable salt. The invention provides for methods of treating diseases by administering such pharmaceutically acceptable salts. The invention further provides for methods of treating diseases by administering such pharmaceutically acceptable salts as pharmaceutical compositions.

In some embodiments, a compound disclosed herein possesses an acidic or basic group. In some embodiments, a compound disclosed herein that possesses an acidic or basic group reacts with any of a number of inorganic or organic bases, and inorganic and organic acids, to form a pharmaceutically acceptable salt. In some embodiments, a salt is prepared in situ during the final isolation and purification of the compounds of the invention, or by separately reacting a purified compound in its free form with a suitable acid or base, and isolating the salt thus formed.

Examples of pharmaceutically acceptable salts include those salts prepared by reaction of a compound disclosed herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate. metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate and xylenesulfonate.

Further, a compound disclosed herein is optionally prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, Q-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. Other acids, such as oxalic, while not in themselves pharmaceutically acceptable, are optionally employed in the preparation of salts useful as intermediates in obtaining the compounds of the invention and their pharmaceutically acceptable acid addition salts.

In some embodiments, a compound disclosed herein which comprises a free acid group reacts with a suitable base, such as the hydroxide, carbonate, bicarbonate, sulfate, of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Illustrative examples of bases include sodium hydroxide, potassium hydroxide, choline hydroxide, sodium carbonate, $N^+(C_{1-4} \text{ alkyl})_4$, and the like. Representative organic amines useful for the formation of base addition salts include ethylamine, diethylamine, ethylenediamine, ethanolamine, diethanolamine, piperazine and the like. It should be understood that a compound disclosed herein also includes the quaternization of any basic nitrogen-containing groups they contain. In some embodiments, water or oil-soluble or dispersible products are obtained by such quaternization. A compound disclosed herein is optionally prepared as pharmaceutically acceptable salts formed when an acidic proton present in the parent compound either is replaced by a metal ion, for example an alkali metal ion, an alkaline earth ion, or an aluminum ion; or coordinates with an organic base. In some embodiments, base addition salts are also prepared by reacting the free acid form of a compound disclosed herein with a pharmaceutically acceptable inorganic or organic base, including, but not limited to organic bases such as ethanolamine, diethanolamine, triethanolamine, tromethamine, N-methylglucamine, and the like and inorganic bases such as aluminum hydroxide, calcium hydroxide, potassium hydroxide, sodium carbonate, sodium hydroxide, and the like. In addition, the salt forms of the disclosed compounds are optionally prepared using salts of the starting materials or intermediates.

Solvates

In some embodiments, a compound disclosed herein exists as a solvate. The invention provides for methods of treating diseases by administering such solvates. The invention further provides for methods of treating diseases by administering such solvates as pharmaceutical compositions.

In certain instances, solvates contain either stoichiometric or non-stoichiometric amounts of a solvent. In some embodiments, a solvate is formed during the process of crystallization with pharmaceutically acceptable solvents such as water, ethanol, and the like. Hydrates are formed when the solvent is water, or alcoholates are formed when the solvent is alcohol. In some embodiments, a solvate of a compound disclosed herein is prepared or formed during the processes described herein. By way of example only, hydrates of a compound disclosed herein are conveniently prepared by recrystallization from an aqueous/organic solvent mixture, using organic solvents including, but not limited to, dioxane, tetrahydrofuran or methanol. In some embodiments, a compound provided herein exists in unsolvated as well as solvated forms. In general, the solvated forms are considered equivalent to the unsolvated forms for the purposes of the compounds and methods provided herein.

Polymorphs

In some embodiments, a compound disclosed herein exists as a polymorph. The invention provides for methods of treating diseases by administering such polymorphs. The invention further provides for methods of treating diseases by administering such polymorphs as pharmaceutical compositions.

Thus, a compound disclosed herein includes all crystalline forms, known as polymorphs. Polymorphs include the different crystal packing arrangements of the same elemental composition of a compound. In certain instances, polymorphs have different X-ray diffraction patterns, infrared spectra, melting points, density, hardness, crystal shape, optical and electrical properties, stability, and solubility. In certain instances, varying the recrystallization solvent, rate of crystallization, storage temperature, or a combination thereof results in a single crystal form dominating.

Prodrugs

In some embodiments, a compound disclosed herein exists as a prodrug. The invention provides for methods of treating diseases by administering such prodrugs. The invention further provides for methods of treating diseases by administering such prodrugs as pharmaceutical compositions.

As used herein, a "prodrugs" is a drug precursor that, following administration to a subject and subsequent absorption, is converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated.

In certain instances, prodrugs are useful as they easier to administer than the parent drug. In certain instances, a prodrug is bioavailable by oral administration whereas the parent is not. In some embodiments, a prodrug has improved solubility in pharmaceutical compositions over the parent drug. An example, without limitation, of a prodrug would be a compound as described herein which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug is a short peptide (polyamino acid) bonded to an acid group where the peptide is metabolized to reveal the active moiety.

Various forms of prodrugs include those found, for example in Bundgaard, "Design and Application of Prodrugs" in *A Textbook of Drug Design and Development*, Krosgaard-Larsen and Bundgaard, Ed., 1991, Chapter 5, 113-191, which is incorporated herein by reference for such disclosures.

In some embodiments, prodrugs are designed as reversible drug derivatives, for use as modifiers to enhance drug transport to site-specific tissues. The design of prodrugs to date has been to increase the effective water solubility of the therapeutic compound for targeting to regions where water is the principal solvent.

Additionally, prodrug derivatives of a compound disclosed herein are prepared by methods such as those described in Saulnier et al., *Bioorganic and Medicinal Chemistry Letters*, 1994, 4, 1985). By way of example only, appropriate prodrugs are prepared by reacting a non-derivatized compound with a suitable carbamylating agent, such as, but not limited to, 1,1-acyloxyalkylcarbanochloridate, para-nitrophenyl carbonate, or the like. Prodrug forms of a compound disclosed herein, wherein the prodrug is metabolized in vivo to produce a derivative as set forth herein, are included within the scope of the claims. In some embodiments, some of the herein-described compounds are prodrugs for another derivative or active compound.

In some embodiments, prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present invention. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e.g., two, three or four) nucleic acid residues is covalently joined to a compound of the present invention.

Pharmaceutically acceptable prodrugs of a compound disclosed herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. In some embodiments, compounds having free amino, amido, hydroxy or carboxylic groups are converted into prodrugs. For instance, free carboxyl groups are derivatized as amides or alkyl esters. In some embodiments, a prodrug moiety incorporates groups including but not limited to ether, amine and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters and disulfide containing esters; ethers, amides, carbamates, hemisuccinates, dimethylaminoacetates and phosphoryloxymethyloxycarbonyls, as outlined in *Advanced Drug Delivery Reviews* 1996, 19, 115.

Amine derived prodrugs include, but are not limited to the following groups and combinations of groups:

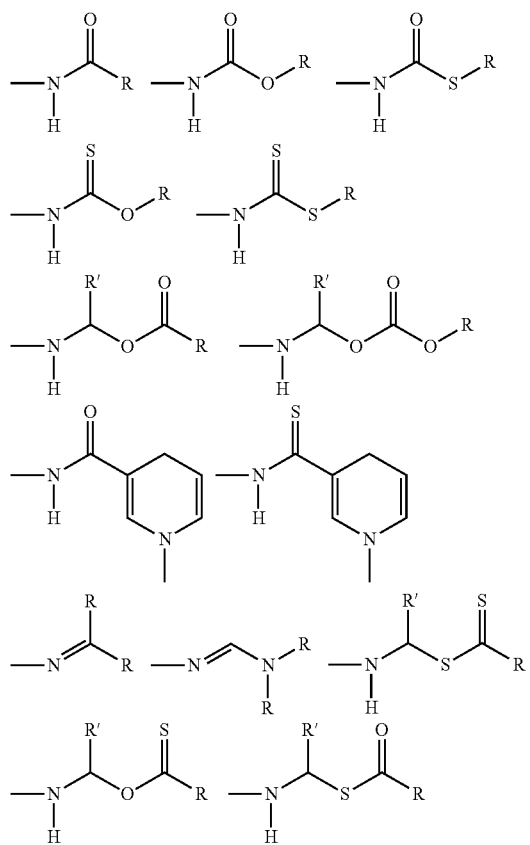

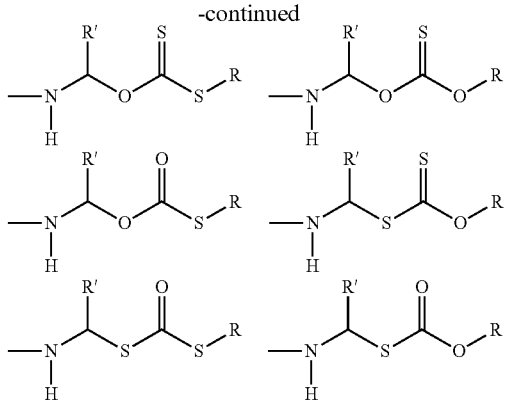

as well as sulfonamides and phosphonamides.

In certain instances, sites on any aromatic ring portions are susceptible to various metabolic reactions. In some embodiments, incorporation of appropriate substituents on the aromatic ring structures reduces, minimizes or eliminates this metabolic pathway.

Pharmaceutical Compositions

Described herein are pharmaceutical compositions. In some embodiments, the pharmaceutical compositions comprise an effective amount of a compound of Formula I, or a metabolite, pharmaceutically acceptable salt, ester, prodrug, solvate, hydrate or derivative thereof. In some embodiments, the pharmaceutical compositions comprise an effective amount of a compound Formula I, or a metabolite, pharmaceutically acceptable salt, ester, prodrug, solvate, hydrate or derivative thereof and at least one pharmaceutically acceptable carrier. In some embodiments the pharmaceutical compositions are for the treatment of disorders. In some embodiments the pharmaceutical compositions are for the treatment of disorders in a mammal. In some embodiments the pharmaceutical compositions are for the treatment of disorders in a human.

Formulations

A compound or composition described herein is administered either alone or in combination with pharmaceutically acceptable carriers, excipients or diluents, in a pharmaceutical composition, according to standard pharmaceutical practice. Administration of a compound or composition described herein is effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration. In some embodiments, the most suitable route depends upon the condition and disorder of the recipient. By way of example only, a compound disclosed herein is administered locally to the area in need of treatment by local infusion during surgery, topical application (e.g., as a cream or ointment), injection (e.g., directly into the site of a diseased tissue or organ), catheter, or implant.

In some embodiments, a formulation suitable for oral administration is presented as discrete units such as capsules, cachets or tablets each containing a predetermined amount of a compound or composition disclosed herein; as a powder or granules; as a solution or a suspension in an aqueous liquid or a non-aqueous liquid; or as an oil-in-water liquid emulsion or a water-in-oil liquid emulsion. In some embodiments, a compound or composition disclosed herein is presented as a bolus, electuary or paste.

Pharmaceutical preparations for oral administration include tablets, solutions, suspension, push-fit capsules made of gelatin, as well as soft, sealed capsules made of gelatin and a plasticizer, such as glycerol or sorbitol. In some embodiments, dye or pigment is added to an oral dosage form for identification or to characterize different doses.

In some embodiments, a tablet is made by compression or molding, optionally with one or more accessory ingredients. In some embodiments, a compressed tablet is prepared by compressing in a suitable machine a compound or composition disclosed herein in a free-flowing form such as a powder or granules, optionally mixed with binders, inert diluents, or lubricating, surface active or dispersing agents. In some embodiments, a molded tablet is made by molding in a suitable machine a mixture of the powdered compound moistened with an inert liquid diluent. In some embodiments, a tablet disclosed herein is coated or scored. In some embodiments, a tablet disclosed herein is formulated so as to provide slow or controlled release of a compound or composition disclosed herein therein. In some embodiments, a tablet disclosed herein further comprises an excipient. In some embodiments, a tablet disclosed herein further comprises inert diluents, such as calcium carbonate, sodium carbonate, lactose, calcium phosphate or sodium phosphate; granulating and disintegrating agents, such as microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. In some embodiments, a composition comprising a compound disclosed herein further comprises a sweetening agent, flavoring agent, coloring agent, or preserving agents.

In some embodiments, a compound or composition disclosed herein is formulated as a hard gelatin capsule. In some embodiments, a compound or composition disclosed herein is mixed with an inert solid diluent, for example, calcium carbonate, calcium phosphate or kaolin.

In some embodiments, a push-fit capsule contains a compound or composition disclosed herein in admixture with a filler (e.g., lactose, binders such as starches, and/or lubricants such as talc or magnesium stearate and, optionally, stabilizers).

In some embodiments, a soft capsule comprises a compound or composition disclosed herein dissolved or suspended in suitable liquids, such as fatty oils, liquid paraffin, or liquid polyethylene glycols. In some embodiments, a stabilizer is added. In some embodiments, a compound or composition disclosed herein is mixed with a water soluble carrier such as polyethyleneglycol or an oil medium, for example peanut oil, liquid paraffin, or olive oil.

In some embodiments, a dragee core is provided with suitable coatings. In some embodiments, concentrated sugar solutions are used. In some embodiments, the sugar solution comprises gum arabic, talc, polyvinyl pyrrolidone, carbopol gel, polyethylene glycol, and/or titanium dioxide, lacquer solutions, and suitable organic solvents or solvent mixtures.

In some embodiments, a compound or composition disclosed herein is formulated as an aqueous suspension. In some embodiments, a compound or composition disclosed herein further comprises a suspending agent, for example sodium carboxymethylcellulose, methylcellulose, hydroxypropylmethyl-cellulose, sodium alginate, polyvinyl-pyrrolidone, gum tragacanth and gum acacia; or a dispersing or wetting agent (e.g., a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. In some embodiments, a compound or composition disclosed herein further comprises a preservative, for example ethyl, or n-propyl p-hydroxybenzoate; a coloring agent; a flavoring agents; a sweetening agent, such as sucrose, saccharin or aspartame; or combinations thereof.

In some embodiments, a compound or composition disclosed herein is formulated as an oily suspension. In some embodiments, an oily suspension is formulated by suspending a compound or composition disclosed herein in a vegetable oil, for example arachis oil, olive oil, sesame oil or coconut oil, or in mineral oil such as liquid paraffin. In some embodiments, a composition or compound disclosed herein further comprises a thickening agent, for example beeswax, hard paraffin or cetyl alcohol. In some embodiments, a composition or compound disclosed herein further comprises a sweetening agent, a flavoring agent, or a combination thereof. In some embodiments, a composition or compound disclosed herein further comprises an anti-oxidant such as butylated hydroxyanisol or alpha-tocopherol.

In some embodiments, a compound or composition disclosed herein is formulated as an oil-in-water emulsion. In some embodiments, the oily phase is a vegetable oil, for example olive oil or arachis oil, or a mineral oil, for example liquid paraffin or mixtures of these. In some embodiments, an oil-in-water emulsion comprises an emulsifying agent. In some embodiments, the emulsifying agent is a naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. In some embodiments, a composition disclosed herein further comprises a sweetening agent, flavoring agent, preservative, or antioxidant.

In some embodiments, a composition or compound disclosed herein is formulated as a syrup or elixir. In some embodiments, a syrup or elixir further comprises a sweetening agent, for example glycerol, propylene glycol, sorbitol or sucrose. In some embodiments, a syrup or elixir further comprises a demulcent, a preservative, a flavoring agent, a coloring agent, and antioxidant, or a combination thereof.

In some embodiments, a compound or composition disclosed herein is formulated for parenteral administration (e.g., by bolus injection or continuous infusion). In some embodiments, a formulation for parenteral administration comprises suspending agents (fatty oils such as sesame oil, or synthetic fatty acid esters, such as ethyl oleate or triglycerides, or liposomes), thickening agents (e.g., sodium carboxymethyl cellulose, sorbitol, or dextran), stabilizing agents, dispersing agents, or combinations thereof. In some embodiments, a formulation for parenteral administration further comprises an antioxidant, buffer, bacteriostat, solute which render the formulation isotonic with blood, or a combination thereof. In some embodiments, a formulation for injection further comprises a preservative.

In some embodiments, a formulation for parenteral administration is an aqueous solution. In some embodiments, a formulation for parenteral administration comprises water, Ringer's solution, or isotonic sodium chloride solution.

In some embodiments, a formulation for parenteral administration is in the form of an oil-in-water micro-emulsion where a compound or composition disclosed herein is dissolved in the oily phase. In some embodiments, the oily phase comprises a mixture of soybean oil and lecithin. In some embodiments, the oily phase is introduced into a water and glycerol mixture and processed to form a microemulsion.

In some embodiments, a formulation for parenteral administration is administered into a patient's blood-stream by local bolus injection. In some embodiments, a continuous intravenous delivery device is utilized. An example of such a device is the Deltec CADD-PLUS™ model 5400 intravenous pump.

In some embodiments, a formulation for parenteral administration is presented in unit-dose or multi-dose containers, for example sealed ampoules and vials. In some embodiments, a formulation for parenteral administration is stored in powder form or in a freeze-dried (lyophilized) condition requiring only the addition of the sterile liquid carrier, for example, saline or sterile pyrogen-free water, prior to use. In some embodiments, a formulation for parenteral administration extemporaneous injection solutions and suspensions are prepared from sterile powders, granules and tablets of the kind previously described.

In some embodiments, a compound or composition disclosed herein is formulated as a depot preparation. In some embodiments, a depot preparation is administered by implantation (for example subcutaneously or intramuscularly) or by intramuscular injection. In some embodiments, a compound or composition disclosed herein is formulated with any suitable polymeric or hydrophobic material (e.g., emulsion in an acceptable oil), ion exchange resin. In some embodiments, a compound disclosed herein is formulated as a sparingly soluble derivatives, for example, as a sparingly soluble salt.

In some embodiments, a compound or composition disclosed herein is formulated for buccal or sublingual administration. In some embodiments, a compound or composition disclosed herein is in the form of a tablet, lozenge, pastille, or gel. In some embodiments, formulation for buccal or sublingual administration further comprises a flavoring agent (e.g., sucrose, acacia, or tragacanth).

In some embodiments, a compound or composition disclosed herein is formulated for rectal administration (e.g., as a suppository or retention enema). In some embodiments, a compound or composition disclosed herein is formulated as a suppository. In some embodiments, a rectal formulation comprises a non-irritating excipient which is solid at ordinary temperatures but liquid at the rectal temperature. In some embodiments, a rectal formulation comprises cocoa butter, glycerinated gelatin, hydrogenated vegetable oils, mixtures of polyethylene glycols of various molecular weights and fatty acid esters of polyethylene glycol.

In some embodiments, a compound or composition disclosed herein is administered topically, that is by non-systemic administration. In some embodiments, a compound or composition disclosed herein is administered to the epidermis or the buccal cavity. In some embodiments, a compound or composition disclosed herein is formulated as a gel, liniment, lotion, cream, ointment, paste, or solution (e.g., as drops suitable for administration to the eye, ear or nose). In some embodiments, compound disclosed herein comprises from about 0.001% to 10% w/w of a topical formulation. In some embodiments, compound disclosed herein comprises from about 1% to 2% by weight of a topical formulation. In some embodiments, compound disclosed herein comprises about 10% w/w of a topical formulation; preferably, less than 5% w/w; more preferably from 0.1% to 1% w/w.

In some embodiments, a pharmaceutical formulation for administration by inhalation is delivered from an insufflator, nebulizer pressurized packs or other means of delivering an aerosol spray. In some embodiments, a pressurized pack comprises a suitable propellant (e.g., dichlorodifluoromethane, trichlorofluoromethane, dichlorotetrafluoroethane, or carbon dioxide). In some embodiments, a device for administering an inhalable formulation comprises a meter. In some embodiments, a pharmaceutical formulation for administration by inhalation is in the form of a dry powder composition, for example a powder mix of the compound and a suitable powder base such as lactose or starch. In some embodiments, the powder composition is presented in unit dosage form, in for example, capsules, cartridges, gelatin or blister packs from which the powder is administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Doses

The amount of pharmaceutical composition administered will firstly be dependent on the individual being treated. In the instances where pharmaceutical compositions are administered to a human, the daily dosage will normally be determined by the prescribing physician with the dosage generally varying according to the age, sex, diet, weight, general health and response of the individual patient, the severity of the patient's symptoms, the precise indication or condition being treated, the severity of the indication or condition being treated, time of administration, route of administration, the disposition of the composition, rate of excretion, drug combination, and the discretion of the prescribing physician. In some embodiments, treatment is initiated with smaller dosages which are less than the optimum dose of the compound; thereafter, the dosage is increased by small amounts until the optimum effect under the circumstances is reached. In some embodiments, the total daily dosage is divided and administered in portions. The amount and frequency of administration of a compound disclosed herein, and if applicable other therapeutic agents and/or therapies, will be regulated according to the judgment of the attending clinician (physician).

In some embodiments, the dosage is between about 0.001 mg/kg of body weight to about 100 mg/kg of body weight per day (administered in single or divided doses), more preferably at least about 0.1 mg/kg of body weight per day. In some embodiments, the dosage is from about 0.01 mg to about 7000 mg of compound, and preferably includes, e.g., from about 0.05 mg to about 2500 mg. In some embodiments, the dosage is from about 0.1 mg to 1000 mg, preferably from about 1 mg to 300 mg, more preferably 10 mg to 200 mg, according to the particular application. In some instances, dosage levels below the lower limit of the aforesaid range may be more than adequate, while in other cases still larger doses may be employed without causing any harmful side effect, e.g. by dividing such larger doses into several small doses for administration throughout the day. The amount administered will vary depending on the particular $IC_{50}$ value of the compound used. In combinational applications in which the compound is not the sole therapy, it may be possible to administer lesser amounts of compound and still have therapeutic or prophylactic effect.

Combination Therapies

In some embodiments, a compound or composition disclosed herein is administered as a sole therapy. In some embodiments, a compound or composition disclosed herein is administered in combination with an additional active agent.

In some embodiments, the therapeutic effectiveness of a compound disclosed herein is enhanced by administration of an adjuvant. In some embodiments, the benefit experienced by an individual is increased by administering a compound or composition disclosed herein with another therapeutic agent. In some embodiments, the therapeutic effectiveness of a compound disclosed herein is enhanced by administration of physiotherapy, psychotherapy, radiation therapy, application of compresses to a diseased area, rest, altered diet, and the like.

By way of example only, in a treatment for gout the therapeutic effectiveness of a compound disclosed herein is increased by also providing the patient with another therapeutic agent for gout. Or, by way of example only, if one of the side effects experienced by a patient upon receiving one of a compound disclosed herein is nausea, then an anti-nausea agent is administered in combination with the compound.

In some embodiments, a compound disclosed herein is not administered in the same pharmaceutical composition as the additional therapeutic agent. In some embodiments, a compound disclosed herein is administered by a different route from the additional therapeutic agent. For example, a compound or composition disclosed herein is administered orally, while the additional therapeutic agent is administered intravenously.

In some embodiments, a compound or composition disclosed herein and an additional therapeutic agent (or additional therapy) are administered concurrently (e.g., simultaneously, essentially simultaneously or within the same treatment protocol), sequentially or dosed separately.

The particular choice of compound and other therapeutic agent will depend upon the diagnosis of the attending physicians and their judgment of the condition of the individual and the appropriate treatment protocol. In some embodiments, the additional agent is a URAT 1 inhibitor, a xanthine oxidase inhibitor, a xanthine dehydrogenase, a xanthine oxidoreductase inhibitor, a purine nucleoside phosphorylase (PNP) inhibitor, a uric acid transporter inhibitor, a glucose transporter (GLUT) inhibitor, a GLUT-9 inhibitor, a solute carrier family 2 (facilitated glucose transporter), member 9 (SLC2A9) inhibitor, an organic anion transporter (OAT) inhibitor, an OAT-4 inhibitor, or combinations thereof. In certain instances, URAT 1 is an ion exchanger that mediates urate transportation. In certain instances, URAT I mediates urate transportation in the proximal tubule. In certain instances, URAT I exchanges urate in a proximal tubule for lactate and nicotinate. In certain instances, xanthine oxidase oxidizes hypoxanthine to xanthine, and further to uric acid. In certain instances, xanthine dehydrogenase catalyzes the conversion of xanthine, NAD$^+$, and H$_2$O into urate, NADH, and H$^+$. In some embodiments, the additional agent is allopurinol, febuxostat (2-(3-cyano-4-isobutoxyphenyl)-4-methyl-1,3-thiazole-5-carboxylic acid), FYX-051 (4-(5-pyridin-4-yl-1H-[1,2,4]triazol-3-yl)pyridine-2-carbonitrile), probenecid, sulfinpyrazone, benzbromarone, acetaminophen, steroids, nonsteroidal anti-inflammatory drugs (NSAIDs), adrenocorticotropic hormone (ACTH), colchicine, a glucorticoid, an adrogen, a cox-2 inhibitor, a PPAR agonist, naproxen, sevelamer, sibutmaine, troglitazone, proglitazone, another uric acid lowering agent, losartan, fibric acid, benziodarone, salisylate, anlodipine, vitamin C, or combinations thereof.

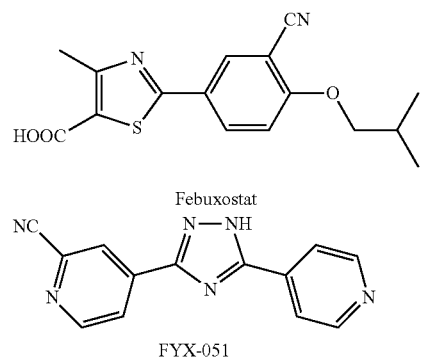

Diseases

Described herein are methods of treating a disease in an individual suffering from said disease comprising administering to said individual an effective amount of a composition comprising a compound disclosed herein or a pharmaceutically acceptable salt, solvate, polymorph, ester, tautomer or prodrug thereof.

Also described herein are methods of preventing or delaying onset of a disease in an individual at risk for developing said disease comprising administering to said individual an effective amount to prevent or delay onset of said disease, of a composition comprising a compound disclosed herein or a pharmaceutically acceptable salt, solvate, polymorph, ester, tautomer or prodrug thereof.

Further described herein are methods for the prophylaxis or treatment of any disease or disorder in which aberrant levels of uric acid plays a role including, without limitation: hyperuricemia, gout, gouty arthritis, inflammatory arthritis, kidney disease, nephrolithiasis (kidney stones), joint inflammation, deposition of urate crystals in joints, urolithiasis (formation of calculus in the urinary tract), deposition of urate crystals in renal parenchyma, Lesch-Nyhan syndrome, Kelley-Seegmiller syndrome, gout flare, tophaceous gout, kidney failure, or combinations thereof in a human or other mammal. The methods disclosed herein extend to such a use and to the use of the compounds for the manufacture of a medicament for treating such diseases or disorders. Further, the methods disclosed herein extend to the administration to a human an effective amount of a compound disclosed herein for treating any such disease or disorder.

Individuals that can be treated with the compounds described herein, or a pharmaceutically acceptable salt, ester, prodrug, solvate, hydrate or derivative of said compounds, according to the methods of this invention include, for example, individuals that have been diagnosed as having gout, gouty arthritis, inflammatory arthritis, kidney disease, nephrolithiasis (kidney stones), joint inflammation, deposition of urate crystals in joints, urolithiasis (formation of calculus in the urinary tract), deposition of urate crystals in renal parenchyma, Lesch-Nyhan syndrome, Kelley-Seegmiller syndrome, gout flare, tophaceous gout, kidney failure, or combinations thereof.

In some embodiments, an individual having an aberrant uric acid level is administered an amount of at least one compound disclosed herein sufficient to modulate the aberrant uric acid level (e.g., to a medically-acceptable level). In some embodiments, an individual treated with the compounds disclosed herein displays aberrant uric acid levels wherein the uric acid levels in blood exceed a medically-accepted range (i.e., hyperuricemia). In some embodiments, an individual treated with the compounds disclosed herein displays aberrant uric acid levels wherein uric acid levels in the blood exceed 360 µmol/L (6 mg/dL) for a female individual or 400 µmol/L (6.8 mg/dL) for a male individual. In some embodiments, an individual treated with the compounds disclosed herein displays aberrant uric acid levels wherein uric acid levels in urine exceed a medically-accepted range (i.e., hyperuricosuria). In some embodiments, an individual treated with the compounds disclosed herein displays aberrant uric acid levels wherein uric acid levels in urine exceed 800 mg/day (in a male individual) and greater than 750 mg/day (in a female individual).

In some embodiments, an individual treated with the compounds disclosed herein (1) displays aberrant uric acid levels, and (2) suffers from a cardiovascular disorder. In some embodiments, an individual treated with the compounds disclosed herein (1) displays aberrant uric acid levels, and (2) suffers from an aneurysm; angina; atherosclerosis; a stroke; cerebrovascular disease; congestive heart failure; coronary artery disease; and/or a myocardial infarction. In some embodiments, an individual treated with the compounds disclosed herein (1) displays aberrant uric acid levels, and (2) displays (a) c-reactive protein (CRP) levels above about 3.0 mg/L; (b) homocysteine levels above about 15.9 mmol/L; (c) LDL levels above about 160 mg/dL; (d) HDL levels below about 40 mg/dL; and/or (e) serum creatinine levels above about 1.5 mg/dL.

In some embodiments, an individual treated with the compounds disclosed herein (1) displays aberrant uric acid levels, and (2) suffers from diabetes. In some embodiments, an individual treated with the compounds disclosed herein (1) displays aberrant uric acid levels, and (2) suffers from Type I diabetes. In some embodiments, an individual treated with the compounds disclosed herein (1) displays aberrant uric acid levels, and (2) suffers from Type II diabetes. In some embodiments, an individual treated with the compounds disclosed herein (1) displays aberrant uric acid levels, and (2) suffers from a loss of beta cells of the islets of Langerhans in the pancreas. In some embodiments, an individual treated with the compounds disclosed herein (1) displays aberrant uric acid levels, and (2) suffers from insulin resistance and/or reduced insulin sensitivity. In some embodiments, an individual treated with the compounds disclosed herein (1) displays aberrant uric acid levels, and (2) displays (a) a fasting plasma glucose level≧126 mg/dL; (b) a plasma glucose level≧200 mg/dL two hours after a glucose tolerance test; and/or (c) symptoms of hyperglycemia and casual plasma glucose levels≧200 mg/dL (11.1 mmol/l).

In some embodiments, an individual treated with the compounds disclosed herein (1) displays aberrant uric acid levels, and (2) suffers from metabolic syndrome. In some embodiments, an individual treated with the compounds disclosed herein (1) displays aberrant uric acid levels, and (2) suffers from (a) diabetes mellitus, impaired glucose tolerance, impaired fasting glucose and/or insulin resistance, (b) at least two of (i) blood pressure: ≧140/90 mmHg; (ii) dyslipidaemia: triglycerides (TG): ≧1.695 mmol/L and high-density lipoprotein cholesterol (HDL-C)≦0.9 mmol/L (male), ≦1.0 mmol/L (female); (iii) central obesity: waist:hip ratio>0.90 (male); >0.85 (female), and/or body mass index>30 kg/m2; and (iv) microalbuminuria: urinary albumin excretion ratio≧20 mg/min or albumin:creatinine ratio≧30 mg/g. In some embodiments, an individual treated with the compounds disclosed herein (1) displays aberrant uric acid levels, and (2) suffers from insulin resistance (i.e., the top 25% of the fasting insulin values among non-diabetic individuals) and (b) at least two of (i) central obesity: waist circumference≧94 cm (male), ≧80 cm (female); (ii) dyslipidaemia: TG≧2.0 mmol/L and/or HDL-C<1.0 mmol/L or treated for dyslipidaemia; (iii) hypertension: blood pressure≧140/90 mmHg or antihypertensive medication; and (iv) fasting plasma glucose≧6.1 mmol/L. In some embodiments, an individual treated with the compounds disclosed herein (1) displays aberrant uric acid levels, and (2) displays at least three of (a) elevated waist circumference: Men≧40 inches (men) and ≧35 inches (women); (b) elevated triglycerides: ≧150 mg/dL; (c) reduced HDL: <40 mg/dL (men) and <50 mg/dL (women); (d) elevated blood pressure: ≧130/85 mm Hg or use of medication for hypertension; and (e) elevated fasting glucose: ≧100 mg/dL (5.6 mmol/L) or use of medication for hyperglycemia.

In some embodiments, an individual treated with the compounds disclosed herein (1) displays aberrant uric acid levels, and (2) suffers from kidney disease or kidney failure. In some embodiments, an individual treated with the compounds disclosed herein (1) displays aberrant uric acid levels, and (2) displays oliguria (decreased urine production. In some embodiments, an individual treated with the compounds disclosed herein (1) displays aberrant uric acid levels, and (2) produces less than 400 mL per day of urine (adults), produces less than 0.5 mL/kg/h of urine (children), or produces less than 1 mL/kg/h of urine (infants).

Uric Acid

In certain instances, purines (adenine, guanine), derived from food or tissue turnover (cellular nucleotides undergo continuous turnover), are catabolized in humans to their final oxidation product, uric acid. In certain instances, guanine is oxidized to xanthine, which is turn is further oxidized to uric acid by the action of xanthine oxidase; adenosine is converted to inosine which is further oxidized to hypoxanthine. In certain instances, xanthine oxidase oxidizes hypoxanthine to xanthine, and further to uric acid. In certain instances, as part of the reverse process, the enzyme hypoxanthine-guanine phosphoribosyltransferase (HGPRT) salvages guanine and hypoxanthine.

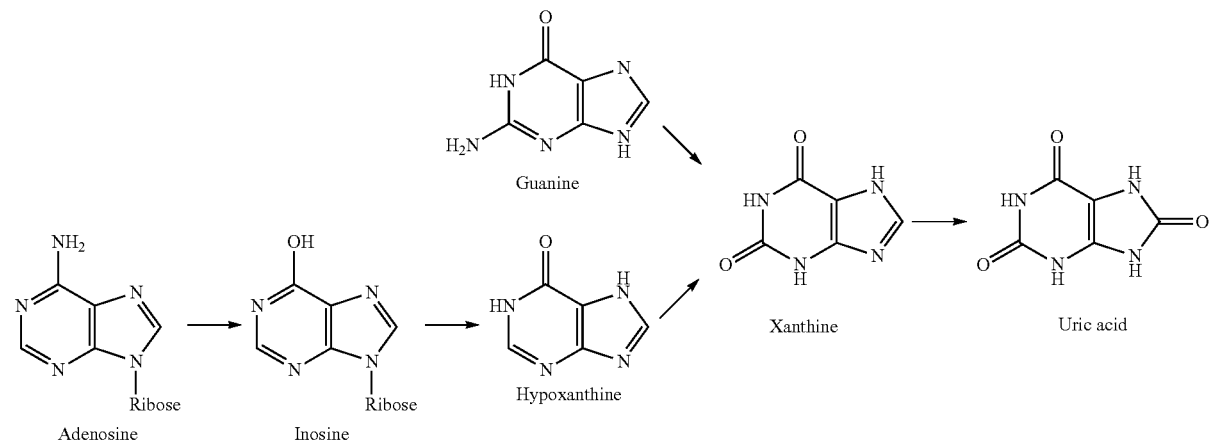

In certain instances, the keto form of uric acid is in equilibrium with the enol form which loses a proton at physiological pH to form urate. In certain instances, (e.g., under serum conditions (pH 7.40, 37° C.)), about 98% of uric acid is ionized as the monosodium urate salt. In certain instances, urate is a strong reducing agent and potent antioxidant. In humans, about half the antioxidant capacity of plasma comes from uric acid.

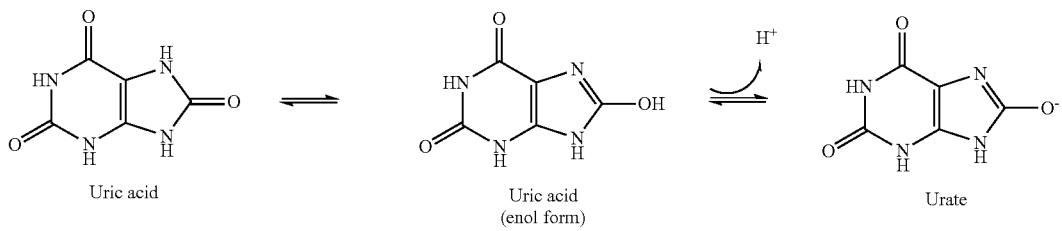

In certain instances, most uric acid dissolves in blood and passes to the kidneys, where it is excreted by glomerular filtration and tubular secretion. In certain instances, a substantial fraction of uric acid is reabsorbed by the renal tubules. One of the peculiar characteristics of the uric acid transport system is that, although the net activity of tubular function is reabsorption of uric acid, the molecule is both secreted and reabsorbed during its passage through the nephron. In certain instances, reabsorption dominates in the S1 and S3 segments of the proximal tubule and secretion dominates in the S2 segment. In certain instances, the bidirectional transport results in drugs that inhibit uric acid transport decreasing, rather than increasing, the excretion of uric acid, compromising their therapeutic usefulness. In certain instances, normal uric acid levels in human adults (5.1+/−0.93 mg/dL) are close to the limits of urate solubility (~7 mg/dL at 37° C.), which creates a delicate physiologic urate balance. In certain instances, the normal uric acid range for females is approximately 1 mg/dL below the male range.

Hyperuricemia

In certain instances, hyperuricemia is characterized by higher than normal blood levels of uric acid, sustained over long periods of time. In certain instances, increased blood urate levels may be due to enhanced uric acid production (~10-20%) and/or reduced renal excretion (~80-90%) of uric acid. In certain instances, causes of hyperuricemia may include:

Obesity/weight gain

Excessive alcohol use

Excessive dietary purine intake (foods such as shellfish, fish roe, scallops, peas lentils, beans and red meat, particularly offal—brains, kidneys, tripe, liver)

Certain medications, including low-dose aspirin, diuretics, niacin, cyclosporine, pyrazinamide, ethambutol, some high blood pressure drugs and some cancer chemotherapeutics, immunosuppressive and cytotoxic agents Specific disease states, particularly those associated with a high cell turnover rate (such as malignancy, leukemia, lymphoma or psoriasis), and also including high blood pressure, hemoglobin disorders, hemolytic anemia, sickle cell anemia, various nephropathies, myeloproliferative and lymphoproliferative disorders, hyperparathyroidism, renal disease, conditions associated with insulin resistance and diabetes mellitus, and in transplant recipients, and possibly heart disease Inherited enzyme defects Abnormal kidney function (e.g. increased ATP turn over, reduced glomerular urate filtration)

Exposure to lead (plumbism or "saturnine gout")

In certain instances, hyperuricemia may be asymptomatic, though is associated with the following conditions: Gout, Gouty arthritis, Uric acid stones in the urinary tract (urolithiasis), Deposits of uric acid in the soft tissue (tophi), Deposits of uric acid in the kidneys (uric acid nephropathy), and Impaired kidney function, possibly leading to chronic and acute renal failure.

Gout

Prevalence

The incidence of gout has increased over the past two decades and, in the United States, affects as much as 2.7% of the population aged 20 years and older, totaling over 5.1 million American adults. Gout is more common in men than women, (3.8% or 3.4 million men vs. 1.6% or 1.7 million women), typically affecting men in their 40's and 50's (although gout attacks can occur after puberty which sees an increase in uric acid levels). An increase in prevalence of gout from 2.9 to 5.2 per 1000 in the time period 1990 to 1999 was observed, with most of the increase occurring in those over the age of 65. Gout attacks are more common in women after menopause. In certain instances, gout is one of the most common forms of arthritis, accounting for approximately 5% of all arthritis cases. In certain instances, kidney failure and urolithiasis occur in 10-18% of individuals with gout and are common sources of morbidity and mortality from the disease.

Leading Causes

In most cases, gout is associated with hyperuricemia. In certain instances, individuals suffering from gout excrete approximately 40% less uric acid than nongouty individuals for any given plasma urate concentrations. In certain instances, urate levels increase until the saturation point is reached. In certain instances, precipitation of urate crystals occurs when the saturation point is reached. In certain instances, these hardened, crystallized deposits (tophi) form in the joints and skin, causing joint inflammation (arthritis). In certain instances, deposits are be made in the joint fluid (synovial fluid) and/or joint lining (synovial lining) Common areas for these deposits are the large toe, feet, ankles and hands (less common areas include the ears and eyes). In certain instances, the skin around an affected joint becomes red and shiny with the affected area being tender and painful to touch. In certain instances, gout attacks increase in frequency. In certain instances, untreated acute gout attacks lead to permanent joint damage and disability. In certain instances, tissue deposition of urate leads to: acute inflammatory arthritis, chronic arthritis, deposition of urate crystals in renal parenchyma and urolithiasis. In certain instances, the incidence of gouty arthritis increases 5 fold in individuals with serum urate levels of 7 to 8.9 mg/dL and up to 50 fold in individuals with levels>9 mg/dL (530 µmol/L). In certain instances, individuals with gout develop renal insufficiency and end stage renal disease (i.e., "gouty nephropathy"). In certain instances, gouty nephropathy is characterized by a chronic interstitial nephropathy, which is promoted by medullary deposition of monosodium urate.

In certain instances, gout includes painful attacks of acute, monarticular, inflammatory arthritis, deposition of urate crystals in joints, deposition of urate crystals in renal parenchyma, urolithiasis (formation of calculus in the urinary tract), and nephrolithiasis (formation of kidney stones). In certain instances, secondary gout occurs in individuals with cancer, particularly leukemia, and those with other blood disorders (e.g. polycythemia, myeloid metaplasia, etc).

Symptoms

In certain instances, attacks of gout develop very quickly, frequently the first attack occurring at night. In certain instances, symptoms include sudden, severe joint pain and extreme tenderness in the joint area, joint swelling and shiny red or purple skin around the joint. In certain instances, the attacks are infrequent lasting 5-10 days, with no symptoms between episodes. In certain instances, attacks become more frequent and may last longer, especially if the disorder is not controlled. In certain instances, episodes damage the affected joint(s) resulting in stiffness, swelling, limited motion and/or persistent mild to moderate pain.

Treatment

In certain instances, gout is treated by lowering the production of uric acid. In certain instances, gout is treated by increasing the excretion of uric acid. In certain instances, gout is treated by URAT 1, xanthine oxidase, xanthine dehydrogenase, xanthine oxidoreductase, a purine nucleoside phosphorylase (PNP) inhibitor, a uric acid transporter (URAT) inhibitor, a glucose transporter (GLUT) inhibitor, a GLUT-9 inhibitor, a solute carrier family 2 (facilitated glucose transporter), member 9 (SLC2A9) inhibitor, an organic anion transporter (OAT) inhibitor, an OAT-4 inhibitor, or combinations thereof. In general, the goals of gout treatment are to i) reduce the pain, swelling and duration of an acute attack, and ii) prevent future attacks and joint damage. In certain instances, gout attacks are treated successfully using a combination of treatments. In certain instances, gout is one of the most treatable forms of arthritis.

i) Treating the gout attack. In certain instances, the pain and swelling associated with an acute attack of gout can be addressed with medications such as acetaminophen, steroids, nonsteroidal anti-inflammatory drugs (NSAIDs), adrenocorticotropic hormone (ACTH) or colchicine. In certain instances, proper medication controls gout within 12 to 24 hours and treatment is stopped after a few days. In certain instances, medication is used in conjunction with rest, increased fluid intake, ice-packs, elevation and/or protection of the affected area/s. In certain instances, the aforementioned treatments do not prevent recurrent attacks and they do not affect the underlying disorders of abnormal uric acid metabolism.

ii) Preventing future attacks. In certain instances, reducing serum uric acid levels below the saturation level is the goal for preventing further gout attacks. In some cases, this is achieved by decreasing uric acid production (e.g. allopurinol), or increasing uric acid excretion with uricosuric agents (e.g. probenecid, sulfinpyrazone, benzbromarone).

In certain instances, allopurinol inhibits uric acid formation, resulting in a reduction in both the serum and urinary uric acid levels and becomes fully effective after 2 to 3 months.

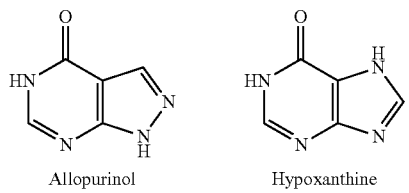

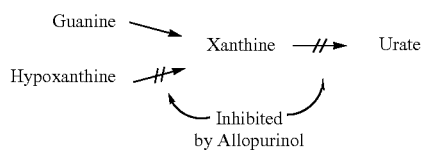

In certain instances, allopurinol is a structural analogue of hypoxanthine, (differing only in the transposition of the carbon and nitrogen atoms at positions 7 and 8), which inhibits the action of xanthine oxidase, the enzyme responsible for the conversion of hypoxanthine to xanthine, and xanthine to uric acid. In certain instances, it is metabolized to the corresponding xanthine analogue, alloxanthine (oxypurinol), which is also an inhibitor of xanthine oxidase. In certain instances, alloxanthine, though more potent in inhibiting xanthine oxidase, is less pharmaceutically acceptable due to low oral bioavailability. In certain instances, fatal reactions due to hypersensitivity, bone marrow suppression, hepatitis, and vasculitis have been reported with Allopurinol. In certain instances, the incidence of side effects may total 20% of all individuals treated with the drug. Treatment for disorders of uric acid metabolism has not evolved significantly in the following two decades since the introduction of allopurinol.

In certain instances, Uricosuric agents (e.g., probenecid, sulfinpyrazone, and benzbromarone) increase uric acid excretion. In certain instances, probenecid causes an increase in uric acid secretion by the renal tubules and, when used chronically, mobilizes body stores of urate. In certain instances, 25-50% of individuals treated with probenecid fail to achieve reduction of serum uric acid levels<6 mg/dL. In certain instances, insensitivity to probenecid results from drug intolerance, concomitant salicylate ingestion, and renal impairment. In certain instances, one-third of the individuals develop intolerance to probenecid. In certain instances, administration of uricosuric agents also results in urinary calculus, gastrointestinal obstruction, jaundice and anemia.

Plumbism or "Saturnine Gout"

In certain instances, excessive exposure to lead (lead poisoning or plumbism) results in "saturnine gout," a lead-induced hyperuricemia due to lead inhibition of tubular urate transport causing decreased renal excretion of uric acid. In certain instances, more than 50% of individuals suffering from lead nephropathy suffer from gout. In certain instances, acute attacks of saturnine gout occur in the knee more frequently than the big toe. In certain instances, renal disease is more frequent and more severe in saturnine gout than in primary gout. In certain instances, treatment consists of excluding the individual from further exposure to lead, the use of chelating agents to remove lead, and control of acute gouty arthritis and hyperuricaemia. In certain instances, saturnine gout is characterized by less frequent attacks than primary gout. In certain instances, lead-associated gout occurs in pre-menopausal women, an uncommon occurrence in non lead-associated gout.

Lesch-Nyhan Syndrome

In certain instances, Lesch-Nyhan syndrome (LNS or Nyhan's syndrome) affects about one in 100,000 live births. In certain instances, LNS is caused by a genetic deficiency of the enzyme hypoxanthine-guanine phosphoribosyltransferase (HGPRT). In certain instances, LNS is an X-linked recessive disease. In certain instances, LNS is present at birth in baby boys. In certain instances, the disorder leads to severe gout, poor muscle control, and moderate mental retardation, which appear in the first year of life. In certain instances, the disorder also results in self-mutilating behaviors (e.g., lip and finger biting, head banging) beginning in the second year of life. In certain instances, the disorder also results in gout-like swelling in the joints and severe kidney problems. In certain instances, the disorder leads neurological symptoms include facial grimacing, involuntary writhing, and repetitive movements of the arms and legs similar to those seen in Huntington's disease. The prognosis for individuals with LNS is poor. In certain instances, the life expectancy of an untreated individual with LNS is less than about 5 years. In certain instances, the life expectancy of a treated individual with LNS is greater than about 40 years of age.

Hyperuricemia and Other Diseases

In certain instances, hyperuricemia is found in individuals with cardiovascular disease (CVD) and/or renal disease. In certain instances, hyperuricemia is found in individuals with prehypertension, hypertension, increased proximal sodium reabsorption, microalbuminuria, proteinuria, kidney disease, obesity, hypertriglyceridemia, low high-density lipoprotein cholesterol, hyperinsulinemia, hyperleptinemia, hypoadiponectinemia, peripheral, carotid and coronary artery disease, atherosclerosis, congenative heart failure, stroke, tumor lysis syndrome, endothelial dysfunction, oxidative stress, elevated renin levels, elevated endothelin levels, and/or elevated C-reactive protein levels. In certain instances, hyperuricemia is found in individuals with obesity (e.g., central obesity), high blood pressure, hyperlipidemia, and/or impaired fasting glucose. In certain instances, hyperuricemia is found in individuals with metabolic syndrome. In certain instances, gouty arthritis is indicative of an increased risk of acute myocardial infarction. In some embodiments, administration of the compounds described herein to an individual are useful for decreasing the likelihood of a clinical event associated with a disease or condition linked to hyperuricemia, including, but not limited to, prehypertension, hypertension, increased proximal sodium reabsorption, microalbuminuria, proteinuria, kidney disease, obesity, hypertriglyceridemia, low high-density lipoprotein cholesterol, hyperinsulinemia, hyperleptinemia, hypoadiponectinemia, peripheral, carotid and coronary artery disease, atherosclerosis, congenative heart failure, stroke, tumor lysis syndrome, endothelial dysfunction, oxidative stress, elevated renin levels, elevated endothelin levels, and/or elevated C-reactive protein levels.

In some embodiments, the compounds described herein are administered to an individual suffering from a disease or condition requiring treatment with a compound that is a diuretic. In some embodiments, the compounds described herein are administered to an individual suffering from a disease or condition requiring treatment with a compound that is a diuretic, wherein the diuretic causes renal retention of urate. In some embodiments, the disease or condition is congestive heart failure or essential hypertension.

In some embodiments, administration of the compounds described herein to an individual are useful for improving motility or improving quality of life.

In some embodiments, administration of the compounds described herein to an individual is useful for treating or decreasing the side effects of cancer treatment.

In some embodiments, administration of the compounds described herein to an individual is useful for decreasing kidney toxicity of cis-platin.

EXAMPLES

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

I Chemical Syntheses

The following examples (1-32) illustrate methods for preparing compounds of the invention.

General

Examples 1-23

The reactions described in examples 1-23 are performed in a nitrogen or argon atmosphere unless otherwise stated. Room temperature is 18-22° C. Solution percentages or ratios express a volume to volume relationship, unless stated otherwise. Purification by reverse phase HPLC(RP-HPLC) is performed using a gradient of acetonitrile/water containing TFA (0.06%) (CombiPrep ODS-AQ 50×20 mm, 5μ, 120 A). Analytical HPLC is carried out under standard conditions using a Combiscreen ODS-AQ C18 reverse phase column, YMC, 50×4.6 mm i.d., 51 μM, 120 A at 220 nM, elution with a linear gradient as described in the following table (Solvent A is 0.06% TFA in $H_2O$; solvent B is 0.06% TFA in acetonitrile):

| Time (min) | Flow (mL/min) | Solvent A (%) | Solvent B (%) |
| --- | --- | --- | --- |
| 0 | 3 | 95 | 3 |
| 0.5 | 3 | 95 | 5 |
| 6 | 3 | 50 | 50 |
| 10.5 | 3.5 | 0 | 100 |

Example 1

2-(4'-(2-(1-(4-tert-Butyl-2-chlorophenyl)-1H-tetrazol-5-ylthio)acetamido)-3'-chlorobiphenyl-4-yl)acetic acid

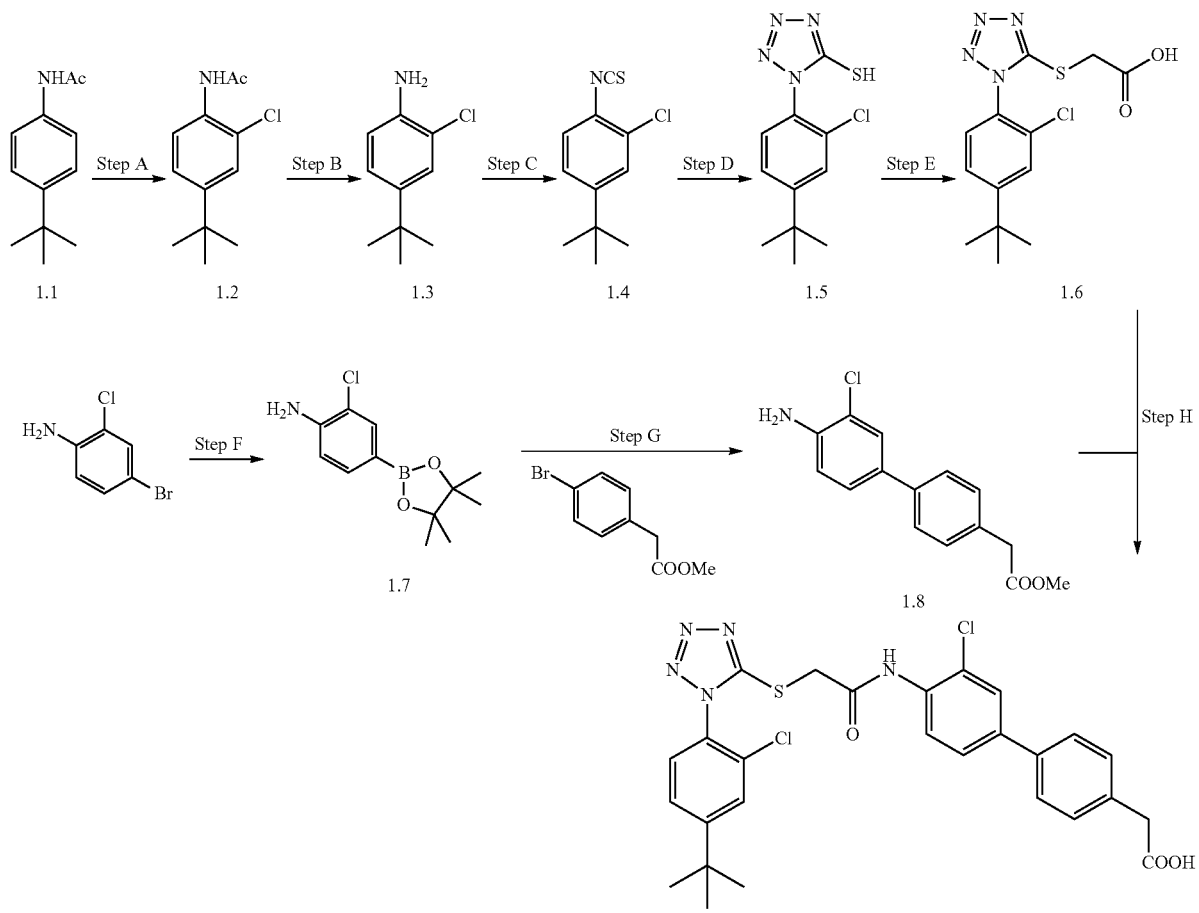

a) Compound 1.2

To a solution of N-[4-(tert-butyl)phenyl]acetamide 1.1 (2.00 g, 10.5 mmol) in a mixture of acetic acid (3.0 mL) and 12 N HCl (4.6 mL) is added dropwise a solution of NaClO₃ (170 mg, 1.60 mmol) in water (1 mL). After 30 min the resulting orange suspension is diluted with water (80 mL), the precipitate filtered, washed with water and dried to give compound 1.2.

b) Compound 1.3

A solution of N-[4-(tert-butyl)-2-chlorophenyl]acetamide 1.2 (2.00 g, 8.86 mmol) in a mixture of 36 NH₂SO₄ (14 mL) and water (2.9 mL) is heated at 120° C. for 18 h. After cooling the reaction mixture is poured over ice, basified with NaOH solution (10M) and extracted with EtOAc. The organic phase is washed with brine, dried (MgSO₄), filtered and concentrated under reduced pressure. The resulting oil 1.3 is used as such in the next step.

c) Compound 1.4

To a solution of compound 1.3 (765 mg, 4.16 mmol) in CH₂Cl₂ (5 mL) is added di-2-pyridylthiocarbonate (966 mg, 4.16 mmol), and the solution stirred at room temperature overnight. The reaction mixture is washed successively with saturated aqueous NaHCO₃ solution and brine, dried (MgSO₄), filtered and concentrated under reduced pressure to give compound 1.4.

d) Compound 1.5

To a solution of compound 1.4 (925 mg, 4.10 mmol) in ethanol (200 mL) is added NaN₃ (4.3 g, 66 mmol) and the mixture heated to 70° C. After 2 h the reaction mixture is cooled to room temperature and 12 N HCl (2 mL) added. The mixture is concentrated and diluted with EtOAc. The organic layer is extracted with aqueous 1 N NaOH solution, and the aqueous layer acidified with aqueous 6 N HCl solution to form a precipitate. The suspension is filtered and the isolated solid triturated with ether/hexane (1/1) to give compound 1.5.

e) Compound 1.6

To a solution of pyridine (0.34 mL, 4.20 mmol) and compound 1.5 (930 mg, 3.46 mmol) in DMSO (25 mL) is added ethyl 2-bromoacetate (392 µL, 3.46 mmol), and the resulting solution stirred at room temperature for 2 h. The reaction mixture is then diluted with EtOAc and successively washed with water and brine, dried (MgSO$_4$), filtered and concentrated under reduced pressure. The crude ester is dissolved in THF (30 mL) and methanol (10 mL) and aqueous 1 N NaOH solution (3 mL, 3 mmol) added. The solution is stirred at 55° C. for 60 min. Volatile solvents are removed under reduced pressure, and the resulting residue dissolved in aqueous 1 N NaOH solution. The solution is slowly acidified to pH 2 at 0° C. with aqueous 1 N HCl solution. The suspension is filtered and the resulting solid rinsed with water and dried under reduced pressure to give compound 1.6.

f) Compound 1.7

A solution of 4-bromo-2-chloroaniline (4.00 g, 19.37 mmol), bis(pinacolato)diboron (5.90 g, 23.2 mmol) and KOAc (12.3 g, 58.1 mmol) in DMSO (100 mL) is deoxygenated by bubbling nitrogen through it for 45 min. PdCl$_2$(dppf) (1.429, 1.94 mmol) and dppf (1.07 g, 1.94 mmol) are then added and the mixture heated at 100° C. for 4 h. After cooling to room temperature the reaction mixture is diluted with EtOAc, washed successively with water and brine, dried (MgSO$_4$), filtered and concentrated under reduced pressure. The crude product is purified twice by flash chromatography using CH$_2$Cl$_2$ to give intermediate 1.7.

g) Compound 1.8

To a solution of methyl (4-bromophenyl)acetate (obtained from the corresponding acid (267.5 mg, 1.2 mmol) upon treatment with excess diazomethane) in 1,4-dioxane (5 ml) are added intermediate 1.7 (315 mg, 1.20 mmol) and K$_3$PO$_4$ (792 mg, 3.73 mmol). After degassing the reaction mixture for 45 min, PdCl$_2$(dppf) (137 mg, 0.19 mmol) and dppf (136 mg, 0.06 mmol) are added and the mixture heated at 100° C. for 3 h. After cooling to room temperature the reaction mixture is diluted with EtOAc, washed successively with water and brine, dried (MgSO$_4$), filtered and concentrated under reduced pressure. The crude product s purified by flash chromatography using hexane/EtOAc (80/20) to give compound 1.8.

h) 2-(4'-(2-(1-(4-tert-Butyl-2-chlorophenyl)-1H-tetrazol-5-ylthio)acetamido)-3'-chlorobiphenyl-4-yl)acetic acid To an ice-cold solution of acid 1.6 (30.6 mg, 0.09 mmol) and aniline 1.8 (25.8 mg, 0.09 mmol) in pyridine (3 ml) is added PCl$_3$ (8.3 µL). The mixture is stirred at 0° C. for 2 h, quenched with a few drops of water, and concentrated under reduced pressure. The crude product is dissolved in EtOAc and the resulting solution successively washed with aqueous 10% citric acid solution, water and brine, dried (MgSO$_4$), filtered and concentrated under reduced pressure. The crude product is purified by flash chromatography using hexane/EtOAc (75/25) to afford the corresponding ester (20 mg, 37% yield) as a white solid. To a solution of the ester (20 mg, 0.034 mmol) in THF (3 ml)/methanol (1 ml) is added 1N NaOH (70 µL, 0.070 mmol). After 1 h at 55° C., the reaction is concentrated and the crude acid purified by RP-HPLC The pure fractions are combined and concentrated to give 2-(4'-(2-(1-(4-tert-butyl-2-chlorophenyl)-1H-tetrazol-5-ylthio)acetamido)-3'-chlorobiphenyl-4-yl)acetic acid.

Example 2

2-(3'-Chloro-4'-(2-(1-(2-chloro-4-cyclopropylphenyl)-1H-tetrazol-5-ylthio)acetamido)biphenyl-4-yl)acetic acid

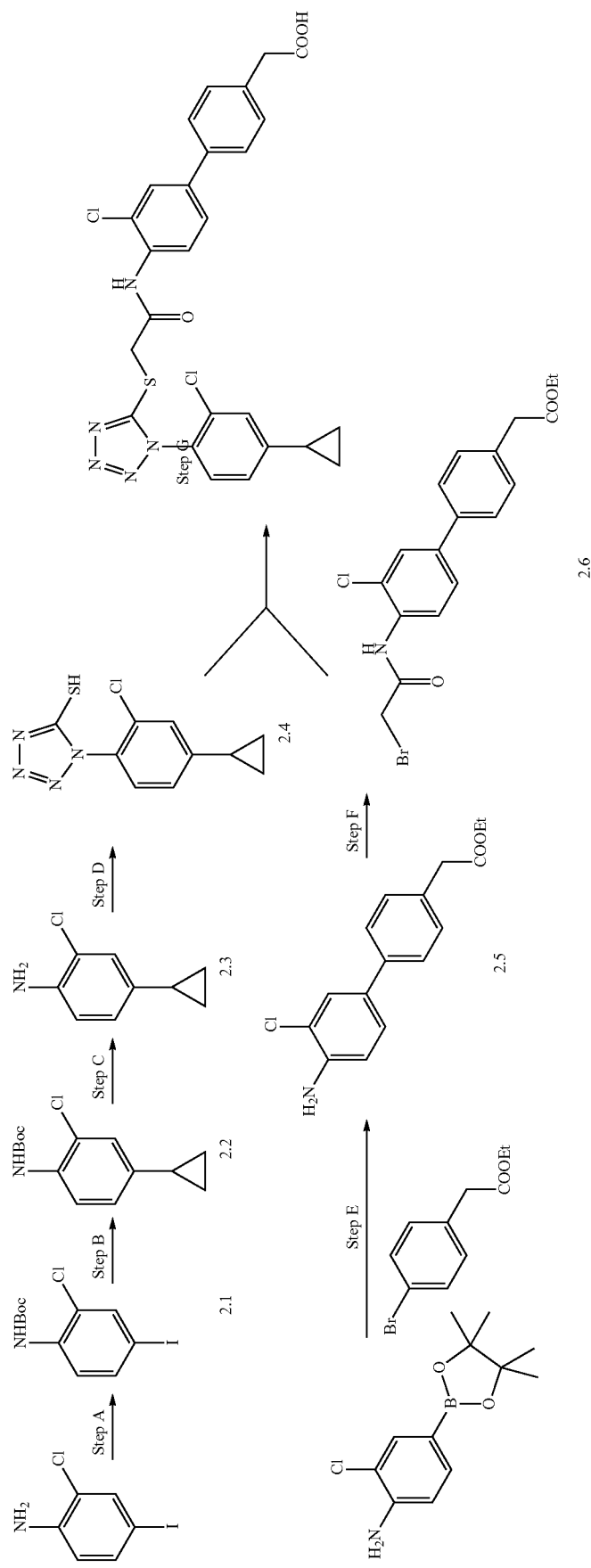

a) Compound 2.1

To a solution of 4-iodo-2-chloroaniline (5.00 g, 19.7 mmol) in THF (40 mL) is added dropwise NaHMDS (1 M in THF, 41.4 mL) and the mixture stirred at room temperature for 90 min. BOC$_2$O (4.10 g, 19.0 mmol) in THF (30 mL) is added to the reaction mixture and the resulting solution stirred overnight. The reaction mixture is diluted with water and extracted twice with EtOAc. The combined organic phase is successively washed with aqueous 1 N HCl, water and brine, dried (MgSO$_4$), filtered and concentrated under reduced pressure. The crude product is purified by flash chromatography using hexane/EtOAc (99/1 to 4:1) to give compound 2.1.

b) Compound 2.2

To a solution of cyclopropylbromide (6.97 mL, 87.0 mmol) in THF (90 mL) cooled to −78° C., is added "BuLi (2.5M in hexane, 34 mL) over 45 min. After 1 h, a solution of ZnBr$_2$ (flame dried under high vacuum, 23.2 g, 103 mmol) in THF (90 mL) is added by cannula and the mixture allowed to warm to room temperature. After 1 h a solution of compound 2.1 dissolved in THF (90 mL) is added followed by Pd(PPh$_3$)$_4$ (2.15 g, 1.86 mmol) under stream of nitrogen. The reaction mixture is then heated at reflux for 1 h, cooled in an ice bath and quenched with a mixture of aqueous 1 N HCl solution and aqueous 5% Na$_2$S$_2$O$_3$ solution. The resulting mixture is extracted with ether several times and the combined organic layers successively washed with aqueous 1 N HCl solution, water and brine, dried (MgSO$_4$), filtered and concentrated under reduced pressure. The crude product is dissolved in hexane (100 mL), filtered through a silica gel pad, and the filtrate concentrated to yield compound 2.2.

c) Compound 2.3

A solution of compound 2.2 (1.27 g, 4.74 mmol) in anhydrous HCl in dioxane (4 N, 20 mL) is heated at 45° C. for 30 min. The resulting suspension is concentrated to dryness and the viscous oil partitioned between EtOAc and water. The aqueous layer is basified with aqueous 1N NaOH solution, and extracted with EtOAc. The organic phase is washed with brine, dried (MgSO$_4$), filtered and concentrated under reduced pressure to give aniline 2.3.

d) Compound 2.4

Compound 2.4 is obtained following the procedures described in EXAMPLE 1, Steps c and d.

e) Compound 2.5

Aniline 2.5 is obtained following the procedure described in EXAMPLE 1 Step g, using the corresponding ethyl ester.

f) Compound 2.6

To a mixture of aniline 2.5 (202 mg, 0.70 mmol) and Et$_3$N (110 μL, 0.79 mmol) in CH$_2$Cl$_2$ (8 mL) is added bromoacetyl chloride (65 μL, 0.75 mmol). After 18 h the reaction mixture is diluted with EtOAc, washed with water and brine, dried (MgSO$_4$), filtered and concentrated under reduced pressure. The crude product is purified by flash chromatography using hexane/EtOAc (75/25) to give compound 2.6.

g) 2-(3'-Chloro-4'-(2-(1-(2-chloro-4-cyclopropylphenyl)-1H-tetrazol-5-ylthio)acetamido)biphenyl-4-yl)acetic acid To a solution of compound 2.4 (39.0 mg, 0.15 mmol) in DMF (2 mL) is added compound 2.6 (62.0 mg, 0.15 mmol) and K$_2$CO$_3$ (25 mg, 0.18 mmol). After 2 h, aqueous 1 N NaOH solution (0.5 mL) is added and stirring continued for 2 h. The reaction mixture is quenched with TFA (0.5 mL), and the resulting crude acid purified by HPLC using a gradient of acetonitrile/water containing TFA (0.06%) (CombiPrep ODS-AQ 50×20 mm, 5μ, 120 A). The pure fractions are combined and concentrated to give 2-(3'-chloro-4'-(2-(1-(2-chloro-4-cyclopropylphenyl)-1H-tetrazol-5-ylthio)acetamido)biphenyl-4-yl)acetic acid.

Example 3

General Procedure for the Chlorination of an Aniline

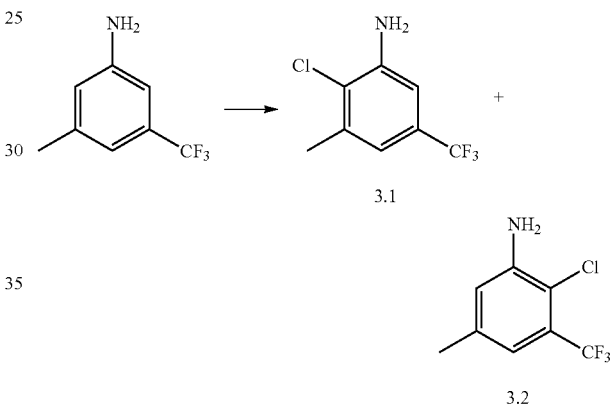

A solution of 3-methyl-5-(trifluoromethyl)aniline (2.0 g, 11.4 mmol) and N-chlorosuccinimide (1.7 g, 12.7 mmol) in acetonitrile (15 mL) is heated for 6 h. Upon cooling the reaction is concentrated to dryness and the resulting mixture purified by flash chromatography using hexane/EtOAc (95/5) to give compound 3.1, followed by hexane/EtOAc (90/10) to obtain compound 3.2.

Example 4

N-(2-Chloro-4-(4-hydroxy-3,3-dimethylbut-1-ynyl)phenyl)-2-(1-(2-chloro-4-cyclopropylphenyl)-1H-tetrazol-5-ylthio)acetamide

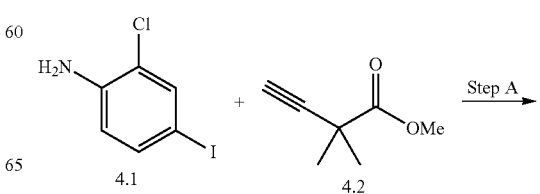

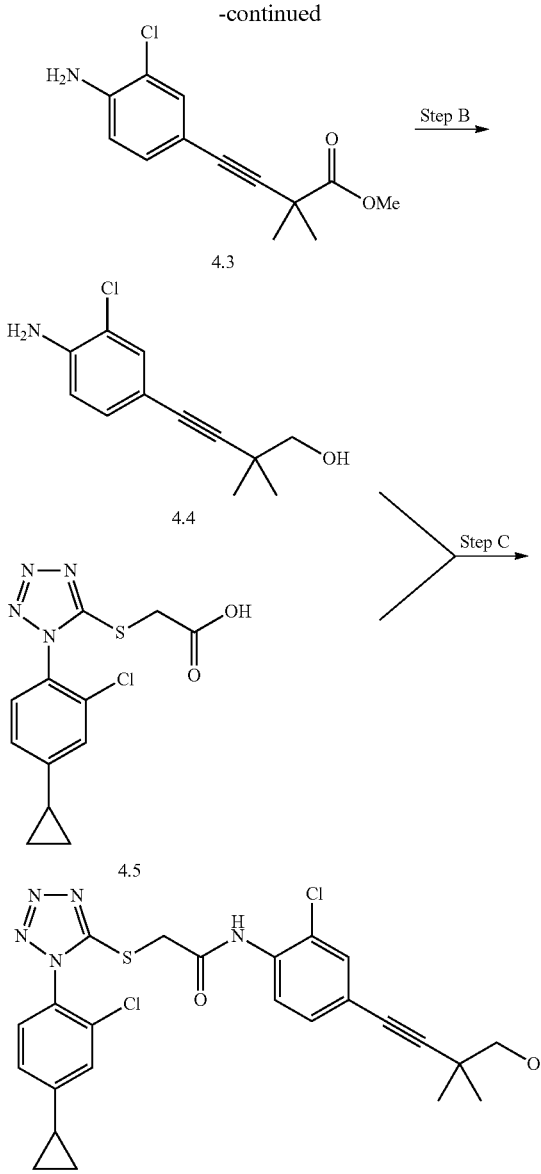

1N Rochelle salt/ether (200 mL, 1:1). The organic phase is collected and the aqueous phase extracted with ether (3×40 mL). The combined organic phases are washed with brine (50 mL), dried ($Na_2SO_4$), filtered and concentrated under reduced pressure to afford alcohol 4.4.

c) N-(2-Chloro-4-(4-hydroxy-3,3-dimethylbut-1-ynyl)phenyl)-2-(1-(2-chloro-4-cyclopropylphenyl)-1H-tetrazol-5-ylthio)acetamide Oxalyl chloride (40 µL, 45 µmol) and DMF (one drop) are successively added to an ice-cold solution of acid 4.5 (prepared from compound 2.4 using a procedure analogous to that described in EXAMPLE 1 step e) (135 mg, 0.41 mmol) in $CH_2Cl_2$ (4 mL). The reaction mixture is stirred at room temperature for 1 h then concentrated under reduced pressure. The residue is dissolved in THF (5 mL) and cooled to 0° C. A solution of amine 4.4 (77.0 mg, 0.34 mmol) in THF (1 mL) and pyridine (70 µL, 0.86 mmol) are successively added to the solution. The reaction mixture is stirred at room temperature for 2 h, diluted with saturated aqueous $NaHCO_3$ solution and extracted with ether (3×50 mL). The combined organic phases are washed with brine, dried ($Na_2SO_4$), filtered and concentrated under reduced pressure. The crude residue is purified by flash chromatography (hexane/EtOAc, 4/1) to afford N-(2-chloro-4-(4-hydroxy-3,3-dimethylbut-1-ynyl)phenyl)-2-(1-(2-chloro-4-cyclopropylphenyl)-1H-tetrazol-5-ylthio)acetamide.

Example 5

2-(4-(3-Chloro-4-(2-(1-(2-chloro-4-cyclopropylphenyl)-1H-tetrazol-5-ylthio)acetamido)phenyl)-2,2-dimethylbut-3-ynylamino)acetic acid

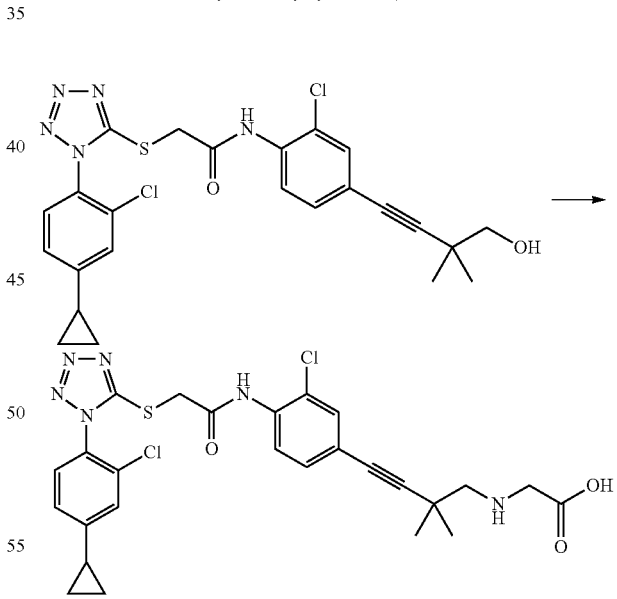

a) Compound 4.3

To a solution of aniline 4.1 (706.2 mg, 2.78 mmol) in THF (27 mL) is added cuprous iodide (55.8 mg, 0.29 mmol), $Et_2NH$ (2.37 mL, 22.9 mmol) and compound 4.2 (370 mg, 2.93 mmol). The mixture is degassed for 15 min by bubbling argon through the solution. $Pd(PPh_3)_4$ (339 mg, 0.29 mmol) is added and the reaction mixture heated at reflux until total disappearance of the starting material as indicated by TLC. The black solution is cooled to room temperature, silica gel added and all volatiles removed under reduced pressure to give a dry powder which is applied to the top of a column. The crude compound is purified by flash chromatography (hexane/EtOAc, 75/25) to afford compound 4.3.

b) Compound 4.4

$LiAlH_4$ (33.2 mg, 0.87 mmol) is added to an ice-cold THF/ether (1:2) solution of compound 4.3. The reaction mixture is stirred at room temperature for 1 h then poured over aqueous To an ice-cold solution of N-(2-chloro-4-(4-hydroxy-3,3-dimethylbut-1-ynyl)phenyl)-2-(1-(2-chloro-4-cyclopropylphenyl)-1H-tetrazol-5-ylthio)acetamide (200 mg, 0.39 mmol) in $CH_2Cl_2$ (4 mL) is added Dess-Martin periodinane (328 mg, 0.77 mmol). The reaction mixture is stirred at room temperature for 30 min, diluted with saturated aqueous $Na_2S_2O_3$ solution (50 mL) and extracted with ether (3×50 mL). The combined organic phases are washed with brine, dried ($Na_2SO_4$), filtered and concentrated under reduced pressure. The crude oil is dissolved in ethanol (5 mL) and added to a solution of glycine methyl ester (72.9 mg, 0.58 mmol) and acetic acid (0.2 mL) in ethanol (5 mL) at room temperature. NaCNBH$_3$ (36.5 mg, 0.58 mmol) is then added and the resulting suspension stirred at room temperature for 1 h. The reaction mixture is diluted with saturated aqueous NaHCO$_3$ solution (30 mL) and extracted with ether (3×30 mL). The combined organic phases are washed with brine, dried (Na$_2$SO$_4$), filtered and concentrated under reduced pressure. The crude oil is dissolved in DMSO (4 mL), cooled to 0° C. and aqueous 1N LiOH solution (0.39 mL, 0.39 mmol) added. The resulting mixture is stirred at room temperature for 30 min, diluted with TFA (0.5 mL) and purified by RP-HPLC to afford, after lyophilization, 2-(4-(3-Chloro-4-(2-(1-(2-chloro-4-cyclopropylphenyl)-1H-tetrazol-5-ylthio)acetamido)phenyl)-2,2-dimethylbut-3-ynylamino)acetic acid.

Example 6

5-(3-chloro-4-(2-(1-(2-chloro-4-cyclopropylphenyl)-1H-tetrazol-5-ylthio)acetamido)phenyl)-3,3-dimethylpent-4-ynoic acid

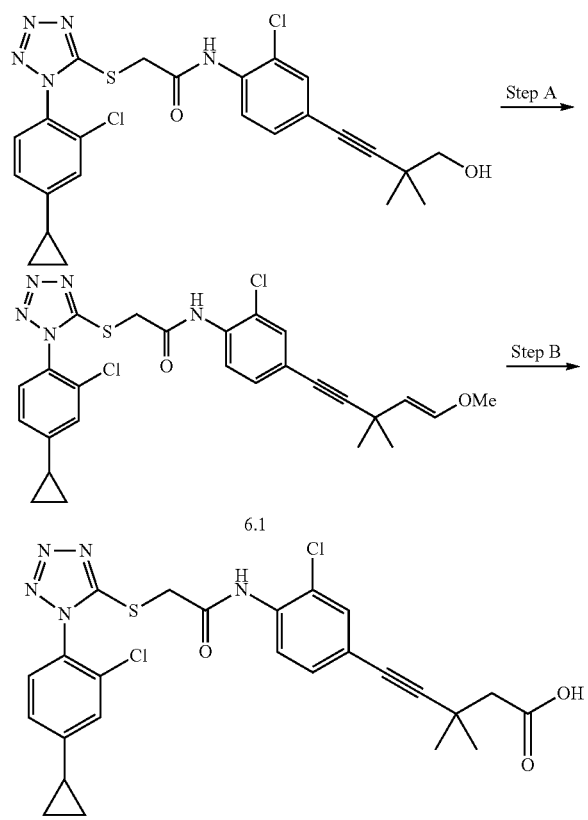

a) Compound 6.1

Dess-Martin periodinane (196 mg, 0.46 mmol) is added to an ice-cold solution of N-(2-chloro-4-(4-hydroxy-3,3-dimethylbut-1-ynyl)phenyl)-2-(1-(2-chloro-4-cyclopropylphenyl)-1H-tetrazol-5-ylthio)acetamide (217 mg. 0.42 mmol) in CH$_2$Cl$_2$ (4 mL), and stirred at room temperature for 1 h. The mixture is diluted with saturated aqueous Na$_2$S$_2$O$_3$ solution and extracted with ether (3×30 mL). The combined organic phases are washed with brine, dried (Na$_2$SO$_4$), filtered and concentrated under reduced pressure. The resulting crude oil is dissolved in dry THF (2 mL) and added to an ice-cold solution of potassium tert-butoxide (182 mg, 1.62 mmol) and (methoxymethyl) triphenylphosphonium chloride (579 mg, 1.69 mmol) in THF (5 mL), (previously stirred for 30 min). The resulting reaction mixture is stirred for 1 h at 0° C., then 1 h at room temperature. Saturated aqueous NaHCO$_3$ solution (20 mL) is added and the mixture extracted with ether (3×30 mL). The combined organic phases are washed with brine, dried (Na$_2$SO$_4$), filtered and concentrated under reduced pressure. Purification by flash chromatography using hexane/EtOAc (7/3) affords compound 6.1.

b) 5-(3-Chloro-4-(2-(1-(2-chloro-4-cyclopropylphenyl)-1H-tetrazol-5-ylthio)acetamido)phenyl)-3,3-dimethylpent-4-ynoic acid Aqueous 10% HCl solution (3 mL) is added to an ice-cold solution of compound 6.1 (79.7 mg, 0.15 mmol) in THF (2 mL). The reaction mixture is stirred for 30 min at 0° C., and 3 h at room temperature, then extracted with ether (3×30 mL). The combined organic phases are washed with saturated aqueous NaHCO$_3$ solution, brine, dried (Na$_2$SO$_4$), filtered and concentrated under reduced pressure. The resulting crude oil is dissolved in $^t$BuOH/CH$_2$Cl$_2$ (3 mL. 3:1). Aqueous pH 7.0 potassium phosphate buffer (3 mL) is added, followed by 2-methyl-2-butene (5 mL) and NaClO$_2$ (66.5 mg-, 0.74 mmol). The reaction mixture is stirred for 3 h at room temperature, diluted with aqueous 10% HCl solution (10 mL) and extracted with CH$_2$Cl$_2$ (5×10 mL). The combined organic phases are dried (Na$_2$SO$_4$), filtered and concentrated under reduced pressure. The crude product is purified by RP-HPLC to afford, after lyophilization, 5-(3-chloro-4-(2-(1-(2-chloro-4-cyclopropylphenyl)-1H-tetrazol-5-ylthio)acetamido)phenyl)-3,3-dimethylpent-4-ynoic acid.

Example 7

2-(1-(4-tert-Butyl-2-chlorophenyl)-1H-tetrazol-5-ylthio)-N-(2-chloro-4-(3-(pyrrolidin-1-yl)prop-1-ynyl)phenyl)acetamide

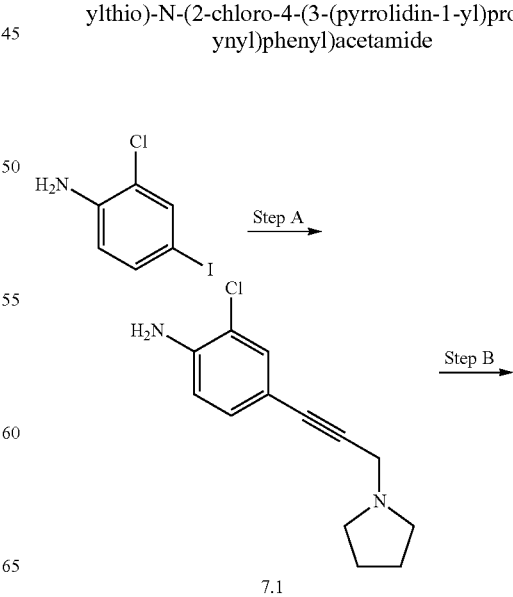

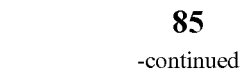

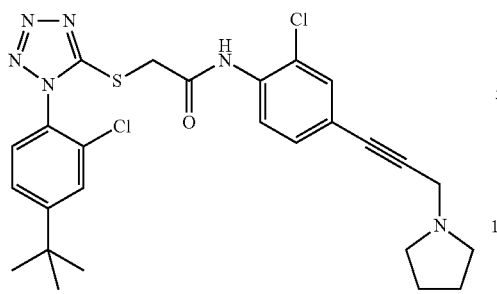

a) Compound 7.1

To a solution of 2-chloro-4-iodoaniline (500 mg, 1.97 mmol) is added propargyl bromide (258 μL, 2.17 mmol), cuprous iodide (37.5 mg, 197 μmol) and pyrrolidine (0.82 mL, 9.82 mmol). The mixture is degassed by bubbling argon in the solution for 20 min Pd(PPh$_3$)$_4$ (228 mg, 0.20 mmol) is added and the mixture heated at reflux for 5 h. The reaction mixture is cooled to room temperature, silica gel added and the volatiles removed under reduced pressure to afford a dry powder. The crude compound is purified by flash chromatography using hexane/EtOAC/Et$_3$N (50/45/5) to afford compound 7.1.

b) 2-(1-(4-tert-Butyl-2-chlorophenyl)-1H-tetrazol-5-ylthio)-N-(2-chloro-4-(3-(pyrrolidin-1-yl)prop-1-ynyl)phenyl)acetamide 2-(1-(4-tert-Butyl-2-chlorophenyl)-1H-tetrazol-5-ylthio)-N-(2-chloro-4-(3-(pyrrolidin-1-yl)prop-1-ynyl)phenyl)acetamide is obtained using a method similar to the one described in EXAMPLE 1, Step h, using aniline 7.1 in place of aniline 1.8.

Example 8

N-(2-Chloro-4-(3-(2-hydroxybenzylamino)-3-methylbut-1-ynyl)phenyl)-2-(1-(2-chloro-4-cyclopropylphenyl)-1H-tetrazol-5-ylthio)acetamide

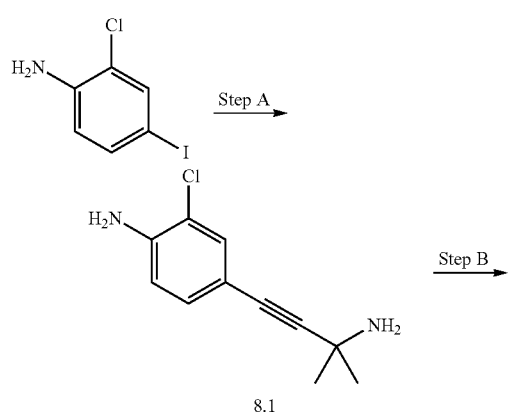

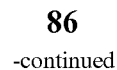

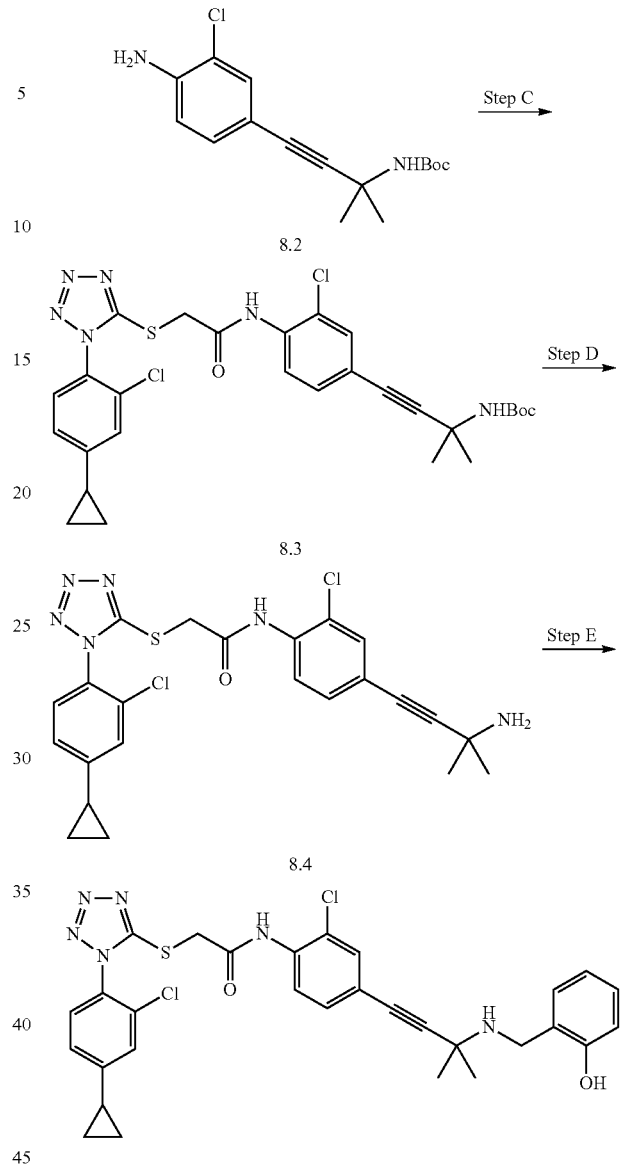

a) Compound 8.1

Compound 8.1 is obtained using a method similar to the one described in EXAMPLE 4, Step a, replacing alkyne 4.2 with 3-amino-3-methyl-1-butyne.

b) Compound 8.2

BOC$_2$O (7.29 g, 33.4 mmol) is added to a solution of the propargylamine 8.1 (6.97 g, 33.4 mmol) in methanol (100 mL) at room temperature. The resulting mixture is stirred at room temperature for 2 h, diluted with saturated aqueous NaHCO$_3$ solution (100 mL) and extracted with EtOAc (3×50 mL). The combined organic phases are washed with saturated aqueous NaHCO$_3$ solution and brine, dried (Na$_2$SO$_4$), filtered and concentrated under reduced pressure. The crude residue is purified by flash chromatography (hexane/EtOAc, 7/3) to afford aniline 8.2.

c) Compound 8.3

Compound 8.3 is obtained using a method similar to the one described in EXAMPLE 4, Step c.

d) Compound 8.4

Anhydrous 4 N HCl in 1,4-dioxane (0.23 mL, 0.93 mmol) is added to a solution of compound 8.3 (56.0 mg, 93 µmol) in 1,4-dioxane (0.5 mL), and stirred at room temperature overnight. The mixture is concentrated under reduced pressure, and the crude residue purified by RP-HPLC to afford, after lyophilization, compound 8.4.

e) N-(2-Chloro-4-(3-(2-hydroxybenzylamino)-3-methylbut-1-ynyl)phenyl)-2-(1-(2-chloro-4-cyclopropylphenyl)-1H-tetrazol-5-ylthio)acetamide Acetic acid (30 µL) is added to a solution of aniline 8.4 in ethanol (2 mL) at room temperature. Salicylaldehyde (18.3 mg, 0.15 mmol) is then added, followed by NaCNBH$_3$ (5 µg, 75 µmol). The reaction is stirred at room temperature for 1 h, concentrated under reduced pressure, and the crude residue purified by RP-HPLC to afford, after lyophilization, N-(2-chloro-4-(3-(2-hydroxybenzylamino)-3-methylbut-1-ynyl) phenyl)-2-(1-(2-chloro-4-cyclopropylphenyl)-1H-tetrazol-5-ylthio)acetamide.

Example 9

2-(1-(4-tert-Butyl-2-chlorophenyl)-1H-tetrazol-5-ylthio)-N-(2-chloro-4-((1-hydroxycyclobutyl)ethynyl)phenyl)acetamide

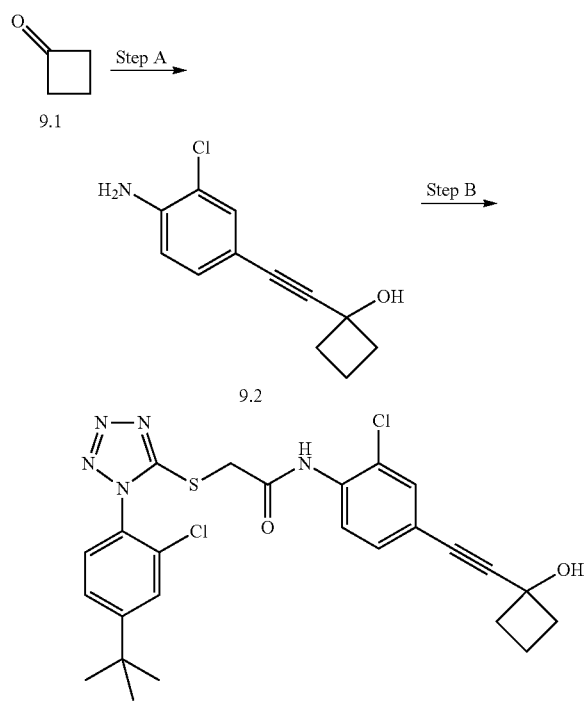

a) Compound 9.2

Cyclobutanone (1.00 g, 14.3 mmol) is added to solution of ethynyl magnesium bromide in THF (0.5M, 40 mL, 20 mmol), at −78° C. The reaction mixture is stirred at room temperature for 1 h, diluted with saturated aqueous NH$_4$Cl solution and extracted with ether (4×30 mL). The combined organic phases are washed with brine, dried (Na$_2$SO$_4$), filtered and concentrated under reduced pressure. The resulting crude oil is dissolved in THF (25 mL) and 2-chloro-4-iodoaniline (1.25 g, 4.93 mmol) added, followed by cuprous iodide (94 mg, 190 mmol) and Et$_2$NH (1.3 mL, 12 mmol). The mixture is degassed by bubbling argon through the solution for 15 min and Pd(PPh$_3$)$_4$ (570 mg, 0.49 mmol) added. The solution is heated at reflux for 5 h. After cooling to room temperature, silica gel is added and the volatiles removed under reduced pressure. The crude product is purified by flash chromatography (hexane/EtOAc, 19/1) to afford compound 9.2.

b) 2-(1-(4-tert-Butyl-2-chlorophenyl)-1H-tetrazol-5-ylthio)-N-(2-chloro-4-((1-hydroxycyclobutyl)ethynyl)phenyl)acetamide 2-(1-(4-tert-Butyl-2-chlorophenyl)-1H-tetrazol-5-ylthio)-N-(2-chloro-4-((1-hydroxycyclobutyl)ethynyl)phenyl)acetamide is obtained using a method similar to the one described in EXAMPLE 7, Step b.

Example 10

N-(2-Chloro-4-(3-methyl-3-(2-(pyrrolidin-1-yl) ethoxy)but-1-ynyl)phenyl)-2-(1-(2-chloro-4-cyclopropylphenyl)-1H-tetrazol-5-ylthio)acetamide

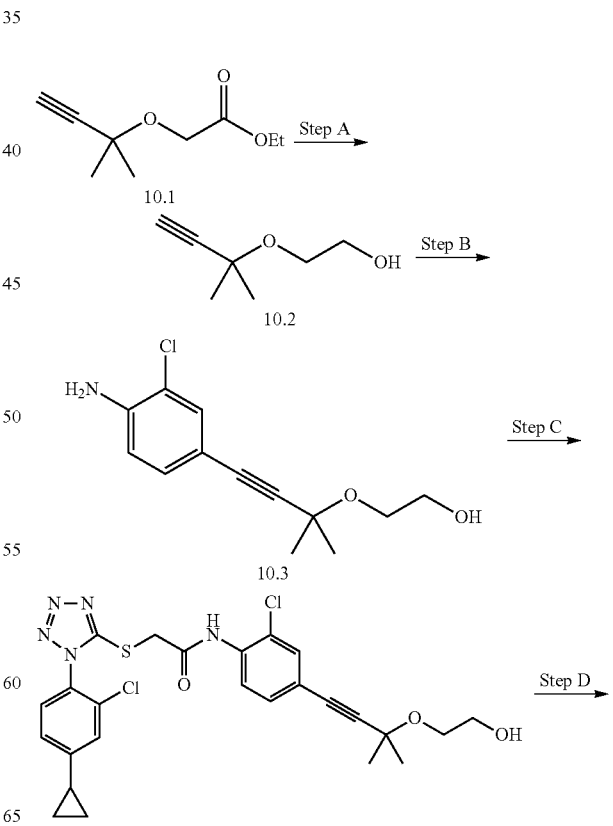

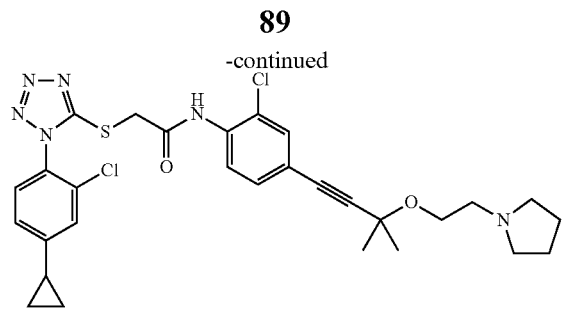

a) Compound 10.2

LiAlH₄ (446 mg, 11.7 mmol) is added to an ice-cold solution of compound 10.1 (2.00 g, 11.8 mmol) in ether (100 mL). The reaction mixture is stirred at room temperature for 1 h then poured over aqueous 1 N Rochelle salt solution (200 mL). The solution is diluted with ether (200 mL) and stirred vigorously for 1 h. The organic phase is collected, washed with brine, dried (Na₂SO₄), filtered and concentrated under reduced pressure. The crude oil is purified by flash chromatography (hexane/EtOAc, 4/1) to afford alcohol 10.2.

b) Compound 10.3

Alcohol 10.3 is obtained using a method similar to the one described in EXAMPLE 7, Step a, coupling compound 10.2 with 2-chloro-4-iodoaniline.

c) Compound 10.4

Compound 10.4 is obtained using a method similar to the one described in EXAMPLE 4, Step c.

d) N-(2-Chloro-4-(3-methyl-3-(2-(pyrrolidin-1-yl) ethoxy)but-1-ynyl)phenyl)-2-(1-(2-chloro-4-cyclopropylphenyl)-1H-tetrazol-5-ylthio)acetamide MsCl (1.2 μL, 15 μmmol) is added to an ice cold solution of compound 10.4 (7.8 mg, 14 μmol) and Et₃N (4 μL, 28 μmol) in CH₂Cl₂ (1 mL). The mixture is stirred at room temperature for 2 h, diluted with saturated aqueous NaHCO₃ solution (20 mL) and extracted with ether (3×30 mL). The combined organic phases are washed with brine, dried (Na₂SO₄), filtered and concentrated under reduced pressure. The crude mesylate is dissolved in THF (5 mL) and pyrrolidine (0.1 mL) added. The mixture is heated at reflux overnight, cooled to 0° C., concentrated under reduced pressure and purified by RP-HPLC to afford, after lyophilization, N-(2-chloro-4-(3-methyl-3-(2-(pyrrolidin-1-yl)ethoxy)but-1-ynyl)phenyl)-2-(1-(2-chloro-4-cyclopropylphenyl)-1H-tetrazol-5-ylthio) acetamide.

Example 11

N-(2-Chloro-4-(3-methyl-3-(3-(pyridin-4-yl)propoxy)but-1-ynyl)phenyl)-2-(1-(2-chloro-4-cyclopropylphenyl)-1H-tetrazol-5-ylthio)acetamide

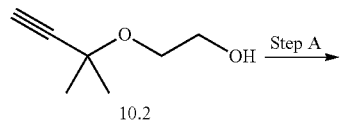

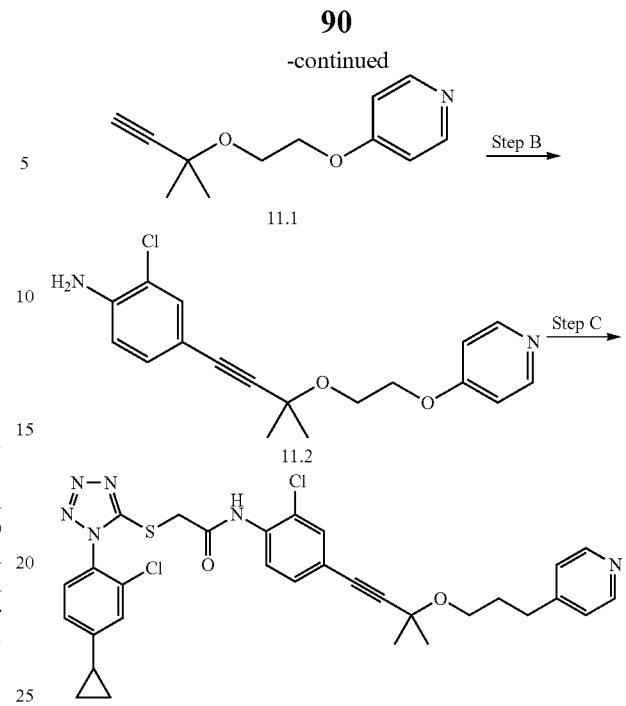

a) Compound 11.1

DEAD (424 mg, 2.43 mmol) is added to an ice-cold solution of alcohol 10.2 (from EXAMPLE 10) (240 mg, 1.87 mmol), 4-hydroxypyridine (196 mg, 2.06 mmol) and PPh₃ (638 mg, 2.43 mmol) in THF (20 mL), and is stirred for 1 h at room temperature. Silica gel is added and the volatiles removed under reduced pressure to afford a dry powder applied onto a pad of silica. Quick elution (hexane/EtOAc, 1/1) affords alkyne 11.1 used as such in the following step.

b) Compound 11.2

Compound 11.2 is obtained using a method similar to the one described in EXAMPLE 7, Step a, coupling compound 11.1 with 2-chloro-4-iodoaniline.

c) N-(2-chloro-4-(3-methyl-3-(3-(pyridin-4-yl)propoxy)but-1-ynyl)phenyl)-2-(1-(2-chloro-4-cyclopropylphenyl)-1H-tetrazol-5-ylthio)acetamide N-(2-Chloro-4-(3-methyl-3-(3-(pyridin-4-yl)propoxy) but-1-ynyl)phenyl)-2-(1-(2-chloro-4-cyclopropylphenyl)-1H-tetrazol-5-ylthio)acetamide is obtained using a method similar to the one described in EXAMPLE 4, Step c.

Example 12

1-((3-Chloro-4-(2-(1-(2-chloro-4-cyclopropylphenyl)-1H-tetrazol-5-ylthio)acetamido) phenyl)ethynyl)cyclopropanecarboxylic acid

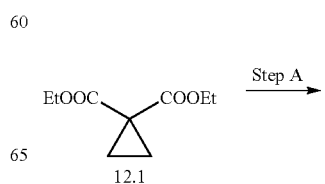

-continued

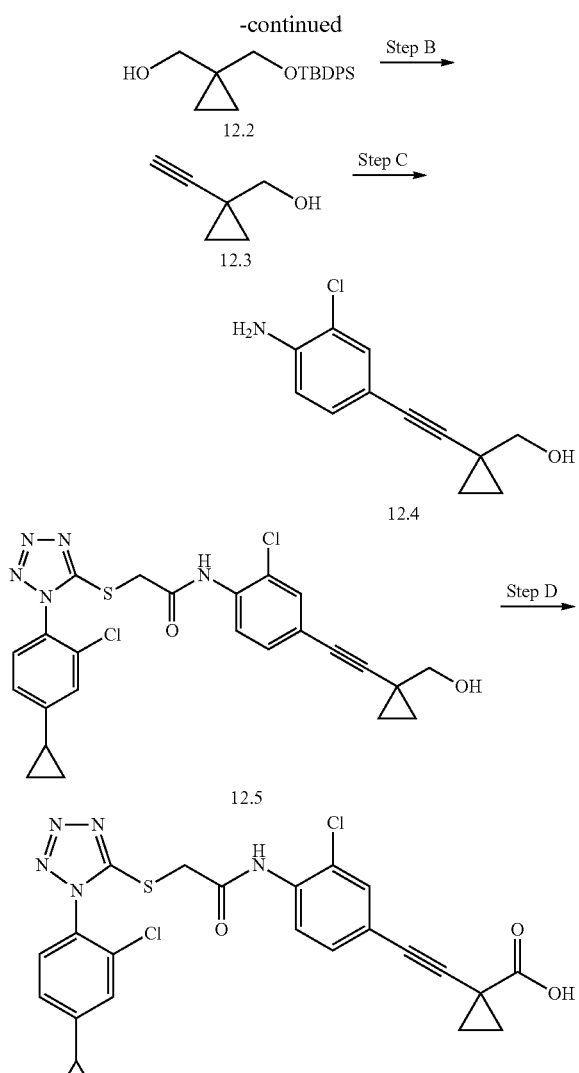

a) Compound 12.2

A solution of diethyl cyclopropane-1,1-dicarboxylate, 12.1, (2.00 g, 10.7 mmol) in THF (15 mL) is slowly added to an ice-cold suspension of LiAlH$_4$ (1.35 g, 35.4 mmol) in THF (100 mL). The mixture is stirred at room temperature for 1 h then Na$_2$SO$_4$ added until no more gas forms. The reaction mixture is filtered through Celite and concentrated under reduced pressure. The crude diol is dissolved in THF (100 mL), cooled to 0° C. and NaH (258 mg, 10.7 mmol) added. The resulting suspension is stirred at room temperature for 1 h and tert-butyldiphenylsilyl chloride (2.95 g, 10.7 mmol) added. The reaction mixture is stirred at room temperature for 1 h, diluted with saturated aqueous NH4Cl solution (100 mL) and extracted with CH$_2$Cl$_2$ (3×100 mL). The combined organic phases are washed with brine, dried (Na$_2$SO$_4$), filtered and concentrated under reduced pressure. The crude residue is purified by flash chromatography (hexane/EtOAc, 4:1) to afford 12.2.

b) Compound 12.3

Dess-Martin periodinane (2.99 g, 7.05 mmol) is added to an ice-cold solution of compound 12.2 (2.40 g, 7.05 mmol) in CH$_2$Cl$_2$ (50 mL). The reaction mixture is stirred at room temperature for 1 h, diluted with saturated aqueous Na$_2$S$_2$O$_3$ solution (20 mL) and saturated aqueous NaHCO$_3$ solution (20 mL) then extracted with ether (3×20 mL). The combined organic phases are washed with brine, dried (Na$_2$SO$_4$), filtered and concentrated under reduced pressure. The crude aldehyde is dissolved in CH$_2$Cl$_2$ (5 mL) and added to an ice-cold solution of PPh$_3$ (7.39 g, 7.05 mmol) and CBr$_4$ (4.67 g, 14.1 mmol) in CH$_2$Cl$_2$ (20 mL) (previously stirred for 1 h at room temperature). The resulting reaction mixture is stirred for 10 min at 0° C. and silica gel added. The volatiles are removed under reduced pressure and the crude compound purified by flash chromatography (hexane to hexane/EtOAc, 98:2).

To a cold (−78° C.) solution of this intermediate in THF (15 mL) is added a solution of $^n$BuLi in hexane (2 M, 5.6 mL). The reaction mixture is stirred for 1.5 h at −78° C., and 1 h at room temperature, then diluted with water (5 mL) and extracted with ether (3×50 mL). The combined organic phases are washed with brine, dried (Na$_2$SO$_4$), filtered and concentrated under reduced pressure. The crude residue is purified by flash chromatography (100% hexane then 2% EtOAc/98% hexane) diluted in THF (10 mL) and treated with TBAF (1M in THF, 8.46 mL, 8.46 mmol). The reaction mixture is stirred for 15 min at room temperature and concentrated under reduced pressure. The residue is purified by flash chromatography (hexane/EtOAc, 4/1) to afford compound 12.3.

c) Compound 12.4

Aniline 12.4 is obtained using a method similar to the one described in EXAMPLE 7, Step a, coupling compound 12.3 with 2-chloro-4-iodoaniline.

d) Compound 12.5

Compound 12.5 is obtained using a method similar to the one described in EXAMPLE 4, Step c.

e) 1-((3-Chloro-4-(2-(1-(2-chloro-4-cyclopropylphenyl)-1H-tetrazol-5-ylthio)acetamido)phenyl)ethynyl)cyclopropanecarboxylic acid Dess-Martin periodinane (16.9 mg, 40.0 μmol) is added to an ice-cold solution of compound 12.5 (32.0 mg, 40.0 μmol) in CH$_2$Cl$_2$ (5 mL). The reaction mixture is stirred at room temperature for 1 h, diluted with saturated aqueous Na$_2$S$_2$O$_3$ solution and extracted with ether (3×20 mL). The combined organic phases are washed with brine, dried (Na$_2$SO$_4$), filtered and concentrated under reduced pressure. The crude oil is dissolved in $^t$BuOH/CH$_2$Cl$_2$ (3 mL, 3:1). Aqueous pH 7.0 potassium phosphate buffer (3 mL) is added, followed by 2-methyl-2-butene (5 mL) and NaClO$_2$ (18 mg, 0.2 mmol). The reaction mixture is stirred for 3 h at room temperature, diluted with aqueous 10% HCl solution (10 mL) and extracted with CH$_2$Cl$_2$ (5×10 mL). The combined organic phases are dried (Na$_2$SO$_4$), filtered and concentrated under reduced pressure. The crude product is purified by RP-HPLC to afford, after lyophilization, 1-((3-chloro-4-(2-(1-(2-chloro-4-cyclopropylphenyl)-1H-tetrazol-5-ylthio)acetamido)phenyl)ethynyl)cyclopropanecarboxylic acid.

Example 13

N-(2-Chloro-4-((1-((4-methylpiperazin-1-yl)methyl)cyclopropyl)ethynyl)phenyl)-2-(1-(2-chloro-4-cyclopropylphenyl)-1H-tetrazol-5-ylthio)acetamide

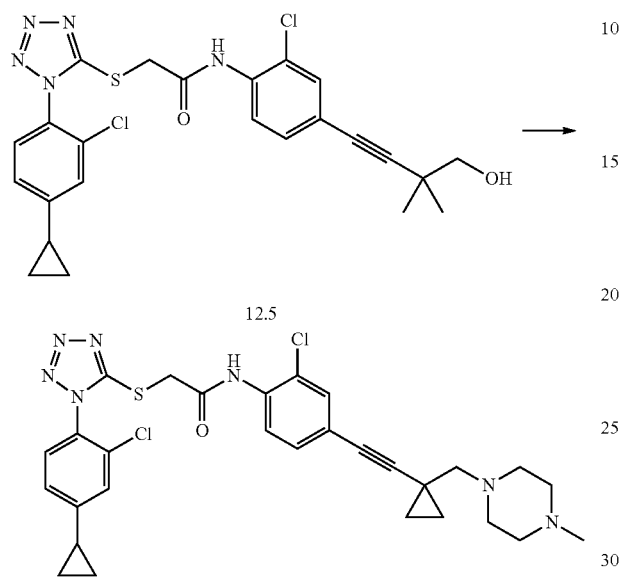

The title compound is obtained using a method analogous to the one described in EXAMPLE 10, Step d.

Example 14

2-(4'-(2-(4-(2-Chloro-4-methylphenyl)thiazol-5-ylthio)acetamido)biphenyl-4-yl)acetic acid

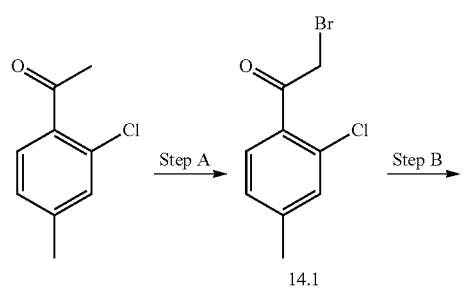

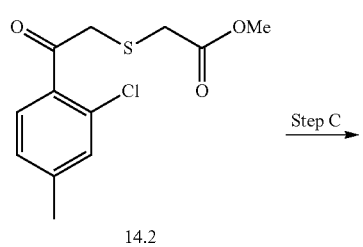

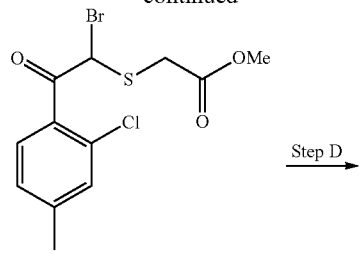

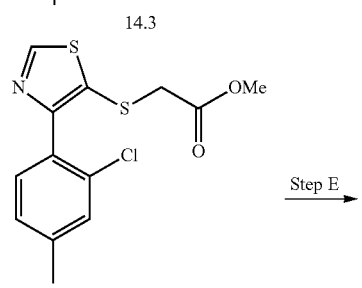

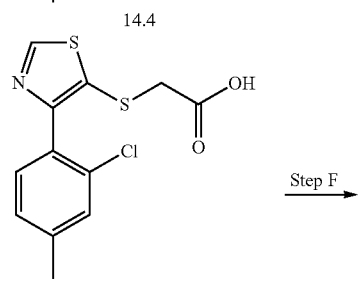

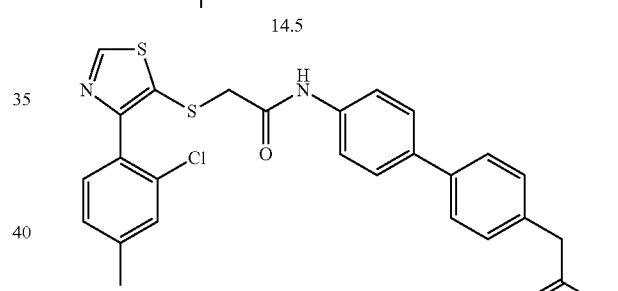

a) Compound 14.1

To a solution of 2-chloro-4-methylacetophenone (3.45 g, 20.4 mmol) in 1,4-dioxane (20 mL) is added at room temperature a solution of $Br_2$ (1.16 mL, 22.4 mmol) in 1,4-dioxane (50 mL) over a period of 1 h. The reaction mixture is stirred at room temperature for 20 min. The 1,4-dioxane is evaporated under reduced pressure and the residue dissolved in ether (100 mL). The resulting solution is successively washed with aqueous saturated $NaHCO_3$, water, and brine, dried ($MgSO_4$), filtered and concentrated under reduced pressure. The crude product is purified by flash chromatography ($CH_2Cl_2$:hexane, 7:3) to yield compound 14.1.

b) Compound 14.2

Methyl thioglycolate (379 µL, 4.24 mmol) is added to a solution of compound 14.1 (1.00 g, 4.04 mmol) and $Et_3N$ (619 µL, 4.44 mmol) in $CH_2Cl_2$, and the reaction mixture stirred at room temperature for 1 h. The mixture is diluted with $CH_2Cl_2$ (100 mL), washed successively with aqueous 0.1 N HCl solution, aqueous saturated $NaHCO_3$, water and brine. The organic layer is dried ($MgSO_4$), filtered and concentrated under reduced pressure. The crude product is purified by flash chromatography ($CH_2Cl_2$:acetone, 95:5) to afford compound 14.2.

c) Compound 14.3

To a solution of compound 14.2 (1.07 g, 3.93 mmol) in acetic acid (30 mL) is added at room temperature a solution of bromine (202 μL, 3.93 mmol) in acetic acid (10 mL) over a period of 30 min. The reaction mixture is stirred at room temperature for 30 min and poured in ether (200 mL). The organic phase is successively washed with water, aqueous saturated NaHCO₃, water and brine, dried (MgSO₄), filtered and concentrated under reduced pressure. The crude product is purified by flash chromatography (CH₂Cl₂) to afford compound 14.3.

d) Compound 14.4

Thioformamide (521.3 mg, 8.53 mmol) is added to a solution of compound 14.3 (300.0 mg, 853.1 μmol) in ⁱPrOH (20 mL), then stirred at 60° C. for 1 h and concentrated under reduced pressure. The residue is purified by flash chromatography (CH₂Cl₂:acetone, 95:5) to afford compound 14.4.

e) Compound 14.5

Ester 14.4 (207 mg, 660.9 μmol) is dissolved in DMSO (6.0 mL) and aqueous 1 N NaOH (2.0 mL, 2.0 mmol) solution added. The reaction mixture is stirred at room temperature for 1 h and acidified (pH=2) with TFA. The mixture is then diluted with EtOAc (100 mL) and successively washed with water and brine, dried (MgSO₄), filtered and concentrated under vacuum to give compound 14.5.

f) 2-(4'-(2-(4-(2-chloro-4-methylphenyl)thiazol-5-ylthio)acetamido)biphenyl-4-yl)acetic acid PCl₃ (10.2 μL, 116 μmol) is added to an ice-cold solution of compound 14.5 (35.0 mg, 116 μmol) and compound 2.5 (EXAMPLE 2; 35.4 mg, 128 μmol) in pyridine (3.0 mL). The reaction mixture is stirred at room temperature for 30 min. Water (few drops) is added and the mixture concentrated under reduced pressure.

The crude ester is dissolved in DMSO (3.0 mL) and aqueous 1 N NaOH (1.0 mL, 1.0 mmol) solution added. The reaction mixture is stirred at room temperature for 1 h and acidified (pH=2) with TFA. The solution is purified by RP-HPLC and the pure fractions concentrated to give 2-(4'-(2-(4-(2-chloro-4-methylphenyl)thiazol-5-ylthio)acetamido)biphenyl-4-yl)acetic acid.

Example 15

2-(3'-Chloro-4'-(2-(1-(2-chloro-4-methylphenyl)-1H-pyrazol-5-yloxy)acetamido)biphenyl-4-yl)acetic acid

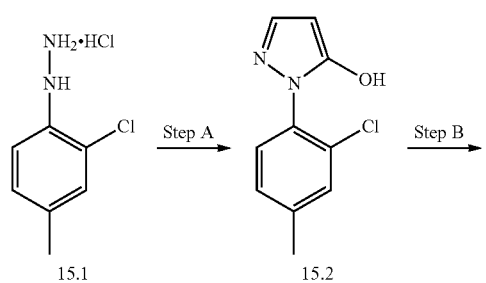

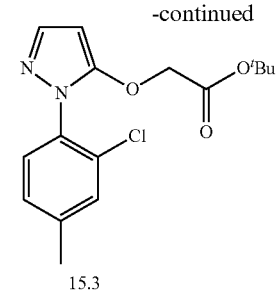

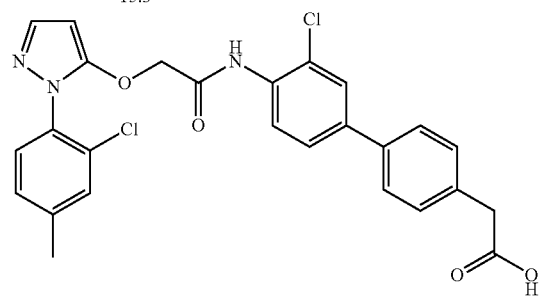

a) Compound 15.2

A mixture of (2-chloro-4-methylphenyl)hydrazine hydrochloride, 15.1, (400 mg, 2.07 mmol) and methyl 3,3dimethoxypropionate (323 μL, 2.28 mmol) in methanol (5.0 mL) is stirred at 70° C. for 24 h, concentrated under reduced pressure and the residue purified by flash chromatography (CH₂Cl₂:acetone, 95:5) to afford compound 15.2.

b) Compound 15.3

To a solution of compound 15.2 (39.4 mg, 188.8 μmol) and tert-butyl bromoacetate (30.7 μL, 207.7 μmol) in DMF (3.0 mL) at room temperature is added potassium carbonate (39.1 mg, 283.3 μmol). The reaction mixture is stirred at room temperature for 16 h, diluted with EtOAc (50 mL) and successively washed with water and brine, dried (MgSO₄), filtered and concentrated under reduced pressure. The crude product is purified by flash chromatography (CH₂Cl₂:acetone, 95:5) to afford compound 15.3.

c) 2-(3'-chloro-4'-(2-(1-(2-chloro-4-methylphenyl)-1H-pyrazol-5-yloxy)acetamido)biphenyl-4-yl)acetic acid TFA (1.00 mL, 13.0 mmol) is added dropwise to a solution of compound 15.3 (13.2 mg, 41.0 μmol) in CH₂Cl₂ (2.0 mL) at room temperature. The reaction mixture is stirred for 16 h and then concentrated under vacuum. PCl₃ (10.2 μL, 116.7 μmol) is added to an ice-cold solution of the resulting acid and compound 2.5 (EXAMPLE 2, 11.3 mg, 41.0 μmol) in pyridine (3.0 mL). The reaction mixture is stirred at room temperature for 30 min. Water (few drops) is added and the mixture concentrated under reduced pressure. The crude ester is dissolved in DMSO (2.0 mL) and aqueous 1 N NaOH (1.0 mL, 1.0 mmol) solution added. The reaction mixture is stirred at room temperature for 1 h and acidified (pH=2) with TFA. The solution is purified by RP-HPLC and the pure fractions concentrated to give 2-(3'-chloro-4'-(2-(1-(2-chloro-4-methylphenyl)-1H-pyrazol-5-yloxy)acetamido)biphenyl-4-yl)acetic acid.

Example 16

2-(3'-Chloro-4'-(2-(1-(2-chloro-4-methylphenyl)-1H-pyrazol-5-ylthio)acetamido)biphenyl-4-yl)acetic acid

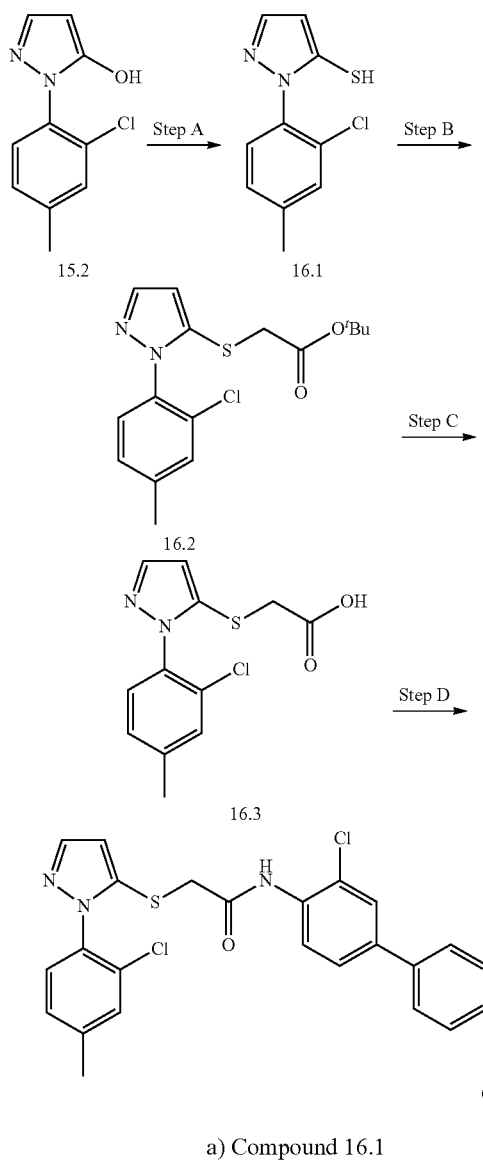

a) Compound 16.1

Compound 15.2 (250 mg, 1.20 mmol) and Lawesson's reagent (485 mg, 1.20 mmol) in toluene (15 mL) is heated under reflux for 4 h, then concentrated under reduced pressure and the residue purified by flash chromatography (CH$_2$Cl$_2$: acetone, 95:5) to afford compound 16.1.

b) Compound 16.2

K$_2$CO$_3$ (105.9 mg, 766.3 µmol) is added To a solution of 16.1 (86.1 mg; 383 µmol) in DMF (5.0 mL) at 0° C., and stirred for 30 min. tert-Butyl bromoacetate (62.2 µL, 421 µmol) is added and the reaction mixture stirred at 0° C. for 1 h and then allowed to warm to room temperature and stirred for 2 h. EtOAc (50 mL) is added and the mixture washed with water and brine, dried (MgSO$_4$), filtered and concentrated under reduced pressure. The residue is purified by flash chromatography (CH$_2$Cl$_2$:acetone, 95:5) to afford compound 16.2.

c) Compound 16.3

TFA (1.00 mL, 13.0 mmol) is added dropwise to a solution of compound 16.2 (58.4 mg, 172.3 µmmol) in CH$_2$Cl$_2$ (3.0 mL) at room temperature and stirred for 16 h, then concentrated under reduced pressure, to afford compound 16.3.

d) 2-(3'-Chloro-4'-(2-(1-(2-chloro-4-methylphenyl)-1H-pyrazol-5-ylthio)acetamido)biphenyl-4-yl)acetic acid PCl$_3$ (10.2 µL, 116.7 µmol) is added to an ice-cold solution of compound 16.3 (29.0 mg, 102.6 µmol) and compound 2.5 (EXAMPLE 2, 32.7 mg, 112.8 µmol) in pyridine (3.0 mL). The reaction mixture is stirred at room temperature for 30 min. Water (few drops) is added and the mixture concentrated under reduced pressure. The crude ester is dissolved in DMSO (3.0 mL) and aqueous 1 N NaOH (1.0 mL, 1.0 mmol) solution added. The reaction mixture is stirred at room temperature for 1 h and acidified (pH=2) with TFA. The solution is purified by RP-HPLC and the pure fractions concentrated to give 2-(3'-chloro-4'-(2-(1-(2-chloro-4-methylphenyl)-1H-pyrazol-5-ylthio)acetamido)biphenyl-4-yl)acetic acid.

Example 17

2-(3'-Chloro-4'-(2-(1-(2-chloro-4-methylphenyl)-1H-1,2,3-triazol-5-ylthio)acetamido)biphenyl-4-yl)acetic acid

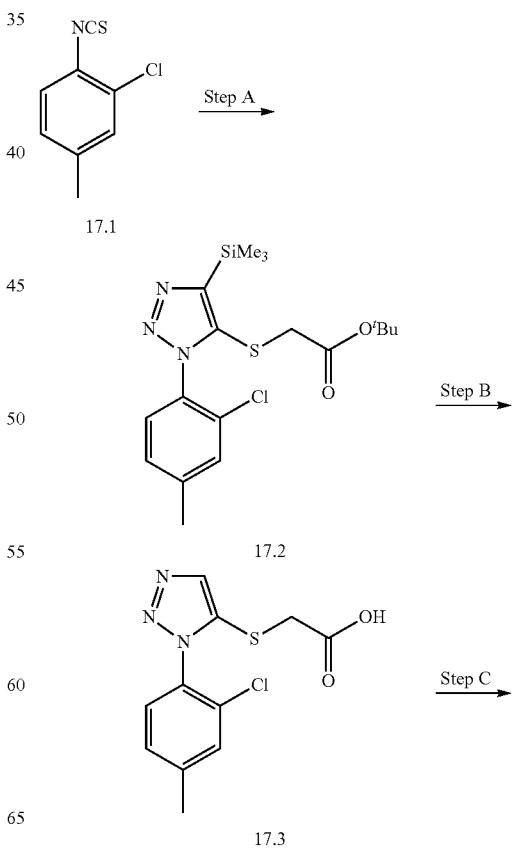

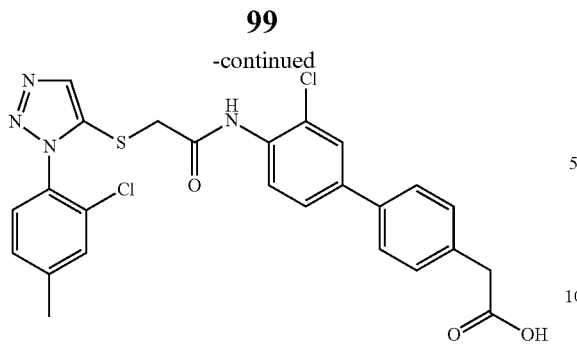

a) Compound 17.2

To a cold (−78° C.) solution of (trimethylsilyl)diazomethane in hexane (2.0 M, 6.53 mL, 13.07 mmol) in THF (50 mL) is added dropwise 2.5 M "BuLi in hexane (5.23 mL, 13.07 mmol). After 20 min, a solution of 2-chloro-1-isothiocyanato-4-methylbenzene, 17.1, (2.0 g, 10.89 mmol) in THF (15 mL) is added dropwise and the reaction mixture stirred at −78° C. for 1 h. tert-Butyl bromoacetate (1.93 mL, 13.07 mmol) is then added and the mixture stirred at −78° C. for 30 min and then at 0° C. for another 30 min. The mixture is treated with ice-water (50 mL) and ether (300 mL) added. The mixture is washed with water and brine, dried (MgSO$_4$), filtered and concentrated under reduced pressure. The crude product is purified by flash chromatography (CH$_2$Cl$_2$:acetone, 95:5) to afford compound 17.2.

b) Compound 17.3

A mixture of compound 17.2 (1.0 g, 2.43 mmol) and aqueous 10% KOH solution (12.5 mL) in methanol (25 mL) is heated under reflux for 2 h. The methanol is removed under reduced pressure and the mixture neutralized with aqueous 1 N HCl solution. The aqueous phase is extracted with ether (2×10 mL) and the combined organic extracts washed with brine, dried (MgSO$_4$), filtered and concentrated under reduced pressure to give compound 17.3.

c) 2-(3'-Chloro-4'-(2-(1-(2-chloro-4-methylphenyl)-1H-1,2,3-triazol-5-ylthio)acetamido)biphenyl-4-yl) acetic acid 2-(3'-Chloro-4'-(2-(1-(2-chloro-4-methylphenyl)-1H-1,2,3-triazol-5-ylthio)acetamido)biphenyl-4-yl)acetic acid is obtained using a method similar to the one described for EXAMPLE 16, Step d.

Example 18

2-(4'-(2-(4-(2-Chloro-4-methylphenyl)-1,2,3-thiadiazol-5-ylthio)acetamido)biphenyl-4-yl)acetic acid

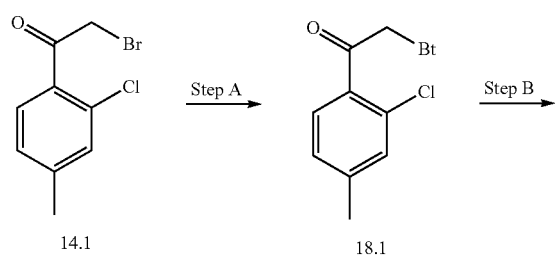

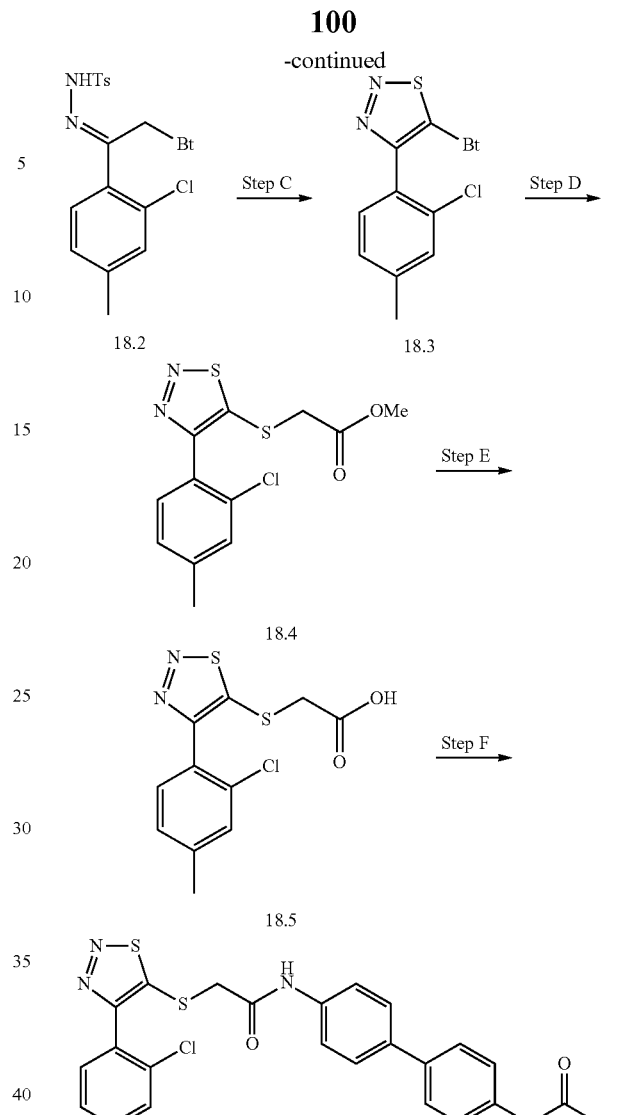

a) Compound 18.1

A mixture of 2-bromo-1-(2-chloro-4-methylphenyl)ethanone, 14.1, (EXAMPLE 14, 1.00 g, 4.04 mmol), benzotriazole (529.4 mg, 4.44 mmol) and K$_2$CO$_3$ (558 mg, 4.04 mmol) in toluene (100 mL) is heated at reflux for 16 h. The cooled reaction mixture is washed with water and brine, dried (MgSO$_4$), filtered, concentrated under reduced pressure, and the residue purified by flash chromatography (CH$_2$Cl$_2$:acetone, 97:3) to afford compound 18.1.

b) Compound 18.2

A solution of compound 18.1 (781 mg, 2.73 mmol) and p-toluenesulfonyl hydrazide (509 mg, 2.73 mmol) in benzene (25.0 mL) is heated at reflux for 24 h. The mixture is cooled and concentrated under reduced pressure to give compound 18.2.

c) Compound 18.3

A solution of compound 18.2 (1.20 g, 2.65 mmol) in SOCl$_2$ (25 mL) is stirred at 60° C. for 8 h. The reaction mixture is then concentrated under reduced pressure and the residue purified by flash chromatography (CH$_2$Cl$_2$) to afford compound 18.3.

d) Compound 18.4

NaH (60% in oil) (33.5 mg, 838 μmol) is added to a solution of compound 18.3 (229 mg, 698 μmol) and methylthioglycolate (74.9 μL, 838 μmol) in DMF (7 mL) at room temperature. The reaction mixture is stirred for 2 h, quenched with aqueous 0.1 N HCl solution (2 mL) and diluted with EtOAc (50 mL). The solution is successively washed with water and brine, dried (MgSO$_4$), filtered, concentrated under reduced pressure, and the residue purified by flash chromatography (hexane: EtOAc, 8:2) to afford compound 18.4.

e) Compound 18.5

Aqueous 1.0 N NaOH solution (800 μL, 800 μmmol) is added to a solution of compound 18.4 (162 mg, 514 μmmol) in DMF (5.0 mL), and stirred at room temperature for 30 min. The mixture is neutralized with aqueous 1.0 N HCl solution (800.0 μL) and diluted with EtOAc (60 mL). The solution is successively washed with water and brine, dried (MgSO$_4$), filtered and concentrated under reduced pressure to give compound 18.5.

f) 2-(4'-(2-(4-(2-Chloro-4-methylphenyl)-1,2,3-thiadiazol-5-ylthio)acetamido)biphenyl-4-yl)acetic acid To a solution of compound 18.5 (75.0 mg, 249 μmol) in CH$_2$Cl$_2$ (5 mL) at room temperature is added (COCl)$_2$ (43.5 μL, 499 μmol) followed by DMF (5 μL). The reaction mixture is stirred for 15 min and concentrated under reduced pressure. The resulting acyl chloride is dissolved in THF (3 mL) and a solution of compound 2.5 (EXAMPLE 2, 82.5 mg, 299 μmol) in THF (2 mL) is added followed by pyridine (60.5 μL, 748 μmol). The reaction mixture is stirred for 10 min and then quenched with a few drops of aqueous 0.1 N HCl solution. The reaction mixture is then concentrated under reduced pressure. The intermediate ester is diluted in DMSO (6 mL) and treated with aqueous 1.0N NaOH solution (1.0 mL, 1.0 mmol). The reaction mixture is stirred for 3 h and then neutralized with TFA. The solution is purified by RP-HPLC and the pure fractions concentrated to give 2-(4'-(2-(4-(2-Chloro-4-methylphenyl)-1,2,3-thiadiazol-5-ylthio)acetamido)biphenyl-4-yl)acetic acid.

Example 19

2-(4'-(2-(5-(2-Chloro-4-methylphenyl)-1-methyl-1H-pyrazol-4-ylthio)acetamido)biphenyl-4-yl)acetic acid

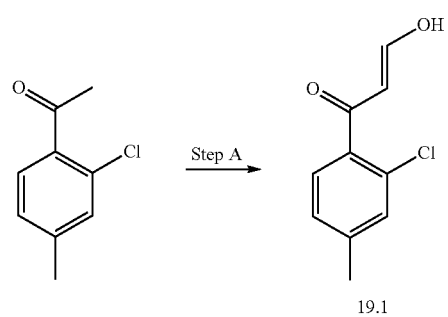

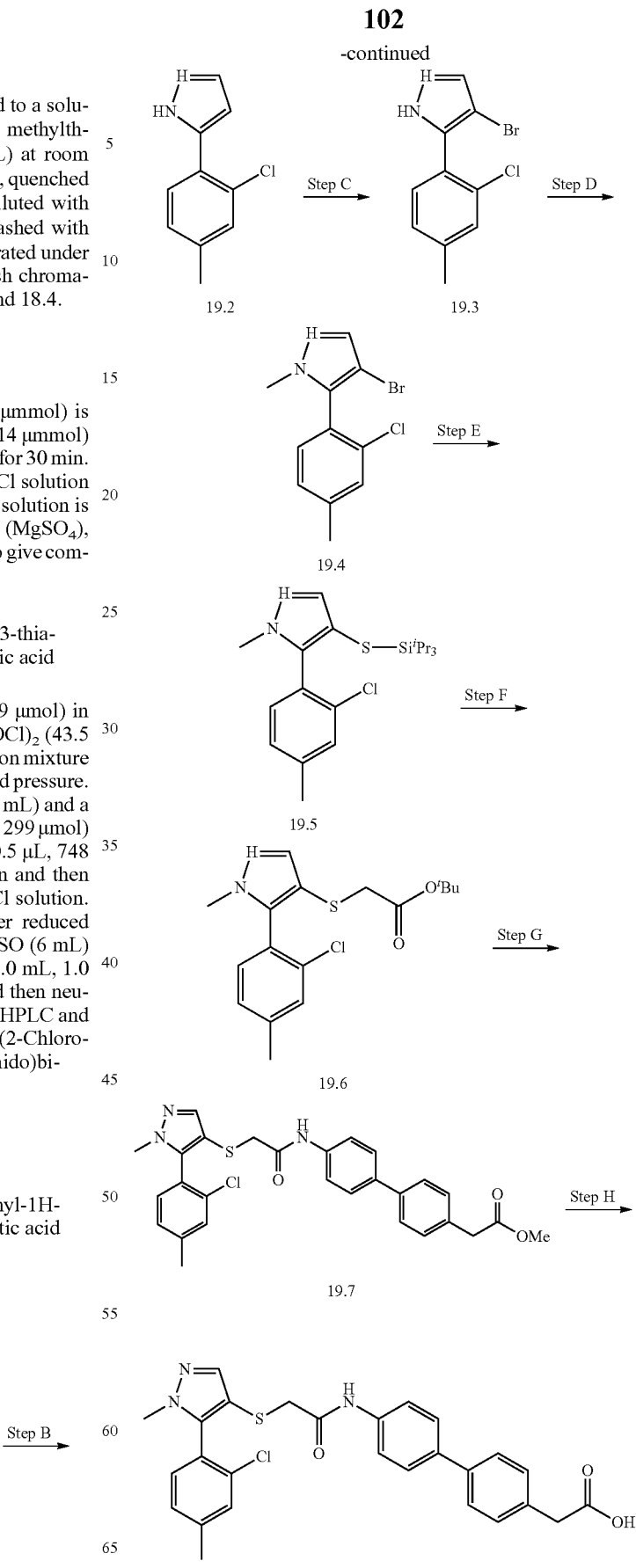

a) Compound 19.1

To a suspension of MeONa (384 mg, 7.12 mmol) in THF (18 mL) at room temperature is added ethyl formate (574.9 µL, 7.12 mmol) followed by a solution of 2-chloro-4-methylacetophenone (1.00 g, 5.93 mmol) in THF (6.0 mL). The reaction mixture is stirred at room temperature for 16 h, and then aqueous 1.0 N NaOH solution (60 mL) added. The aqueous phase is washed with ether (2×2 mL, extracts discarded), and the aqueous phase acidified with aqueous 1.0 N HCl solution (65 mL). The aqueous phase is then extracted with ether (3×40 mL), and the combined organic extracts washed with water and brine, dried (MgSO$_4$), filtered, and concentrated under reduced pressure to give compound 19.1.

b) Compound 19.2

Hydrazine hydrate (193.2 µL, 6.20 mmol) is added dropwise to a cold (0° C.) solution of compound 19.1 (1.11 g, 5.64 mmol) in ethanol (15.0 mL). The cooling bath is removed and the reaction mixture stirred at room temperature for 3 h. The mixture is concentrated under reduced pressure, the residue diluted in CH$_2$Cl$_2$ (150 mL), and the solution washed with brine, dried (MgSO$_4$), filtered and concentrated under reduced pressure. The crude product is purified by flash chromatography (CH$_2$Cl$_2$:acetone, 95:5) to afford compound 19.2.

c) Compound 19.3

A solution of bromine (198 µL, 3.83 mmol) in CH$_2$Cl$_2$ (10 mL) is added dropwise to a solution of compound 19.2 (671 mg, 3.48 mmol) in CH$_2$Cl$_2$ (20 mL) and stirred at room temperature for 1 h. The mixture is diluted with CH$_2$Cl$_2$ (60 mL) and successively washed with water, aqueous saturated NaHCO$_3$ solution and brine, dried (MgSO$_4$), filtered and concentrated under reduced pressure. The crude product is purified by flash chromatography (CH$_2$Cl$_2$ acetone, 95:5) to afford compound 19.3.

d) Compound 19.4

NaH (60% in oil) (59.9 mg, 1.50 mmol) is added to a cold (0° C.) solution of compound 19.3 (369.6 mg, 1.36 mmol) in DMF (5 mL). The reaction mixture is stirred at 0° C. for 30 min and then MeI (93.2 µL, 1.50 mmol) added. The mixture is warmed to room temperature and stirred for 1 h. The reaction mixture is diluted with EtOAc (100 mL) and washed with water and brine, dried (MgSO$_4$), filtered and concentrated under reduced pressure. The crude product is purified by flash chromatography (CH$_2$Cl$_2$:acetone, 95:5) to afford compound 19.4.

e) Compound 19.5

To a cold (−78° C.) solution of compound 19.4 (75.0 mg, 262 µmol) in THF (4 mL) is added 2.5 M "BuLi in hexane (115.6 µL, 288.9 µmol). After 15 min, a solution of ($^i$Pr$_3$SiS)$_2$ (199.0 mg, 525.3 µmol) in THF (1 mL) is added via cannula to the reaction mixture at −78° C. The reaction mixture is stirred for 15 min, the cooling bath removed and the solution stirred for 3 h. CH$_2$Cl$_2$ (50 mL) is added and the mixture washed with water and brine, dried (MgSO$_4$), filtered and concentrated under reduced pressure to afford compound 19.5.

f) Compound 19.6

TBAF (1.0 M in THF) (294 µL, 294 µmol) is added to a solution of compound 19.5 (46.4 mg, 117 µmol) and tert-butyl bromoacetate (43.4 µL, 294 µmol) in DMF (3 mL). The reaction mixture is stirred for 30 min, quenched with water (10 mL), and diluted with EtOAc (60 mL). The organic phase is washed with water and brine, dried (MgSO$_4$), filtered and concentrated under reduced pressure. The crude product is purified by flash chromatography (CH$_2$Cl$_2$:acetone, 95:5) to afford compound 19.6.

g) Compound 19.7

TFA (1.0 mL, 13.0 mmol) is added dropwise to a solution of compound 19.6 (34.8 mg, 98.6 µmol) in CH$_2$Cl$_2$ (2 mL) at room temperature. The reaction mixture is stirred for 8 h and then concentrated under reduced pressure. The intermediate acid is diluted in CH$_2$Cl$_2$ (5 mL) and (COCl)$_2$ (25.8 µL, 295.8 µmol) is added followed by DMF (5 µL). The reaction mixture is stirred for 15 min and CH$_2$Cl$_2$ removed under reduced pressure. The intermediate acyl chloride is dissolved in THF (3 mL) and a solution of compound 2.5 (EXAMPLE 2, 40.8 mg, 147.9 µmol) in THF (1 mL) added followed by pyridine (23.9 µL, 295.8 µmol). The reaction mixture is stirred for 1 h and then concentrated under reduced pressure to give compound 19.7.

h) 2-(4'-(2-(5-(2-Chloro-4-methylphenyl)-1-methyl-1H-pyrazol-4-ylthio)acetamido)biphenyl-4-yl)acetic acid Ester 19.7 (50 mg, 90 µmol) is dissolved in DMSO (4 mL) and aqueous 1 N NaOH (500 µL, 500 µmol) solution added. The reaction mixture is stirred at room temperature for 1 h and then acidified (pH=2) with TFA. The solution is purified by RP-HPLC and the pure fractions containing the desired isomer (slowest eluting isomer) are concentrated to give 2-(4'-(2-(5-(2-chloro-4-methylphenyl)-1-methyl-1H-pyrazol-4-ylthio)acetamido)biphenyl-4-yl)acetic acid.

Example 20

2-(3'-Chloro-4'-(2-(1-(2-chloro-4-methylphenyl)-5-methyl-1H-imidazol-2-ylthio)acetamido) biphenyl-4-yl)acetic acid

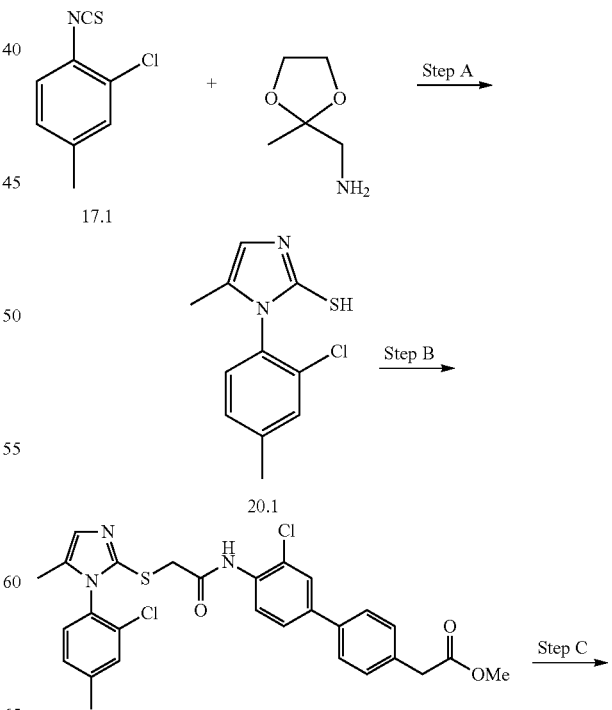

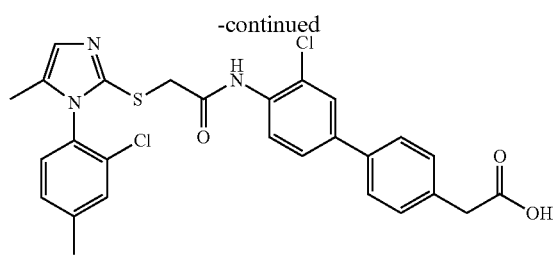

a) Compound 20.1

1-Amino-2,2-ethylenedioxypropane (2.00 g, 17.0 mmol) is added to a cooled (0° C.) solution of compound 17.1 (EXAMPLE 17, 3.17 g, 17.1 mmol) in ethanol (14 mL). The reaction mixture is stirred at reflux for 30 min and then cooled to 0° C. (product precipitated as a white solid). Aqueous 12 N HCl solution (1.4 mL) is added and the mixture again heated under reflux for 1 h (solution after heating). The solution is cooled to room temperature and the precipitate collected by suction filtration to give compound 20.1 (2.01 g, 49% yield) as a white solid.

b) Compound 20.2

To a solution of compound 20.1 (90.3 mg, 378 μmol) in DMF (5 mL) is added $K_2CO_3$ (157 mg, 1.13 mmol) followed by the methyl ester analog of compound 2.6 (EXAMPLE 2, 150 mg, 378 μmol). The reaction mixture is stirred at room temperature for 2 h, diluted with EtOAc (100 mL), successively washed with water and brine, dried ($MgSO_4$), filtered and concentrated under reduced pressure. The crude product is purified by flash chromatography ($CH_2Cl_2$:acetone, 95:5) to afford compound 20.2.

c) 2-(3'-Chloro-4'-(2-(1-(2-chloro-4-methylphenyl)-5-methyl-1H-imidazol-2-ylthio)acetamido) biphenyl-4-yl)acetic acid 2-(3'-Chloro-4'-(2-(1-(2-chloro-4-methylphenyl)-5-methyl-1H-imidazol-2-ylthio)acetamido) biphenyl-4-yl)acetic acid is obtained using a method similar to the one described in EXAMPLE 19, Step h.

Example 21

2-(3'-Chloro-4'-(2-(4-(2-chloro-4-methylphenyl)-1H-pyrazol-5-ylthio)acetamido)biphenyl-4-yl)acetic acid

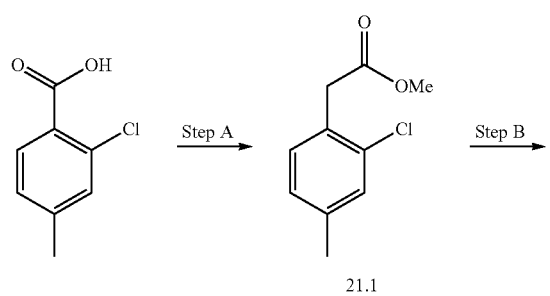

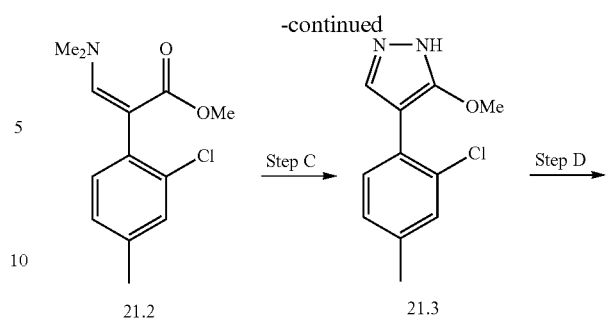

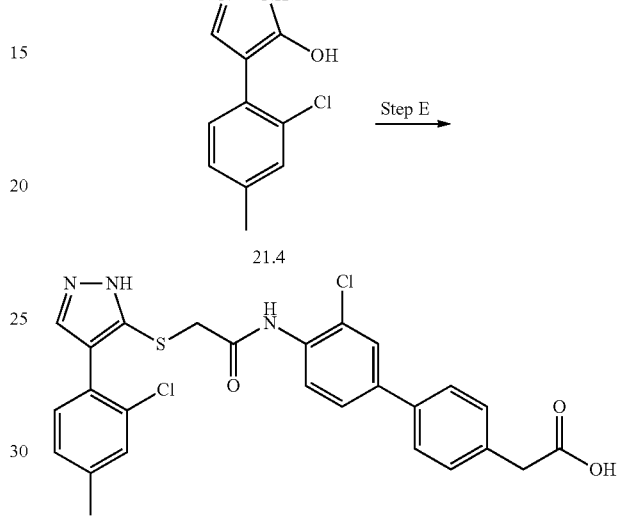

a) Compound 21.1

To a solution of 2-chloro-4-methylbenzoic acid (3.21 g, 18.8 mmol) in $CH_2Cl_2$ (80 mL) at room temperature is added $(COCl)_2$ (3.28 mL, 37.6 mmol) followed by DMF (100 μL). The reaction mixture is stirred for 3 h then concentrated under reduced pressure. The intermediate acyl chloride is dissolved in THF (40 mL) and added dropwise to a cold (0° C.) solution of $CH_2N_2$ in ether (ca. 0.6 M, 75 mL). The reaction mixture is stirred at room temperature for 4 h. The solvent is then carefully removed under reduced pressure and the residue dissolved in methanol (100.0 mL). $Ag_2O$ (4.35 g, 18.8 mmol) is added to the solution and the reaction mixture stirred at 0° C. for 1 h and then heated at 60° C. for 2 h. The reaction mixture is then cooled to room temperature and filtered through diatomaceous earth. The filtrate is concentrated under vacuum and the residue purified by flash chromatography (hexane:EtOAc, 8:2) to afford compound 21.1.

b) Compound 21.2 tert-Butoxybis(dimethylamino)methane (685 μL, 3.32 mmol) is added to a solution of compound 21.1 (589 mg, 2.96 mmol) in THF (7 mL) at room temperature. The reaction mixture is stirred at room temperature for 2 h then concentrated under reduced pressure, and the resulting residue purified by flash chromatography (hexane:EtOAc, 1:1) to afford compound 21.2.

c) Compound 21.3

Hydrazine monohydrate (113 μL, 2.33 mmol) is added to a solution of compound 21.2 (538 mg, 2.12 mmol) in ethanol (5 mL), stirred at reflux for 3 h and concentrated under reduced pressure to give compound 21.3.

d) Compound 21.4

BBr$_3$ (1.0 M in CH$_2$Cl$_2$, 8.12 mL, 8.12 mmol) is added to a cold (0° C.) solution of compound 21.3 (452.3 mg, 2.03 mmol) in CH$_2$Cl$_2$ (20.0 mL). The reaction mixture is heated to room temperature and stirred for 3 h. The mixture is then cooled to 0° C. and quenched with methanol (5 mL). The solution is diluted with CH$_2$Cl$_2$ (100 mL) and successively washed with water, aqueous saturated NaHCO$_3$ and brine, dried (MgSO$_4$), filtered and concentrated under reduced pressure to give compound 21.4.

e) 2-(3'-Chloro-4'-(2-(4-(2-chloro-4-methylphenyl)-1H-pyrazol-5-ylthio)acetamido)biphenyl-4-yl)acetic acid To a solution of compound 21.4 (60.0 mg, 287.6 μmol) in DMF (5 mL) at room temperature is added CsCO$_3$ (281.1 mg, 862.7 μmol) followed by compound 2.6 (EXAMPLE 2, 114.1 mg, 287.6 μmol). The reaction mixture is stirred at 50° C. for 2 h, filtered through diatomaceous earth and to the filtrate is added aqueous 1 N NaOH solution (1.0 mL, 1.0 mmol). The reaction mixture is stirred at room temperature for 30 min, acidified (pH=2) with TFA and purified by RP-HPLC. The pure fractions are concentrated to give 2-(3'-chloro-4'-(2-(4-(2-chloro-4-methylphenyl)-1H-pyrazol-5-ylthio)acetamido)biphenyl-4-yl)acetic acid.

Example 22

4-(3-Chloro-4-(2-(4-(2-chloro-4-methylphenyl)-5-methyl-1H-pyrazol-3-yloxy)acetamido)phenyl)-2,2-dimethylbut-3-ynoic acid

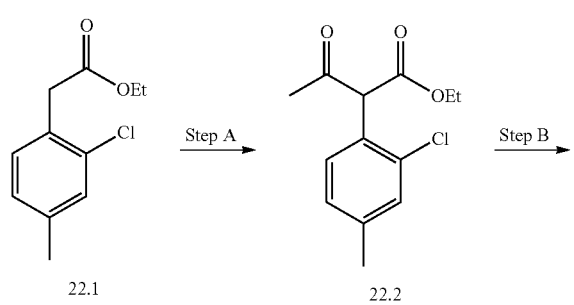

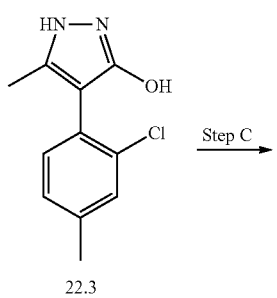

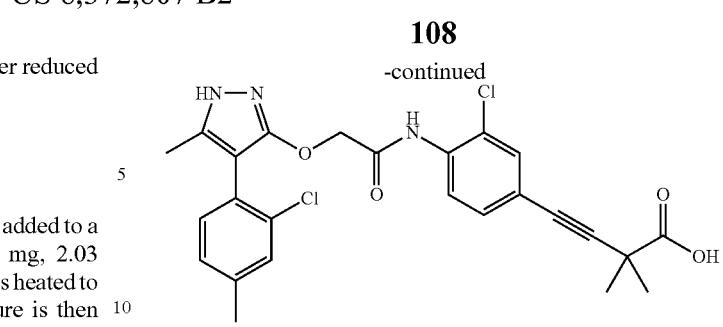

a) Compound 22.2

To a cold (−78° C.) solution of ethyl 2-(2-chloro-4-methylphenyl)acetate, 22.1, (2.50 g, 11.8 mmol) in THF (50 mL) is added 1.0 M LiHMDS in hexane (24.7 mL, 24.7 mmol). The reaction mixture is stirred at −78° C. for 1 h and then acetic anhydride (1.33 mL, 14.1 mmol) added dropwise. The reaction mixture is warmed to room temperature and stirred for 30 min. The mixture is then poured in aqueous 1 N HCl solution (50 mL), and extracted with EtOAc (2×50 mL). The organic extracts are washed with water, brine, dried (MgSO$_4$), filtered and concentrated under vacuum. The crude product is purified by flash chromatography (hexane:EtOAc, 8:2) to afford compound 22.2.

b) Compound 22.3

Hydrazine hydrate (122 μL, 3.93 mmol) is added to a solution of compound 22.2 (500 mg, 1.96 mmol) in ethanol (3.0 mL) and stirred under reflux for 2 h. The reaction mixture is then cooled to room temperature and the white precipitate collected under suction filtration to give compound 22.3.

c) 4-(3-chloro-4-(2-(4-(2-chloro-4-methylphenyl)-5-methyl-1H-pyrazol-3-yloxy)acetamido)phenyl)-2,2-dimethylbut-3-ynoic acid 4-(3-chloro-4-(2-(4-(2-chloro-4-methylphenyl)-5-methyl-1H-pyrazol-3-yloxy)acetamido)phenyl)-2,2-dimethylbut-3-ynoic acid is obtained using a method analogous to the one described in EXAMPLE 2, Step g.

Example 23

4-(3-Chloro-4-(2-(4-(2-chloro-4-cyclopropylphenyl)-5-(trifluoromethyl)-4H-1,2,4-triazol-3-ylthio)acetamido)phenyl)-2,2-dimethylbut-3-ynoic acid

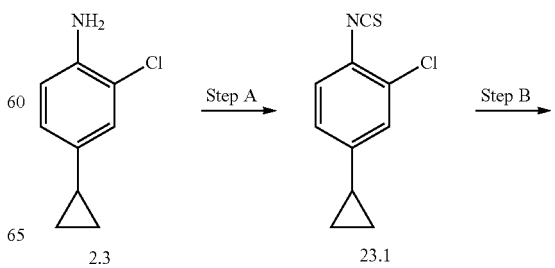

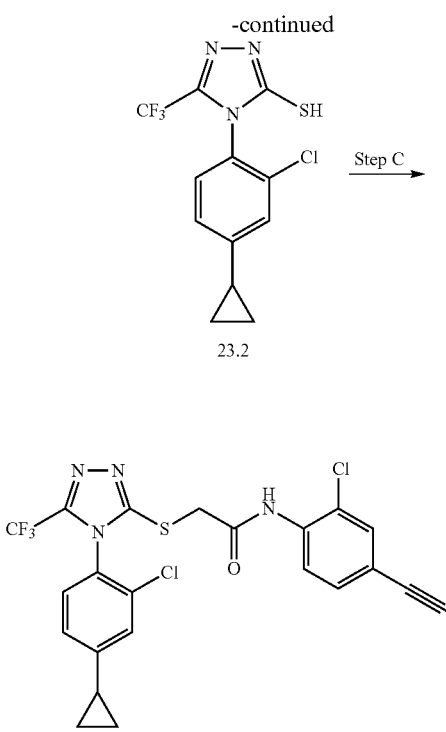

a) Compound 23.1

To a solution of 2-chloro-4-cyclopropylaniline, 2.3, (EXAMPLE 2, 600 mg, 3.58 mmol) in acetonitrile (15 mL) at room temperature is added Et$_3$N (1.1 mL, 7.9 mmol) and thiophosgene (300 µL, 3.94 mmol). The reaction mixture is stirred at room temperature for 3 h, diluted with EtOAc (100 mL), successively washed with water and brine, dried (MgSO$_4$), filtered and concentrated under reduced pressure to afford compound 23.1.

b) Compound 23.2

To a solution of compound 23.1 (150 mg, 715 µmol) in ethanol (15. mL) is added trifluoroacetylhydrazine (101 mg, 787 µmol) and the reaction mixture stirred at reflux for 2 h. The mixture is then concentrated under reduced pressure and the residue diluted with TFA (10 mL). The mixture is stirred at reflux for 2 h then excess TFA removed under reduced pressure. The mixture is diluted with EtOAc (50 mL) and successively washed with saturated aqueous NaHCO$_3$, water and brine, dried (MgSO$_4$), filtered and concentrated under reduced pressure. The crude product is purified by flash chromatography (CH$_2$Cl$_2$:acetone, 9:1) to afford compound 23.2.

c) 4-(3-Chloro-4-(2-(4-(2-chloro-4-cyclopropylphenyl)-5-(trifluoromethyl)-4H-1,2,4-triazol-3-ylthio)acetamido) phenyl)-2,2-dimethylbut-3-ynoic acid 4-(3-Chloro-4-(2-(4-(2-chloro-4-cyclopropylphenyl)-5-(trifluoromethyl)-4H-1,2,4-triazol-3-ylthio)acetamido) phenyl)-2,2-dimethylbut-3-ynoic acid is obtained using a method analogous to the one described in EXAMPLE 22, Step c.

Example 24

2-Methyl-2-(1-(naphthalen-1-yl)-1H-pyrazol-5-yloxy)propanoic acid

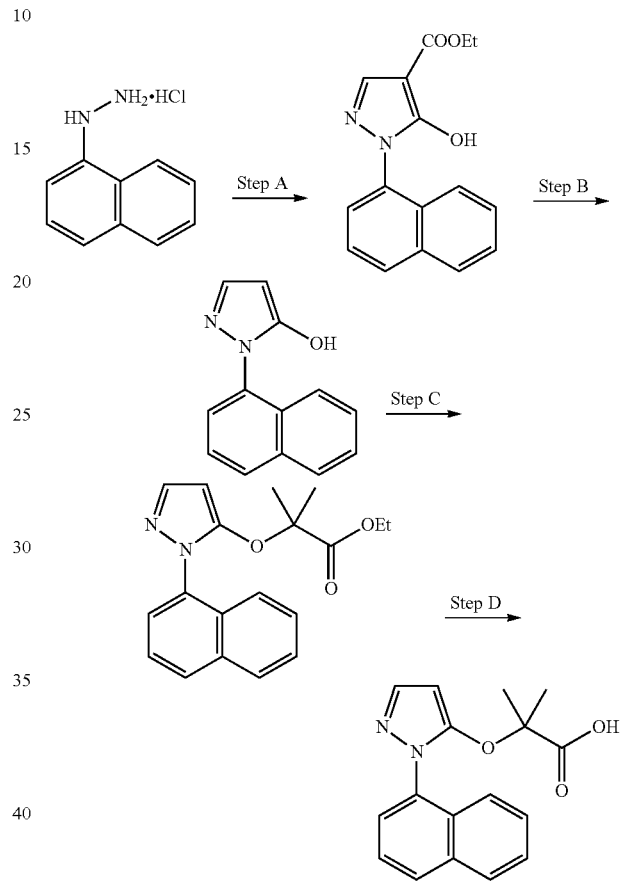

Step A: Ethyl 5-hydroxy-1-(naphthalen-1-yl)-1H-pyrazole-4-carboxylate

To a mixture of naphthalen-1-ylhydrazine hydrochloride (1 g, 5.1 mmol) and potassium carbonate (1.4 g, 10.3 mmol) in water (30 mL) was added diethyl ethoxymethylenemalonate (1.1 g, 5.1 mmol) at room temperature. The reaction mixture was stirred for 3 hours at room temperature and then extracted with ethyl acetate. The aqueous layer was acidified with 1N HCl to pH 2 and then extracted with ethyl acetate again. This organic layer was dried over sodium sulfate and concentrated to give ethyl 5-hydroxy-1-(naphthalen-1-yl)-1H-pyrazole-4-carboxylate as a solid.

Step B: 1-(Naphthalen-1-yl)-1H-pyrazol-5-ol

A mixture of ethyl 5-hydroxy-1-(naphthalen-1-yl)-1H-pyrazole-4-carboxylate (480 mg, 1.8 mmol), aqueous potassium hydroxide solution (35%, 2.2 mL, 13.5 mmol) and methanol (5 mL) was heated to reflux for 24 hours. The reaction mixture was then cooled to 0° C., acidified to pH 2 with conc. HCl and refluxed for additional 12 hours to complete decarboxylation. The reaction was then cooled to room temperature and concentrated. The residue was taken up in water and extracted with ethyl acetate, the organic layer washed with water, dried over sodium sulfate and concentrated. Purification by preparative TLC (95% dichloromethane/5% methanol) afforded 1-(naphthalen-1-yl)-1H-pyrazol-5-ol.

Step C: Ethyl 2-methyl-2-(1-(naphthalen-1-yl)-1H-pyrazol-5-yloxy)propanoate

A mixture of 1-(naphthalen-1-yl)-1H-pyrazol-5-ol (250 mg, 1.2 mmol), ethyl bromoisobutyrate (0.2 mL, 1.3 mmol) and potassium carbonate (318 mg, 1.3 mmol) in DMF (3 mL) was stirred at room temperature for 16 hours. Water was then added to the reaction mixture, extracted with ethyl acetate, dried over sodium sulfate and concentrated. Purification by preparative thin layer chromatography (95% dichloromethane/5% methanol) afforded ethyl 2-methyl-2-(1-(naphthalen-1-yl)-1H-pyrazol-5-yloxy)propanoate as a solid.

Step D: 2-Methyl-2-(1-(naphthalen-1-yl)-1H-pyrazol-5-yloxy)propanoic acid

A mixture of ethyl 2-methyl-2-(1-(naphthalen-1-yl)-1H-pyrazol-5-yloxy)propanoate (80 mg, 0.25 mmol), aqueous sodium hydroxide solution (10%, 5 mL) and methanol (5 mL) was stirred at reflux for 2 hours. The reaction was then cooled to room temperature and the methanol removed. Water was added, neutralized with 1N HCl and extracted with ethyl acetate. The organic layer was dried over sodium sulfate and concentrated. Purification by preparative thin layer chromatography (95% dichloromethane/5% methanol) afforded 2-Methyl-2-(1-(naphthalen-1-yl)-1H-pyrazol-5-yloxy)propanoic acid as a solid. $^1$H NMR (DMSO-$d_6$, 400 MHz): δ 13.4 (s, 1H), 8.09 (m, 2H), 7.65 (m, 6H), 5.78 (d, 1H), 1.37 (s, 6H).

Example 25

2-Methyl-2-(1-(naphthalen-1-yl)-1H-pyrazol-5-ylthio)propanoic acid

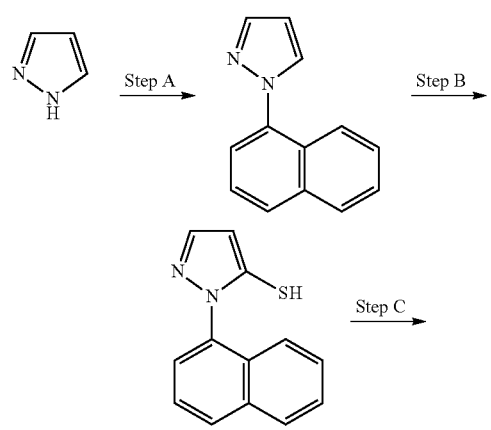

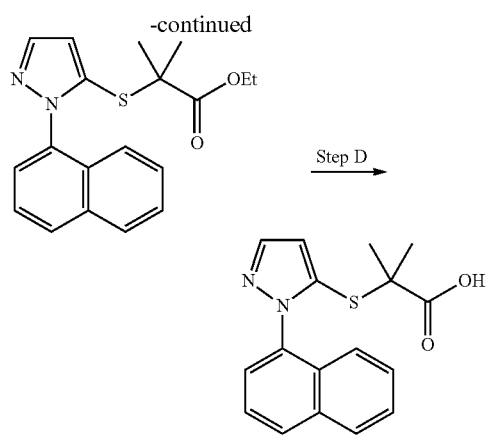

Step A: 1-(Naphthalen-1-yl)-1H-pyrazole

A mixture of 1H-pyrazole (300 mg, 4.4 mmol), iodonaphthalene (1.1 g, 4.4 mmol), copper (I) iodide (126 mg, 0.66 mmol), $Cs_2CO_3$ (2.15 g, 6.6 mmol) in DMF (5 mL) was evacuated and filled with nitrogen twice. The reaction was then stirred at room temperature for 30 minutes and then at 120° C. for 2 days. The reaction mixture was then cooled to room temperature, diluted with ethyl acetate, filtered through silica gel and concentrated to give 1-(naphthalen-1-yl)-1H-pyrazole as pure solid. (800 mg, 93%).

Step B: 1-(Naphthalen-1-yl)-1H-pyrazole-5-thiol

To a solution of 1-(Naphthalen-1-yl)-1H-pyrazole (796 mg, 4.1 mmol) in THF (7 mL) at −78° C. was added n-BuLi (1.6M hexanes, 2.8 mL, 4.5 mmol) and the mixture was stirred at −78° C. for 30 minutes. Sulfur was then added (145 mg, 4.5 mmol) and the mixture was allowed to warm to ° C. and stirred for 7 hours at 0° C. Saturated aqueous ammonium chloride and 10% aqueous HCl was added and the mixture extracted with ethyl acetate. The organic layer was then extracted with a 5% aqueous potassium carbonate solution; the aqueous layer acidified with 10% HCl and extracted with ethyl acetate. The organic layer was dried over sodium sulfate and concentrated to give 1-(naphthalen-1-yl)-1H-pyrazole-5-thiol as a solid.

Step C: Ethyl 2-methyl-2-(1-(naphthalen-1-yl)-1H-pyrazol-5-ylthio)propanoate A mixture of 1-(naphthalen-1-yl)-1H-pyrazole-5-thiol (120 mg, 0.53 mmol), ethyl bromoisobutyrate (0.09 mL, 0.58 mmol) and potassium carbonate (81 mg, 0.58 mmol) in DMF (3 mL) was stirred at room temperature for 16 hours. Water was then added to the reaction mixture, extracted with ethyl acetate, dried over sodium sulfate and concentrated. Purification by preparative thin layer chromatography (95% dichloromethane/5% acetone) afforded ethyl 2-methyl-2-(1-(naphthalen-1-yl)-1H-pyrazol-5-ylthio)propanoate as a solid. (124 mg, 69%).

Step D: 2-Methyl-2-(1-(naphthalen-1-yl)-1H-pyrazol-5-ylthio)propanoic acid

A mixture of ethyl 2-methyl-2-(1-(naphthalen-1-yl)-1H-pyrazol-5-ylthio)propanoate (124 mg, 0.36 mmol), aqueous sodium hydroxide solution (10%, 5 mL) and methanol (5 mL)

was stirred at reflux for 2 hours. The reaction was then cooled to room temperature and the methanol removed. Water was added, neutralized with 1N HCl and extracted with ethyl acetate. The organic layer was dried over sodium sulfate and concentrated. Purification by preparative thin layer chromatography (95% dichloromethane/5% methanol) afforded 2-methyl-2-(1-(naphthalen-1-yl)-1H-pyrazol-5-ylthio)propanoic acid as a solid.

$^1$H NMR (DMSO-$d_6$, 400 MHz): δ 13.2 (s, 1H), 8.14 (m, 2H), 7.91 (s, 1H), 7.69 (m, 4H), 7.09 (d, J=8.3 Hz, 1H), 6.79 (s, 1H), 1.21 (s, 6H).

Example 26

2-methyl-2-(5-methyl-4-(naphthalen-1-yl)-1H-pyrazol-3-yloxy)propanoic acid

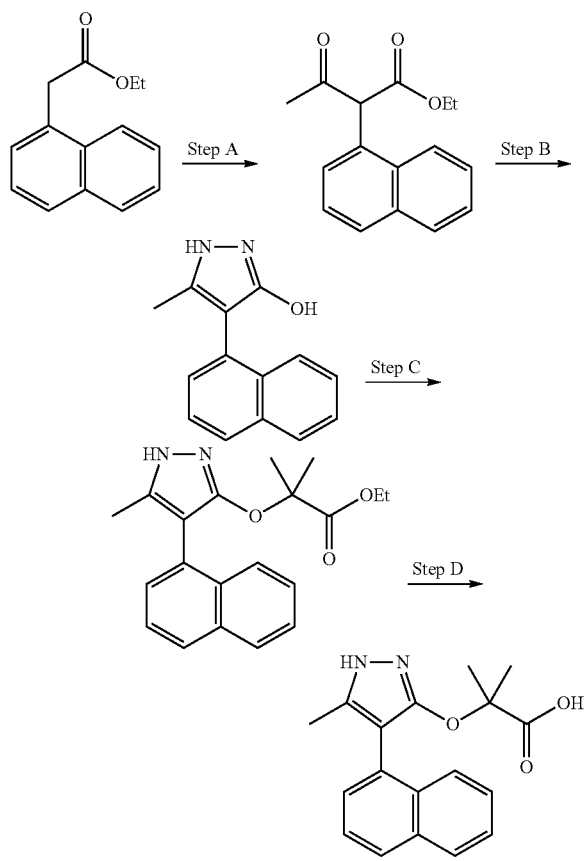

Step A: Ethyl 2-(naphthalen-1-yl)-3-oxobutanoate

To a solution of ethyl 2-(naphthalen-1-yl)acetate (1 g, 4.7 mmol) in tetrahydrofuran (20 mL) at −78° C. was added LiHMDS (1M THF, 9.4 mL, 9.4 mmol) and the reaction mixture stirred at −78° C. for 1 hour. Acetic anhydride was then added (0.54 mL, 5.64 mmol) dropwise and the reaction allowed to warm to room temperature and stirred for 30 minutes. Aqueous HCl solution (1N, 25 mL) was added to the reaction mixture and then extracted with ethyl acetate, dried over sodium sulfate and concentrated to give compound ethyl 2-(naphthalen-1-yl)-3-oxobutanoate as a light yellow oil, that was used in the next step without further purification.

Step B: 5-Methyl-4-(naphthalen-1-yl)-1H-pyrazol-3-ol

A mixture of ethyl 2-(naphthalen-1-yl)-3-oxobutanoate (500 mg, 1.95 mmol) and hydrazine hydrate (0.122 mL, 3.9 mmol) in ethanol (3 mL) was stirred at reflux for 2 hours. The reaction mixture was then cooled to room temperature and concentrated to give compound methyl-4-(naphthalen-1-yl)-1H-pyrazol-3-ol as an oil that solidified upon standing (400 mg, 91%). The crude product was used in next step without further purification.

Step C: Ethyl 2-methyl-2-(5-methyl-4-(naphthalen-1-yl)-1H-pyrazol-3-yloxy)propanoate A mixture of 5-methyl-4-(naphthalen-1-yl)-1H-pyrazol-3-ol (200 mg, 0.89 mmol), ethyl bromoisobutyrate (0.14 mL, 0.89 mmol) and potassium carbonate (136 mg, 0.98 mmol) in DMF (3 mL) was stirred at room temperature for 16 hours. Water was then added to the reaction mixture, extracted with ethyl acetate, dried over sodium sulfate and concentrated. Purification by preparative thin layer chromatography (95% dichloromethane/5% methanol) afforded compound ethyl 2-methyl-2-(5-methyl-4-(naphthalen-1-yl)-1H-pyrazol-3-yloxy)propanoate as a solid.

Step D: 2-methyl-2-(5-methyl-4-(naphthalen-1-yl)-1H-pyrazol-3-yloxy)propanoic acid A mixture of ethyl 2-methyl-2-(5-methyl-4-(naphthalen-1-yl)-1H-pyrazol-3-yloxy)propanoate (60 mg, 0.18 mmol), aqueous sodium hydroxide solution (10%, 5 mL) and methanol (5 mL) was stirred at reflux for 2 hours. The reaction was then cooled to room and the methanol removed. Water was added, neutralized with aqueous HCl solution (1N) and extracted with ethyl acetate. The organic layer was dried over sodium sulfate and concentrated. Purification by preparative thin layer chromatography (95% dichloromethane/5% methanol) afforded compound 2-methyl-2-(5-methyl-4-(naphthalen-1-yl)-1H-pyrazol-3-yloxy)propanoic acid as a solid (40 mg, 71%).

$^1$H NMR (DMSO-$d_6$, 400 MHz): δ 13.0 (s, 1H), 12.2 (s, 1H), 8.3 (d, J=8.0 Hz, 1H), 7.90 (d, J=7.8 Hz, 1H), 7.82 (d, J=8.1 Hz, 1H), 7.5 (m, 4H), 2.0 (s, 3H), 1.37 (s, 6H).

Example 27

2-(1-(naphthalen-1-yl)-4-(trimethylsilyl)-1H-1,2,3-triazol-5-ylthio)acetic acid

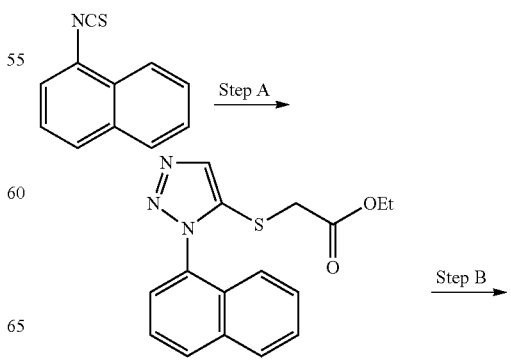

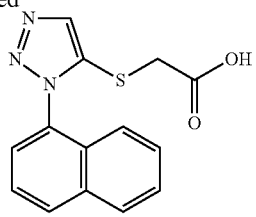

Step A: To a solution of (trimethylsilyl)diazomethane in hexane (2M, 1.74 mL, 3.5 mmol) in tetrahydrofuran (10 mL) at −78° C. was added dropwise n-BuLi and the mixture was stirred at −78° C. for 1 hour. Isothiocyanatobenzene (500 mg, 2.9 mmol) in THF (4 mL) was added and the mixture was stirred at −78° C. for 1 hour. Ethyl bromoacetate (484 mg, 2.9 mmol) was then added and the mixture was stirred at −78° C. for 30 min. and then at 0° C. for additional 30 min. Iced water was added to the reaction and the mixture was extracted with ether. The organic layer was dried over sodium sulfate and concentrated under reduced pressure to give ethyl 2-(1-(naphthalen-1-yl)-4-(trimethylsilyl)-1H-1,2,3-triazol-5-ylthio)acetate as a yellow oil, that was used in the next step without further purification (1 g, 89%).

Step B: A mixture of compound ethyl 2-(1-(naphthalen-1-yl)-4-(trimethylsilyl)-1H-1,2,3-triazol-5-ylthio)acetate (1 g, 2.6 mmol), aqueous sodium hydroxide solution (10%, 12 mL) and methanol (20 mL) was stirred at reflux for 2 hours. The reaction mixture was then cooled to room temperature and concentrated to a reduced volume. Water was added, the reaction neutralized with aqueous HCl solution (1N) and extracted with ethyl acetate. The organic layer was dried over sodium sulfate and concentrated under reduced pressure to give 2-(1-(naphthalen-1-yl)-4-(trimethylsilyl)-1H-1,2,3-triazol-5-ylthio)acetic acid as a solid.

$^1$H NMR (DMSO-$d_6$, 400 MHz): δ 13.1 (s, 1H), 8.22 (d, J=7.6 Hz, 1H), 8.18 (d, J=8.1 Hz, 1H), 8.11 (s, 1H), 7.78 (m, 2H), 7.68 (m, 1H), 7.62 (m, 1H), 7.13 (d, J=8.04, 1H), 3.80 (s, 2H).

Example 28

2-Methyl-2-(1-(naphthalen-1-yl)-1H-1,2,3-triazol-5-ylthio)propanoic acid

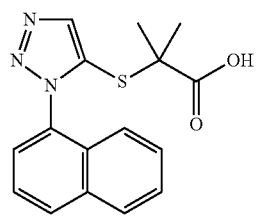 [SMILES: CC(C)(Sc1cnnn1-c1cccc2ccccc12)C(=O)O]

2-Methyl-2-(1-(naphthalen-1-yl)-1H-1,2,3-triazol-5-ylthio)propanoic acid was prepared according to the same procedures described in example 27, using 2-bromo-2-methylpropanoic acid in place of 2-bromoacetic acid.

$^1$H NMR (DMSO-$d_6$, 400 MHz): δ 13.1 (s, 1H), 8.26 (d, J=8.1 Hz, 1H), 8.2 (s, 1H), 8.16 (d, J=8.1 Hz, 1H), 7.78 (m, 2H), 7.68 (m, 1H), 7.62 (m, 1H), 7.03 (d, J=8.04, 1H), 1.27 (s, 6H)

Example 29

2-(1-(naphthalen-1-yl)-1H-tetrazol-5-ylthio)acetic acid

Step A: 1-(Naphthalen-1-yl)-1H-tetrazole-5-thiol

To a solution of 1-naphthalenylisothiocyanate (500 mg, 2.7 mmol) in ethanol (150 mL) was added sodium azide (2.8 g, 43 mmol) and the mixture was heated to 79° C. for 2 hours. The reaction mixture was then cooled to room temperature, aqueous HCl solution (12N, 1.5 mL) added and the mixture concentrated. The resulting residue was diluted with ethyl acetate and extracted with aqueous NaOH solution (1N) and the aqueous layer acidified with aqueous HCl solution (12N) until a precipitate formed. The precipitate was collected and used in the next step without further purification (520 mg, 85% yield).

Step B: Ethyl 2-(1-(naphthalen-1-yl)-1H-tetrazol-5-ylthio)acetate

A mixture of 1-(Naphthalen-1-yl)-1H-tetrazole-5-thiol (235 mg, 1.03 mmol), ethyl bromoacetate (189 mg, 1.13 mmol) and potassium carbonate (171 mg, 1.24 mmol) in DMF (3 mL) was stirred at room temperature for 16 hours. Water was then added to the reaction mixture and the precipitate that formed collected to give ethyl 2-(1-(naphthalen-1-yl)-1H-tetrazol-5-ylthio)acetate as a solid (306 mg, 94%).

Step C: 2-(1-(Naphthalen-1-yl)-1H-tetrazol-5-ylthio)acetic acid

A mixture of ethyl 2-(1-(naphthalen-1-yl)-1H-tetrazol-5-ylthio)acetate (269 mg, 0.86 mmol), aqueous sodium hydroxide solution (10%, 5 mL) and methanol (10 mL) was stirred at reflux for 2 hours. The reaction was then cooled to room temperature and the methanol removed. Water was added, neutralized with aqueous HCl solution (1N) and extracted with ethyl acetate. The organic layer was dried over sodium sulfate and concentrated. Purification by preparative thin layer chromatography (95% dichloromethane/5% methanol) afforded compound 2-(1-(naphthalen-1-yl)-1H-tetrazol-5-ylthio)acetic acid as a solid.

$^1$H NMR (DMSO-$d_6$, 400 MHz): δ 13.1 (s, 1H), 8.4 (d, J=8.1 Hz, 1H), 8.2 (d, J=8.1 Hz, 1H), 7.9 (m, 4H), 7.5 (d, J=8.3 Hz, 1H), 4.3 (s, 2H).

Example 30

2-Methyl-2-(1-(naphthalen-1-yl)-1H-tetrazol-5-ylthio)propanoic acid

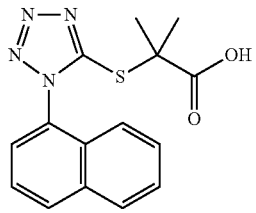

2-Methyl-2-(1-(naphthalen-1-yl)-1H-tetrazol-5-ylthio) propanoic acid was prepared according to the same procedures described in example 29, using 2-bromo-2-methylpropanoic acid in place of 2-bromoacetic acid.

$^1$H NMR (DMSO-$d_6$, 400 MHz): δ 13.1 (s, 1H), 8.4 (d, J=8.04 Hz, 1H), 8.2 (d, J=8.04 Hz, 1H), 7.9 (m, 4H), 7.1 (d, J=8.3 Hz, 1H), 1.7 (s, 6H).

Example 31

2-Methyl-2-(1-(naphthalen-1-yl)-1H-tetrazol-5-ylthio)propanoic acid

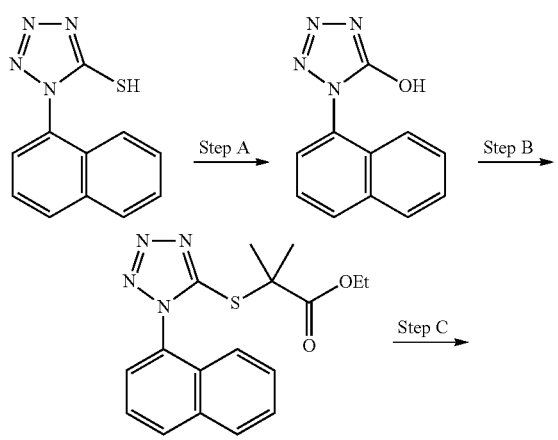

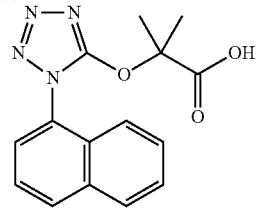

Step A: 1-(Naphthalen-1-yl)-1H-tetrazol-5-ol

To a mixture of sodium hydroxide (114 mg, 2.9 mmol) in water (0.5 mL) was added 1-(naphthalen-1-yl)-1H-tetrazole-5-thiol (490 mg, 2.2 mmol) and ethanol (5 mL). The reaction mixture was then cooled to 0° C., propylene oxide (168 mg, 2.9 mmol) added dropwise and the mixture stirred at 0° C. for 30 minutes and then room temperature for 5 hours. The mixture was taken up and washed with ethyl acetate. The aqueous layer was acidified with aqueous HCl solution (1N) and extracted with ethyl acetate. The organic layer was dried over sodium sulfate and concentrated to give pure 1-(naphthalen-1-yl)-1H-tetrazol-5-ol (420 mg, 90%).

Step B: Ethyl 2-methyl-2-(1-(naphthalen-1-yl)-1H-tetrazol-5-yloxy) propanoate

A mixture of 1-(naphthalen-1-yl)-1H-tetrazol-5-ol (200 mg, 0.54 mmol), ethyl bromoisobutyrate (0.16 mL, 1.04 mmol) and potassium carbonate (160 mg, 1.12 mmol) in DMF (3 mL) was stirred at room temperature for 16 hours. Water was added and the mixture extracted with ethyl acetate, dried over sodium sulfate and concentrated. Purification by preparative thin layer chromatography (95% dichloromethane/5% methanol) afforded ethyl 2-methyl-2-(1-(naphthalen-1-yl)-1H-tetrazol-5-yloxy) propanoate.

Step C: 2-Methyl-2-(1-(naphthalen-1-yl)-1H-tetrazol-5-ylthio)propanoic acid

A mixture of ethyl 2-methyl-2-(1-(naphthalen-1-yl)-1H-tetrazol-5-yloxy) propanoate (39 mg, 0.12 mmol), aqueous sodium hydroxide solution (10%, 5 mL) and methanol (5 mL) was stirred at reflux for 2 hours. The reaction was then cooled to room temperature and the methanol removed. Water was added, neutralized with aqueous HCl solution (1N) and extracted with ethyl acetate. The organic layer was dried over sodium sulfate and concentrated. Purification by preparative thin layer chromatography (95% dichloromethane/5% methanol) afforded 2-methyl-2-(1-(naphthalen-1-yl)-1H-tetrazol-5-ylthio)propanoic acid as a solid (19 mg, 55%).

$^1$H NMR (DMSO-$d_6$, 400 MHz): δ 13.0 (s, 1H), 8.24 (d, J=7.8 Hz, 1H), 8.14 (d, J=8.1 Hz, 1H), 7.8 (m, 5H), 7.1 (d, J=8.3 Hz, 1H), 1.89 (s, 6H).

Example 32

2-(4-(Naphthalen-1-yl)-1,2,3-thiadiazol-5-ylthio)acetic acid

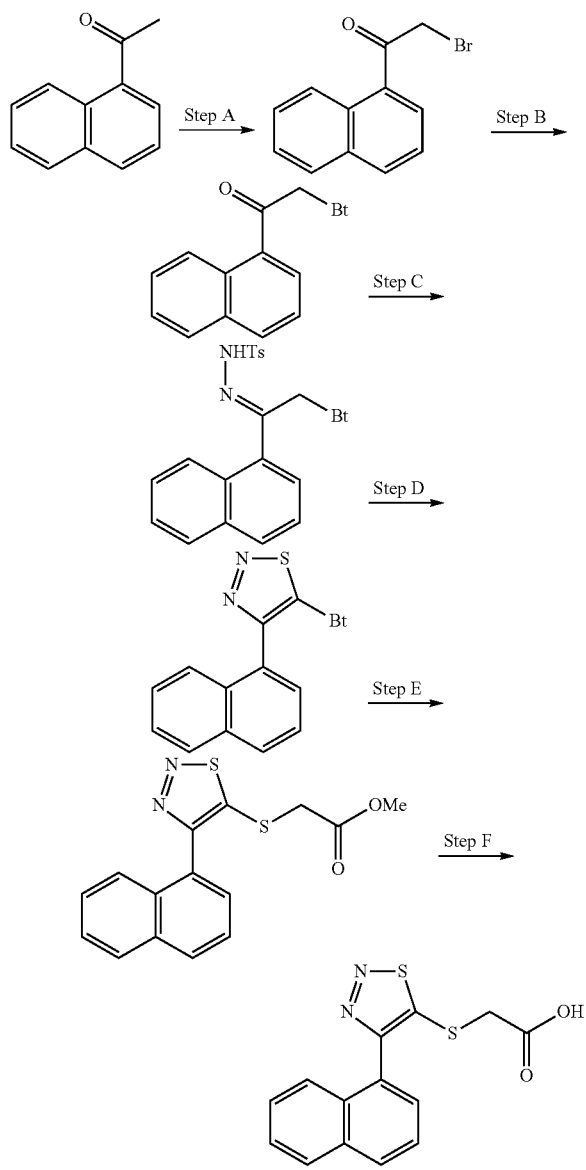

Step A: 2-bromo-1-(naphthalen-1-yl)ethanone

To a solution of 1-(naphthalen-1-yl)ethanone (500 mg, 2.9 mmol) in dioxane (5 mL) was added to a solution of bromine (510 mg, 3.19 mmol) in dioxane (10 mL), at room temperature, over a period of 30 minutes. The reaction mixture was then stirred at room temperature for 20 minutes and concentrated. The resulting residue was diluted with ether and washed with saturated sodium bicarbonate, water, dried over sodium sulfate and concentrated. Purification by preparative thin layer chromatography (70% DCM/30% hexanes) afforded 2-bromo-1-(naphthalen-1-yl)ethanone (673 mg, 93%).

Step B: 2-(1H-benzo[d][1,2,3]triazol-1-yl)-1-(naphthalen-1-yl)ethanone

A mixture of 2-bromo-1-(naphthalen-1-yl)ethanone (1 g, 4.02 mmol), benzotriazole (530 mg, 4.42 mmol) and K2CO3 (560 mg, 4.02 mmol) in toluene (100 mL) was heated at reflux for 16 hours. The reaction was cooled to room temperature, washed with water, dried over sodium sulfate and concentrated. Purification by preparative thin layer chromatography (100% DCM) afforded 2-(1H-benzo[d][1,2,3]triazol-1-yl)-1-(naphthalen-1-yl)ethanone as a tan solid.

Step C: (Z)—N'-(2-(1H-benzo[d][1,2,3]triazol-1-yl)-1-(naphthalen-1-yl)ethylidene)-4-methylbenzene sulfonohydrazide A solution of 2-(1H-benzo[d][1,2,3]triazol-1-yl)-1-(naphthalen-1-yl)ethanone (770 mg, 2.68 mmol) and p-toluenesulfonyl huydrazide (500 mg, 2.68 mmol) in toluene (25 mL) was stirred at reflux for 2 days. The reaction mixture was cooled to room temperature and concentrated to a give (Z)—N'-(2-(1H-benzo[d][1,2,3]triazol-1-yl)-1-(naphthalen-1-yl)ethylidene)-4-methylbenzenesulfonohydrazide as a tan solid that was used in the next step without further purification.

Step D: 5-(1H-benzo[d][1,2,3]triazol-1-yl)-4-(naphthalen-1-yl)-1,2,3-thiadiazole A mixture of (Z)—N'-(2-(1H-benzo[d][1,2,3]triazol-1-yl)-1-(naphthalen-1-yl)ethylidene)-4-methylbenzenesulfonohydrazide (1 g, 2.19 mmol) and SOCl2 (25 mL) was stirred at 60° C. for 18 h and then concentrated and purified by TLC (100% DCM) to afford 5-(1H-benzo[d][1,2,3]triazol-1-yl)-4-(naphthalen-1-yl)-1,2,3-thiadiazole as an amber solid.

Step E: Methyl 2-(4-(naphthalen-1-yl)-1,2,3-thiadiazol-5-ylthio)acetate

NaOH (60% oil, 30 mg, 0.61 mmol) was added to a solution of 5-(1H-benzo[d][1,2,3]triazol-1-yl)-4-(naphthalen-1-yl)-1,2,3-thiadiazole and methylthioglycolate (64 mg, 0.61 mmol) in DMF (3 mL) and the mixture was stirred at room temperature for 2 h. 1N HCl was then added and the mixture was extracted with ethyl acetate, dried over Na2SO4 and concentrated. Purification by TLC (100% DCM) afforded methyl 2-(4-(naphthalen-1-yl)-1,2,3-thiadiazol-5-ylthio)acetate.

Step F: 2-(4-(Naphthalen-1-yl)-1,2,3-thiadiazol-5-ylthio)acetic acid

A mixture of methyl 2-(4-(naphthalen-1-yl)-1,2,3-thiadiazol-5-ylthio)acetate (60 mg, 0.19 mmol), sodium hydroxide (10% aq. 5 mL) and methanol (5 mL) was stirred at reflux for 2 hours. The reaction was then cooled to room and the methanol removed. Water was added, neutralized with 1N HCl and extracted with ethyl acetate. The organic layer was dried over sodium sulfate and concentrated. Purification by preparative thin layer chromatography (95% DCM/5% MeOH) afforded 2-(4-(Naphthalen-1-yl)-1,2,3-thiadiazol-5-ylthio)acetic acid as a solid.

1H NMR (DMSO-d6, 400 MHz): δ 13.3 (s, 1H), 8.19 (d, J=8.2 Hz, 1H), 8.13 (d, J=8.2 Hz, 1H), 7.70 (m, 4H), 4.12 (s, 2H).

II In Vitro Testing

Example 33

Uric Acid Uptake Assay (URAT-1 $EC_{50}$)

Creation of Stable Cell Lines Expressing hURAT1 Transporter: Full-length human URAT1 gene (SLC22A12) was subcloned from plasmid pCMV6-XL5 (Origene) into eukaryotic expression plasmid pCMV6/Neo (Origene) using Not I restriction sites. Gene sequencing confirmed the sequence of hURAT1 as outlined in Genbank (Accession #NM_144585.2). HEK293 human embryonic kidney cells (ATCC#CRL-1573) were propagated in EMEM tissue culture medium as described by ATCC in an atmosphere of 5% $CO_2$ and 95% air. Transfections of HEK293 cells with the pCMV6/Neo/URAT1 construct were performed using L2000 transfection reagent (Invitrogen) as described by the manufacturer. After 24 h the transfected cells were split into 10 cm tissue culture plates and grown for 1 day after which the medium was replaced with fresh growth medium containing G418 (Gibco) at 0.5 mg/ml final concentration. Drug-resistant colonies were selected after approximately 8 days and then tested for $^{14}C$-uric acid transport activity. The HEK293/urat1 cells are plated on Poly-D-Lysine Coated 96-well Plates at a density of 75,000 cells per well.

Cells were grown overnight (20-26 hours) at 37° C. in an incubator. Plates were allowed to come to room temperature and media was washed out with one wash of 250 μl of Wash Buffer (125 mM Na Gluconate, 10 mM Hepes pH 7.3). Compound or vehicle is added in assay buffer with C14 Uric Acid for a final concentration of 40 μM Uric Acid with a specific activity of 54 mCi/mmol Assay Buffer is 125 mM Sodium Gluconate, 4.8 mM Potassium Gluconate, 1.2 mM Potassium phosphate, monobasic, 1.2 mM magnesium sulfate, 1.3 mM Ca Gluconate, 5.6 mM Glucose, 25 mM HEPES, pH 7.3. Plates were incubated at room temperature for 10 minutes then washed 3 times with 50 μl Wash Buffer and 3 times with 250 μl Wash Buffer. Microscint 20 Scintillation Fluid was added and plates were incubated overnight at 45° C. to equilibrate. Plates are then read on the TopCount Plate Reader and an $EC_{50}$ value generated. (See Enomoto et al, *Nature*, 2002, 417, 447-451 and Anzai et al, *J. Biol. Chem.*, 2004, 279, 45942-45950.)

Example 34

URAT-1 Activity of Select Compounds (Uric Acid Uptake Assay)

Compounds prepared as described above in examples 24-32, were examined according to the procedure described herein and $EC_{50}$ values generated. The table below summarizes the activity of the compounds in the Uric Acid Uptake Assay, wherein A represents an $EC_{50} < 5$ μM;

B represents an $EC_{50}$ from 5 μM to 20 μM; and

C represents an $EC_{50} > 20$ μM.

| Eg | Structure | $EC_{50}$ (μM) (URAT-1) |
|---|---|---|
| 24 | 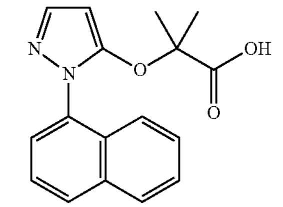 [SMILES: CC(C)(Oc1ccnn1-c1cccc2ccccc12)C(=O)O] | B |
| 25 | 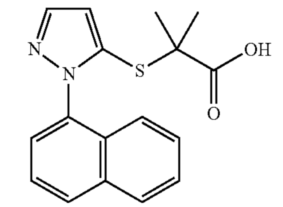 [SMILES: CC(C)(Sc1ccnn1-c1cccc2ccccc12)C(=O)O] | A |
| 26 (step C) | 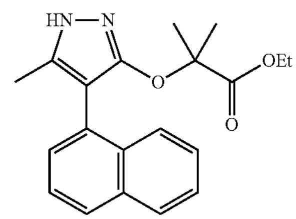 [SMILES: CCOC(=O)C(C)(C)Oc1n[nH]c(C)c1-c1cccc2ccccc12] | A |
| 26 (step D) | 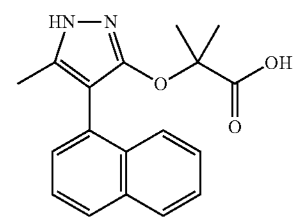 [SMILES: Cc1[nH]nc(OC(C)(C)C(=O)O)c1-c1cccc2ccccc12] | A |
| 27 | 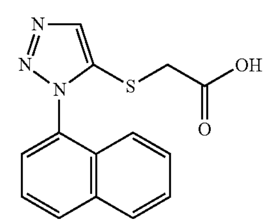 [SMILES: O=C(O)CSc1cnnn1-c1cccc2ccccc12] | C |
| 28 | 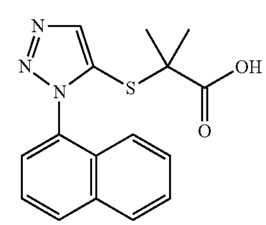 [SMILES: CC(C)(Sc1cnnn1-c1cccc2ccccc12)C(=O)O] | A |
| 29 (step C) | 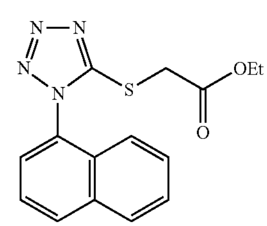 [SMILES: CCOC(=O)CSc1nnnn1-c1cccc2ccccc12] | B |

-continued

| Eg | Structure | EC$_{50}$ (μM) (URAT-1) |
|---|---|---|
| 29 (step D) | 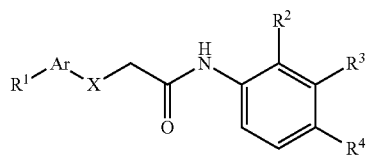 | C |
| 30 | 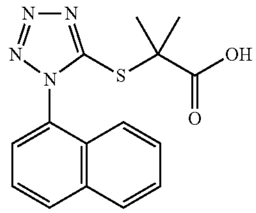 [SMILES: CC(C)(Sc1nnnn1-c1cccc2ccccc12)C(=O)O] | A |
| 31 | 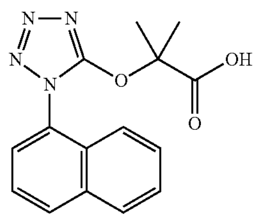 [SMILES: CC(C)(Oc1nnnn1-c1cccc2ccccc12)C(=O)O] | C |
| 32 | 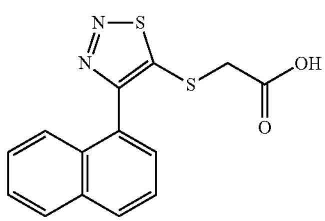 [SMILES: O=C(O)CSc1snnc1-c1cccc2ccccc12] | B |

What is claimed is:

1. A method for decreasing uric acid levels in one or more tissues or organs of a subject, comprising administering to the subject a uric acid level decreasing amount of a compound of Formula (I):

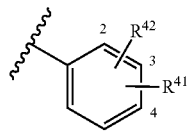

wherein

Ar is a 5-membered aromatic heterocycle containing 1 to 4 heteroatoms each independently selected from N, O and S; said heterocycle being optionally substituted at a substitutable position with R$^{Ar}$, wherein R$^{Ar}$ is H, (C$_{1-4}$)alkyl, CF$_3$ or (C$_{3-7}$)cycloalkyl and wherein the groups X and R$^1$ are attached to positions on the Ar ring which are immediately adjacent to each other;

X is selected from O and S;

R$^1$ is a group of formula:

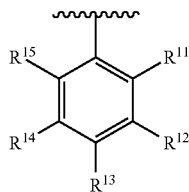

wherein
R$^{11}$ is halo; and
R$^{12}$, R$^{13}$, R$^{14}$ and R$^{15}$ are each independently selected from H, halo, (C$_{1-4}$)alkyl, CF$_3$, (C$_{3-7}$)cycloalkyl, (C$_{3-7}$)cycloalkyl-(C$_{1-4}$)alkyl-, cyano, —O—(C$_{1-4}$) alkyl, —OCF$_3$ and —N((C$_{1-4}$)alkyl)$_2$, wherein said (C$_{3-7}$)cycloalkyl is optionally substituted with (C$_{1-4}$) alkyl; or
R$^{12}$ and R$^{13}$, R$^{13}$ and R$^{14}$, or R$^{14}$ and R$^{15}$ are linked, together with the carbon atoms to which they are attached, to form a five- or six-membered saturated, unsaturated or aromatic ring which optionally contains from one to three heteroatoms each independently selected from O, S and N, wherein the remaining of R$^{12}$, R$^{13}$, R$^{14}$ and R$^{15}$ are defined as hereinbefore;
R$^2$ is selected from halo, nitro and (C$_{1-4}$)alkyl;
R$^3$ is selected from H and halo;
R$^4$ is selected from:
a)

wherein
R$^{42}$ is bonded to position 2 or position 3 of the phenyl ring and is selected from H, halo and (C$_{1-4}$)alkyl; and R$^{41}$ is bonded to position 3 or position 4 of the phenyl ring and is selected from:
i) (C$_{1-4}$)alkyl substituted with —COOH, —COO(C$_{1-4}$) alkyl, —C(O)NH$_2$, —C(=O)NHSO$_2$—(C$_{1-4}$)alkyl, or —OH;
ii) (C$_{2-4}$)alkenyl substituted with —COOH or —COO (C$_{1-4}$)alkyl;
iii) —O—(C$_{1-4}$)alkyl optionally substituted with —COOH, Het, or —N((C$_{1-6}$)alkyl)$_2$, wherein said Het is optionally substituted with —OH or —COOH and wherein either or both of the (C$_{1-6}$)alkyl groups in said —N((C$_{1-6}$)alkyl)$_2$ are optionally substituted with —COOH or —COO(C$_{1-4}$)alkyl; and
iv) —OH, —COOH, —COO(C$_{1-4}$)alkyl, —SO$_2$NH$_2$, or —SO$_2$—(C$_{1-4}$)alkyl;
provided that R$^{42}$ and R$^{41}$ are not both bonded to position 3 of the phenyl ring at the same time;
b) (C$_{2-4}$)alkenyl substituted with —COOH or —COO(C$_{1-4}$)alkyl;
c) Het optionally substituted with (C$_{1-6}$)alkyl, —NH$_2$, —COOH, or (C$_{2-4}$)alkenyl substituted with —COOH;
d) —SO$_2$N(R$^{43}$)R$^{44}$, wherein
R$^{43}$ is H or (C$_{1-6}$)alkyl and $R^{44}$ is selected from $(C_{1-6})$alkyl, phenyl, phenyl-$(C_{1-4})$alkyl-, —C(=O)NH$(C_{1-4})$alkyl, —C(=O)O$(C_{1-4})$alkyl, and Het; wherein said $(C_{1-6})$alkyl is optionally substituted with —OH or —COOH and wherein said Het is optionally substituted with $(C_{1-6})$alkyl; or $R^{43}$ and $R^{44}$, together with the N to which they are attached, are linked together to form a 5- or 6-membered heterocycle which is saturated or unsaturated and which is optionally contain from one to three further heteroatoms each independently selected from N, O and S; said heterocycle being optionally substituted with $(C_{1-6})$alkyl or —COOH;

e) —O—$(C_{1-4})$alkyl substituted with —OH, —COOH or Het, wherein said Het is optionally substituted with —COOH or —COO$(C_{1-6})$alkyl;

provided that the carbon atom of —O—$(C_{1-4})$alkyl which is directly bonded to 0 is not also directly bonded to —OH;

f) —C(=O)N($R^5$)$R^6$ or —O—CH$_2$—C(=O)N($R^5$)$R^6$ wherein $R^5$ is H or $(C_{1-6})$alkyl and $R^6$ is selected from:

i) phenyl optionally substituted with one or two substituents each independently selected from —OH, —COOH, —N(($C_{1-4}$)alkyO$_2$, $(C_{1-4})$alkyl, $(C_{2-4})$alkenyl and Het; wherein said $(C_{1-4})$alkyl is optionally substituted with —COOH and said $(C_{2-4})$alkenyl is substituted with —COOH;

ii) $(C_{1-4})$alkyl optionally substituted with one or two substituents each independently selected from —COOH, —OH, —S—$(C_{1-6})$alkyl and Het;

provided that the carbon atom of $(C_{1-4})$alkyl which is directly bonded to N is not also directly bonded to —OH;

iii) phenyl-$(C_{1-4})$alkyl- wherein the phenyl portion of said phenyl-$(C_{1-4})$alkyl- is optionally substituted with one or two substituents each independently selected from —OH, —NH$_2$, and —COOH;

iv) $(C_{3-7})$cycloalkyl-$(C_{1-4})$alkyl- wherein the cycloalkyl portion of said $(C_{3-7})$cycloalkyl-$(C_{1-4})$alkyl- is optionally substituted with —COOH;

v) Het optionally substituted with one or two substituents each independently selected from $(C_{1-6})$alkyl, phenyl-$(C_{1-4})$alkyl- and —COOH;

vi) $(C_{3-7})$cycloalkyl; and vii) —SO$_2$—$R^{61}$ wherein $R^{61}$ is $(C_{1-4})$alkyl or phenyl;

or $R^5$ and $R^6$, together with the N to which they are attached, are linked together to form a 5- or 6-membered heterocycle which is saturated or unsaturated and which is optionally contain from one to three further heteroatoms each independently selected from N, O and S; said heterocycle being optionally substituted with one or two substituents each independently selected from $(C_{1-6})$alkyl, —COOH and —COO$(C_{1-6})$alkyl;

g) —NHC(=O)—$R^7$ wherein $R^7$ is selected from:

i) $(C_{1-6})$alkyl optionally substituted with one or two substituents each independently selected from —COOH, —O—$(C_{1-4})$alkyl, —NHC(=O)—$(C_{1-4})$alkyl, phenyl and Het; wherein said phenyl is optionally substituted with one or two substituents each independently selected from halo, —OH, —O—$(C_{1-4})$alkyl, —NO$_2$, —COOH, —NH$_2$, —NH$(C_{1-4})$alkyl, —N(($C_{1-4}$)alkyl)$_2$, and $(C_{1-6})$alkyl optionally substituted with from one to three halo substituents;

ii) phenyl optionally substituted with —OH, halo or —COOH;

iii) —NHR$^{71}$ wherein $R^{71}$ is phenyl or phenyl-$(C_{1-4})$alkyl-, wherein said phenyl is optionally substituted with —COOH or —COO$(C_{1-4})$alkyl; and iv) $(C_{1-6})$alkynyl, $(C_{3-7})$cycloalkyl or $(C_{3-7})$cycloalkyl-$(C_{1-4})$alkyl-;

h) —NHSO$_2$$R^8$ wherein $R^8$ is selected from phenyl, phenyl-$(C_{1-4})$alkyl- and Het; and i) —C≡C-$R^9$ wherein $R^9$ is selected from:

i) H, —COOH, —COO$(C_{1-4})$alkyl, phenyl or $(C_{2-4})$alkenyl;

ii) $(C_{3-7})$cycloalkyl optionally substituted with —OH, —COOH, —COO$(C_{1-6})$alkyl, or $(C_{1-4})$alkyl wherein said $(C_{1-4})$alkyl is optionally substituted with —OH or —N($R^{91}$)$R^{92}$, wherein $R^{91}$ is H and $R^{92}$ is $(C_{1-4})$alkyl substituted with Het; or $R^{91}$ and $R^{92}$, together with the N to which they are attached, are linked together to form a 5- or 6-membered heterocycle which is saturated, unsaturated or aromatic and which is optionally contain from one to three further heteroatoms each independently selected from N, O and S; said heterocycle being optionally substituted with one or two substituents each independently selected from $(C_{1-6})$alkyl and —OH; and iii) $(C_{1-6})$alkyl optionally substituted with one, two or three substituents each independently selected from:

a) —OH, —O(C=O)NH$_2$, —O(C=O)NH$(C_{1-4})$alkyl, CF$_3$, —COOH or —COO—$(C_{1-4})$alkyl;

b) Het optionally substituted with $(C_{1-6})$alkyl or —OH;

c) —N($R^{93}$)$R^{94}$ wherein $R^{93}$ is H or $(C_{1-4})$alkyl and $R^{94}$ is selected from H, —$(C_{1-4})$alkyl optionally substituted with $R^{941}$, —SO$_2$—$(C_{1-4})$alkyl and —C(=O)—$R^{942}$;

wherein $R^{941}$ is —COOH, —C(=O)NH$_2$, $(C_{3-7})$cycloalkyl, Het, or phenyl optionally substituted with —OH, and $R^{942}$ is —O—$(C_{1-4})$alkyl, phenyl, $(C_{3-7})$cycloalkyl or Het, wherein said $(C_{3-7})$cycloalkyl is optionally substituted with —COOH and wherein said Het is optionally substituted with one or two substituents each independently selected from $(C_{1-6})$alkyl and —OH; or $R^{942}$ is $(C_{1-4})$alkyl optionally substituted with —COOH, —NH$_2$, —NH$(C_{1-4})$alkyl, —NH-Het, —N(($C_{1-4}$)alkyl)$_2$, or Het; wherein said Het is optionally substituted with one or two substituents each independently selected from —OH, —COOH and $(C_{1-6})$alkyl optionally substituted with Het and wherein the $(C_{1-4})$alkyl portion of said —NH$(C_{1-4})$alkyl is optionally substituted with Het;

d) —C(=O)N($R^{95}$)$R^{96}$, wherein $R^{95}$ is H and $R^{96}$ is selected from $(C_{3-7})$cycloalkyl, —SO$_2$—$R^{961}$ and —$(C_{1-4})$alkyl-$R^{962}$, wherein $R^{961}$ is $(C_{1-4})$alkyl, phenyl, $(C_{3-7})$cycloalkyl, or —N(($C_{1-4}$)alkyl)$_2$; and $R^{962}$ is phenyl, —COOH, —N(($C_{1-4}$)alkyl)$_2$, or Het, wherein said phenyl is optionally substituted with —N(($C_{1-4}$)alkyl)$_2$ and said Het is optionally substituted with oxo; or $R^{95}$ and $R^{96}$, together with the N to which they are attached, are linked together to form a 5- or 6-membered heterocycle which is saturated or unsaturated and which is optionally contain from one to three further heteroatoms each independently selected from N, O and S; said heterocycle being optionally substituted with —COOH; and e) —O($C_{1-4}$)alkyl optionally substituted with $R^{97}$ wherein $R^{97}$ is selected from —OH, —COOH, —C(=O)O—(C-4)alkyl-NH($C_{1-4}$)alkyl, —C(=O)N($R^{971}$)$R^{972}$, —NH$_2$, —NH—($C_{3-7}$)cycloalkyl, —O-Het, and Het;

provided that the carbon atom of —O—($C_{1-4}$)alkyl- which is directly bonded to O is not also directly bonded to —OH, —NH$_2$ or —NH—($C_{3-7}$)cycloalkyl;

wherein each of said Het and the Het portion of said —O-Het is optionally substituted with one or two substituents each independently selected from halo, oxo, ($C_{1-4}$)alkyl, and —OH;

and wherein $R^{971}$ is H or ($C_{1-4}$)alkyl and $R^{972}$ is selected from H, —OH, —NHC(=OD)-($C_{1-4}$)alkyl, —NHC(=O)—NH$_2$, ($C_{1-4}$)alkyl, ($C_{3-7}$)cycloalkyl, phenyl and Het, wherein said ($C_{1-4}$)alkyl is optionally substituted with —OH, —COOH, —N(($C_{1-4}$)alkyl)$_2$ or Het, provided that when $R^{972}$ is ($C_{1-4}$)alkyl, the carbon atom of ($C_{1-4}$)alkyl which is directly bonded to N is not also directly bonded to —OH;

and wherein said ($C_{3-7}$)cycloalkyl is optionally substituted with —COOH, and wherein said phenyl is optionally substituted with —OH, —COOH, or —($C_{2-4}$)alkenyl-COOH;

or $R^{971}$ and $R^{972}$, together with the N to which they are attached, are linked together to form a 5- or 6-membered heterocycle which is saturated or unsaturated and which is optionally contain from one to three further heteroatoms each independently selected from N, O and S; said heterocycle being optionally substituted with ($C_{1-4}$)alkyl or —COOH;

wherein Het is a 4,5- or 6-membered heterocycle or a 9- or 10-membered heterobicycle, each of which is saturated, unsaturated or aromatic and each of which containing from one to four heteroatoms each independently selected from N, O and S, wherein each said N heteroatom is, independently and where possible, exist in an oxidized state such that it is further bonded to an O atom to form an N-oxide group and wherein each said S heteroatom is, independently and where possible, exist in an oxidized state such that it is further bonded to one or two oxygen atoms to form the groups SO or SO$_2$;

or a metabolite, pharmaceutically acceptable salt, solvate, polymorph, ester, tautomer or prodrug thereof.

2. A method for decreasing uric acid levels in one or more tissues or organs of a subject, comprising administering to the subject a uric acid level decreasing amount of a compound of Formula (II):

$$Ar^1—X'—W—Ar^2 \quad (II);$$

wherein
$Ar^1$ is
(i) 5- or 6-membered aromatic heterocycle containing 1 to 4 heteroatoms selected from N, O or S; said heterocycle optionally substituted with ($C_{1-4}$)alkyl, ($C_{3-7}$)cycloalkyl, ($C_{3-7}$)cycloalkyl-($C_{1-3}$)alkyl-, wherein said alkyl, cycloalkyl or cycloalkylalkyl is monosubstituted with —OH; and/or phenyl when the heterocycle contains 1 to 3 N-atoms; in either instance, the said heterocycle is optionally substituted with: phenyl, phenylmethyl, 5- or 6-membered aromatic heterocycle, fused phenyl-unsaturated or saturated 5- or 6-membered carbocycle, fused phenyl-{unsaturated or saturated 5- or 6-membered carbocycle}methyl, or fused phenyl-5- or 6-membered aromatic heterocycle; each of said phenyl, phenylmethyl, aromatic heterocycle, fused phenyl-carbocycle, fused phenyl-(carbocycle)methyl or fused phenyl-aromatic heterocycle in turn is substituted optionally with 1 to 3 substituents selected independently from:

($C_{1-6}$)alkyl, ($C_{3-4}$cycloalkyl, ($C_{3-7}$)cycloalkyl-($C_{1-3}$)alkyl, ($C_{2-6}$)alkenyl, O—($C_{1-4}$)alkyl, S—($C_{1-4}$)alkyl, halo, CF$_3$, OCF$_3$, OH, NO$_2$, CN, phenyl optionally substituted with $C_{1-6}$alkyl or nitro, phenylmethyl optionally substituted with $C_{1-6}$alkyl or nitro, SO$_2$NH$_2$, SO$_2$—($C_{1-4}$)alkyl, C(O)NH$_2$, C(O)OR$^1$, NR$^2$R$^3$, morpholino or 1-pyrrolyl, wherein R$^1$ is H or ($C_{1-4}$)alkyl, and wherein R$^2$ and R$^3$ each independently is H or ($C_{1-4}$)alkyl; wherein said substituents are sterically compatible; or (ii) unsaturated or saturated 5- or 6-membered carbocycle substituted with phenyl or naphthyl, said unsaturated or saturated carbocycle, or the phenyl or naphthyl optionally substituted with the same 1 to 3 substituents as defined for the substituents in section (i); or (iii) benzimidazole optionally N-substituted with phenyl or a fused phenyl-carbocycle as defined above;

X' is a valence bond, O, S, SO, SO$_2$, NR$^4$ or CR$^{4A}$R$^{4B}$ wherein R$^4$, R$^{4A}$ and R$^{4B}$ are each independently H or ($C_{1-4}$)alkyl;

and when X' is O, S, SO, SO$_2$ or NR$^4$:

W is a divalent radical selected from:

(a) (CR$^5$R$^{5A}$)$_{1-2}$—C(Z$^A$)NR$^6$ wherein R$^5$ and R$^{5A}$ each independently is H or ($C_{1-4}$)alkyl, R$^6$ is H or ($C_{1-4}$)alkyl, and Z$^A$ is oxo or thioxo;

(b) D-C(Z$^B$) wherein D is ($C_{1-4}$)alkylene, ($C_{1-4}$)alkylene-O or ($C_{1-4}$)alkylene-NR$^7$ wherein R$^7$ is H or ($C_{1-4}$)alkyl, and Z$^B$ is oxo or thioxo;

(c) CH$_2$C(Z$^C$)NR$^{7A}$($C_{1-4}$)alkylene wherein Z$^C$ is oxo or thioxo and R$^{7A}$ is H or ($C_{1-4}$)alkyl;

(d) ($C_{1-4}$)alkylene-NR$^{7B}$C(Z$^D$)NR$^{7C}$ wherein R$^{7B}$ and R$^{7C}$ each independently is H or ($C_{1-4}$)alkyl, and Z$^D$ is oxo or thioxo;

(e) ($C_{1-4}$)alkylene optionally substituted with OH, or optionally disubstituted with OH when the ($C_{1-4}$)alkylene contains 2 to 4 carbon atoms; ($C_{2-4}$)alkenyl optionally substituted with halo;

or cis- or trans-

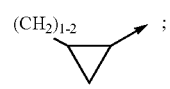

or (f) {($C_{1-4}$)alkylene}-O optionally substituted on the alkylene portion with OH;

(g) {($C_{1-4}$)alkylene}-NR$^8$ optionally substituted on the alkylene portion with OH, and R$^8$ is H or ($C_{1-4}$)alkyl;

(h) (C$_{h}$4)alkylene-C(Z$^E$)($C_{1-4}$)alkylene wherein Z$^E$ is oxo or thioxo; or (i)

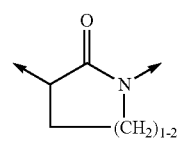

or (j) $(CR^5R^{5A})_{1-2}$—$NR^6$—$(CR^5R^{5A})_{1-2}$ wherein $R^5$ and $R^{5A}$ each independently is H or $(C_{1-4})$alkyl, $R^6$ is H or $(C_{1-4})$alkyl; or when X' is a valence bond:

W is a $\{(C_{2-4}\text{alkenyl}\}C(O)NR^{8A}$, cis- or trans-

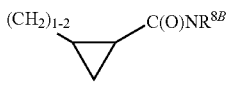

or cis- or trans-

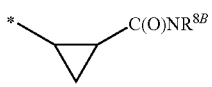

wherein $R^{5A}$ and $R^{5B}$ each is H or $(C_{1-4})$alkyl; or when X' is $CR^{4A}R^{4B}$ as defined above:

W is selected from $\{(C_{1-4})\text{alkylene}\}C(O)NR^{8C}$, S—$\{(C_{1-4})\text{alkylene}\}C(O)NR^{8D}$, O—$\{(C_{1-4})\text{alkylene}\}C(O)NR^{8E}$, or $NR^{8F}$—$\{(C_{1-4})\text{alkylene}\}$-$NR^{8G}$ wherein $R^{8C}$, $R^{8D}$, $R^{8E}$, $R^{8F}$ and $R^{8G}$ each independently is H or $(C_{1-4})$alkyl; and $Ar^2$ is (i) a phenyl or pyridinyl selected from the formulas

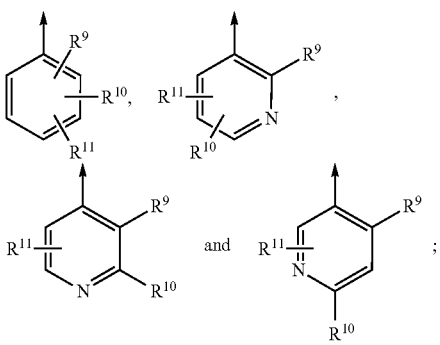

wherein $R^9$, $R^{10}$ and $R^{11}$ each independently represents:

H, $(C_{1-6})$alkyl, $(C_{3-7})$cycloalkyl, $(C_{3-7})$cycloalkyl-$(C_{1-3})$alkyl, $(C_{2-6})$alkenyl, S—$(C_{1-6})$alkyl, halo, $CF_3$, $OCF_3$, OH, $NO_2$, CN, —$NR^{N1}R^{N2}$, —$C(O)R^{21}$, —$(C_{1-3})$alkyl-$C(O)R^{21}$, —$C(O)OR^{22}$, —$(C_{1-3})$alkyl-$C(O)OR^{22}$, —$SO_2$—$(C_{1-3})$alkyl-$C(O)OR^{22}$, wherein $R^{21}$ is $(C_{1-4})$alkyl; $R^{22}$ is H or $(C_{1-4})$allyl; $C(O)NH_2$, —$(C_{1-3})$alkyl-$C(O)NH_2$, $S(O)$—$(C_{1-4})$alkyl, $SO_2$—$(C_{1-4})$alkyl, $SO_2NH_2$, phenyl, phenylmethyl, phenyl-$SO_2$—, 2-, 3- or 4-pyridinyl, 1-pyrrolyl, whereby said phenyl, pyridinyl and pyrrolyl have one or more substituents selected from the group consisting of halo, $NO_2$, $C_{1-3}$-alkyl and $CF_3$;

wherein the substituents $R^9$, $R^{10}$ and $R^{11}$ are sterically compatible;

wherein $R^{N1}$, $R^{N2}$ each independently represent H or $(C_{1-6})$alkyl, whereby $R^{N1}$ and $R^{N2}$ is covalently bonded to each other to form together with the N-atom to which they are attached to a 4 to 7-membered heterocycle whereby the —$CH_2$-group at the position 4 of a 6 or 7-membered heterocycle is replaced by —O—, —S— or —$NR^{N3}$ wherein $R^{N3}$ represents H, —$C(O)OR^{22}$, $(C_{1-6})$alkyl, $(C_{3-7})$cycloalkyl or $(C_{3-7})$cycloalkyl-$(C_{1-3})$alkyl, wherein $R^{22}$ is H or $(C_{1-4})$alkyl; or (ii) $Ar^2$ is a fused phenyl-(saturated or unsaturated 5- or 6-membered carbocyclic ring optionally substituted with 1 to 3 substituents selected independently from $(C_{1-4})$alkyl, O—$(C_{1-4})$alkyl, S—$(C_{1-4})$alkyl, $NO_2$ or halo; or (iii) $Ar^2$ is a 5- or 6-membered aromatic heterocycle containing 1 to 4 heteroatoms selected from N, O or S, or a fused phenyl-5- or 6-membered heterocycle, said aromatic heterocycle or fused phenyl-heterocycle is optionally substituted with 1 to 3 substituents selected independently from $(C_{1-4})$alkyl, O—$(C_{1-4})$alkyl, S—$(C_{1-4})$alkyl, $NO_2$ or halo; or (iv) $Ar^2$ is phthalimido and W is $(C_{1-4})$alkylene;

or a metabolite, pharmaceutically acceptable salt, solvate, polymorph, ester, tautomer or prodrug thereof.

3. The method of claim 2, wherein $Ar^1$ is

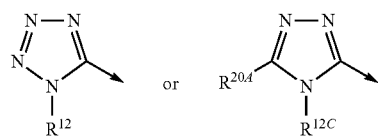

wherein $R^{12}$ is selected from the group consisting of

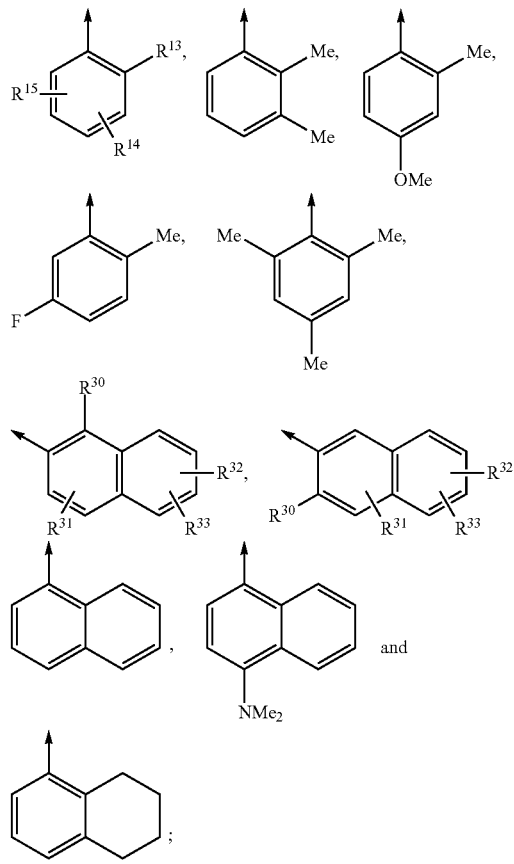

$R^{13}$ represents Cl, Br, COO($C_{1-4}$)alkyl and if $R^9$ is $NO_2$, Cl or Br, then $R^{13}$ also represent F or $CH_3$;

$R^{14}$, $R^{15}$, $R^{31}$, $R^{32}$, $R^{33}$ are each independently selected from the group consisting of H, ($C_{1-6}$)alkyl, ($C_{3-7}$)cycloalkyl, ($C_{3-7}$)cycloalkyl-($C_{1-3}$)alkyl, ($C_{2-6}$)alkenyl, O—($C_{1-4}$)alkyl, S—($C_{1-4}$)alkyl, halo, $CF_3$, $OCF_3$, OH, $NO_2$, CN, $SO_2NH_2$, $SO_2$—($C_{1-4}$)alkyl, C(O)O$R^1$ wherein $R^1$ is H or ($C_{1-4}$)alkyl, or $NR^2R^3$ wherein $R^2$ and $R^3$ each independently is H or ($C_{1-4}$)alkyl;

$R^{30}$ represents H, Cl, Br, COO($C_{1-4}$)alkyl;

$R^{12C}$ is a phenyl of formula

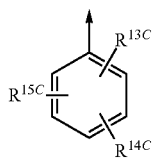

wherein $R^{13C}$, $R^{14C}$ and $R^{15C}$ each independently represents H, ($C_{1-6}$)alkyl, ($C_{3-7}$)cycloalkyl, ($C_{3-7}$)cycloalkyl-($C_{1-3}$)alkyl, ($C_{2-6}$)alkenyl, O—($C_{1-4}$)alkyl, S—($C_{1-4}$)alkyl, halo, $CF_3$, $OCF_3$, OH, $NO_2$, CN, $SO_2NH_2$, $SO_2$—($C_{1-4}$)alkyl, C(O)O$R^1$ wherein $R^1$ is H or ($C_{1-4}$)alkyl, or $NR^2R^3$ wherein $R^2$ and $R^3$ each independently is H or ($C_{1-4}$)alkyl; provided that at least one of $R^{13C}$, $R^{14C}$ and $R^{15C}$ is other than hydrogen;

or $R^{12C}$ is

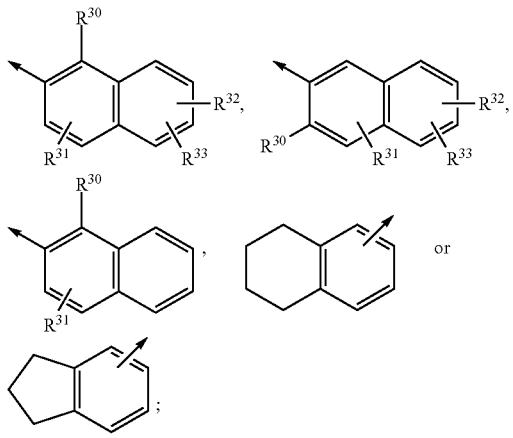

wherein $R^{30}$, $R^{31}$, $R^{32}$, $R^{33}$ are as defined hereinbefore; and $R^{20A}$ is H, ($C_{1-4}$)alkyl, ($C_{3-7}$)cycloalkyl or ($C_{3-7}$)cycloalkyl-($C_{1-3}$)alkyl-, wherein said alkyl, cycloalkyl or cycloalkylalkyl is monosubstituted with —OH; and X is S or O;

W is $CH_2C(O)NR^6$ wherein $R^6$ is H or ($C_{1-4}$)alkyl; and $Ar^2$ is:

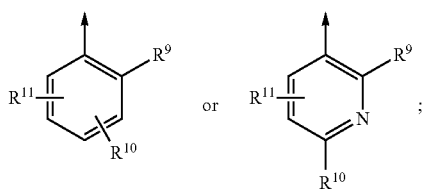

wherein $R^9$ is halo or $NO_2$; and if $R^{13}$ is Cl or Br, then $R^9$ also represents ($C_{1-3}$)alkyl;

$R^{10}$, $R^{11}$ are independently of each other selected from the group consisting of H, ($C_{1-6}$)alkyl, ($C_{3-7}$)Cycloalkyl, ($C_{3-7}$)Cycloalkyl-($C_{1-3}$)alkyl, ($C_{2-6}$)alkenyl, O($C_{1-6}$) alkyl, S($C_{1-6}$)alkyl, halo, $CF_3$, $OCF_3$, OH, $NO_2$, CN, —$NR^{N1}R^{N2}$, —C(O)$R^{21}$, —($C_{1-3}$)alkyl-C(O)$R^{21}$, —C(O)O$R^{22}$, —($C_{1-3}$)alkyl-C(O)O$R^{22}$, —$SO_2$—($C_{1-3}$) alkyl-C(O)O$R^{22}$, wherein $R^{21}$ is ($C_{1-4}$)alkyl and $R^{22}$ is H or ($C_{1-4}$)alkyl; —($C_{1-3}$)alkyl-C(O)$NH_2$, C(O)$NH_2$, S(O)—($C_{1-6}$)alkyl, —$SO_2$—($C_{1-6}$)alkyl, —$SO_2$-phenyl, —$SO_2$—$NH_2$, phenyl, phenylmethyl, 2-, 3- or 4-pyridinyl, 1-pyrrolyl, whereby said phenyl, pyridinyl and pyrrolyl have one or more substituents selected from the group consisting of halo, $NO_2$, $C_{1-3}$-alkyl and $CF_3$.

4. A method for decreasing uric acid levels in one or more tissues or organs of a subject, comprising administering to the subject a uric acid level decreasing amount of a compound of Formula (III):

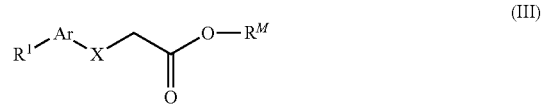

wherein

Ar is a 5-membered aromatic heterocycle containing 1 to 4 heteroatoms each independently selected from N, O and S;

said heterocycle being optionally substituted at a substitutable position with $R^{Ar}$;

wherein $R^{Ar}$ is H, ($C_{1-4}$)alkyl, $CF_3$ or ($C_{3-7}$)cycloalkyl, and wherein the groups X and $R^1$ are attached to positions on the Ar ring which are immediately adjacent to each other;

X is O or S;

$R^M$ is H, a pharmaceutically acceptable cation, substituted or unsubstituted ($C_{1-6}$)alkyl, substituted or unsubstituted aryl, substituted or unsubstituted heteroaryl, or a prodrug moiety;

$R^1$ is a group of formula:

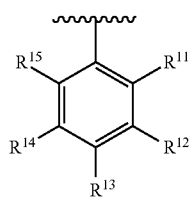

wherein $R^{11}$ is F, Cl, Br or I; and $R^{12}$, $R^{13}$, $R^{14}$ and $R^{15}$ are each independently selected from H, F, Cl, Br, I, CN, $CF_3$, —$OCF_3$, ($C_{1-4}$)alkyl, —O—($C_{1-4}$)alkyl, —N(($C_{1-4}$)alkyl)$_2$, ($C_{3-7}$)cycloalkyl and ($C_{3-7}$)cycloalkyl-($C_{1-4}$)alkyl-;

wherein said ($C_{3-4}$cycloalkyl is optionally substituted with ($C_{1-4}$)alkyl; or $R^{12}$ and $R^{13}$, $R^{13}$ and $R^{14}$, or $R^{14}$ and $R^{15}$ are linked, together with the carbon atoms to which they are attached, to form a five- or six-membered saturated, unsaturated or aromatic ring which optionally contains from one to three heteroatoms each independently selected from O, S and N, wherein the remaining of $R^{12}$, $R^{13}$, $R^{14}$ and $R^{15}$ are defined as hereinbefore;

or a metabolite, pharmaceutically acceptable salt, solvate, polymorph, ester, tautomer or prodrug thereof.

5. A method for decreasing uric acid levels in one or more tissues or organs of a subject, comprising administering to the subject a uric acid level decreasing amount of a compound of Formula (IV):

$$Ar^1—X'—W—C(O)—O—R^M \qquad (IV)$$

wherein $R^M$ is H, a pharmaceutically acceptable cation, substituted or unsubstituted $(C_{1-6})$alkyl, substituted or unsubstituted aryl, substituted or unsubstituted heteroaryl, or a prodrug moiety;

$Ar^1$ is
  (i) 5- or 6-membered aromatic heterocycle containing 1 to 4 heteroatoms selected from N, O or S; said heterocycle optionally substituted with $(C_{1-4})$alkyl, $(C_{3-7})$cycloalkyl, $(C_{3-7})$cycloalkyl-$(C_{1-3})$alkyl-, wherein said alkyl, cycloalkyl or cycloalkylalkyl is monosubstituted with —OH; and/or phenyl when the heterocycle contains 1 to 3 N-atoms; in either instance, the said heterocycle is optionally substituted with:
    phenyl, phenylmethyl, 5- or 6-membered aromatic heterocycle, fused phenyl-unsaturated or saturated 5- or 6-membered carbocycle, fused phenyl-{unsaturated or saturated 5- or 6-membered carbocycle}methyl, or fused phenyl-5- or 6-membered aromatic heterocycle; each of said phenyl, phenylmethyl, aromatic heterocycle, fused phenyl-carbocycle, fused phenyl-(carbocycle)methyl or fused phenyl-aromatic heterocycle in turn is substituted optionally with 1 to 3 substituents selected independently from:
      $(C_{1-6})$alkyl, $(C_{3-7})$cycloalkyl, $(C_{3-7})$cycloalkyl-$(C_{1-3})$alkyl, $(C_{2-6})$alkenyl, O—$(C_{1-4})$alkyl, S—$(C_{1-4})$alkyl, halo, $CF_3$, $OCF_3$, OH, $NO_2$, CN, phenyl optionally substituted with $C_{1-6}$alkyl or nitro, phenylmethyl optionally substituted with $C_{1-6}$alkyl or nitro, $SO_2NH_2$, $SO_2$—$(C_{1-4})$alkyl, $C(O)NH_2$, $C(O)OR^1$, $NR^2R^3$, morpholino or 1-pyaolyl, wherein $R^1$ is H or $(C_{1-4})$alkyl, and wherein $R^2$ and $R^3$ each independently is H or $(C_{1-4})$alkyl; wherein said substituents are sterically compatible; or
  (ii) unsaturated or saturated 5- or 6-membered carbocycle substituted with phenyl or naphthyl, said unsaturated or saturated carbocycle, or the phenyl or naphthyl optionally substituted with the same 1 to 3 substituents as defined for the substituents in section (i); or
  (iii) benzimidazole optionally N-substituted with phenyl or a fused phenyl-carbocycle as defined above;

$X'$ is a valence bond, O, S, SO, $SO_2$, $NR^4$ or $CR^{4A}R^{4B}$, wherein
  $R^4$ is H or $(C_{1-4})$alkyl;
  $R^{4A}$ and $R^{4B}$ are each independently H or $(C_{1-4})$alkyl;

and wherein
when $X'$ is O, S, SO, $SO_2$ or $NR^4$, then W is a divalent radical selected from
  (a) $(CR^5R^{5A})_{1-2}$—$C(Z^A)NR^6$;
    wherein $R^5$ and $R^{5A}$ are each independently H or $(C_{1-4})$alkyl;
    $R^6$ is H or $(C_{1-4})$alkyl, and
    $Z^A$ is oxo or thioxo;
  (b) D-C($Z^B$);
    wherein D is $(C_{1-4})$alkylene, $(C_{1-4})$alkylene-O or $(C_{1-4})$alkylene-$NR^7$;
      wherein $R^7$ is H or $(C_{1-4})$alkyl; and
    $Z^B$ is oxo or thioxo;
  (c) $CH_2C(Z^C)NR^{7A}(C_{1-4})$alkylene;
    wherein $Z^C$ is oxo or thioxo; and
    $R^{7A}$ is H or $(C_{1-4})$alkyl;
  (d) $(C_{1-4})$alkylene-$NR^{7B}C(Z^D)NR^{7C}$;
    wherein $R^{7B}$ and $R^{7C}$ are each independently H or $(C_{1-4})$alkyl; and
    $Z^D$ is oxo or thioxo;
  (e) $(C_{1-4})$alkylene optionally substituted with OH, or optionally disubstituted with OH when the $(C_{1-4})$ alkylene contains 2 to 4 carbon atoms; $(C_{2-4})$alkenyl optionally substituted with halo; or cis- or trans-

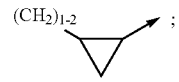

(f) {$(C_{1-4})$alkylene}-O optionally substituted on the alkylene portion with OH;
  (g) {$(C_{1-4})$alkylene}-$NR^8$ optionally substituted on the alkylene portion with OH;
    wherein $R^8$ is H or $(C_{1-4})$alkyl;
  (h) $(C_{1-4})$allylene-$C(Z^E)(C_{1-4})$alkylene;
    wherein $Z^E$ is oxo or thioxo;
  (i)

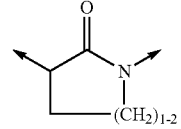

or
  (j) $(CR^5R^{5A})_{1-2}$—$NR^6$—$(CR^5R^{5A})_{1-2}$;
    wherein $R^5$ and $R^{5A}$ are each independently H or $(C_{1-4})$alkyl; and
    $R^6$ is H or $(C_{1-4})$alkyl; or
when $X'$ is a valence bond, then W is
  {$(C_{2-4})$alkenyl}$C(O)NR^{8A}$;
  cis- or trans-

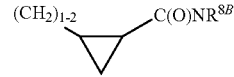

or
cis- or trans-

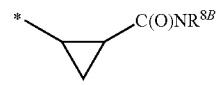

wherein $R^{8A}$ and $R^{8B}$ are each independently H or $(C_{1-4})$ alkyl; or
when X is $CR^{4A}R^{4B}$, then W is
  {$(C_{1-4})$alkylene}$C(O)NR^{8C}$, S—{$(C_{1-4})$alkylene}$C(O)NR^{8D}$, O—{$(C_{1-4})$-alkylene}$C(O)NR^{8E}$, or $NR^{8F}$—{$(C_{1-4})$alkylene}-$NR^{8G}$;

wherein $R^{8C}$, $R^{8D}$, $R^{8E}$, $R^{8F}$ and $R^{8G}$ are each independently H or $(C_{1-4})$alkyl;

or a metabolite, pharmaceutically acceptable salt, solvate, polymorph, ester, tautomer or prodrug thereof.

6. A method for
a) treating hypoxanthine-guanine phosphoribosyltransferase (HPRT) deficiency; or
b) reducing the size of tophi/tophus in a subject; or
c) reducing uric acid production, increasing uric acid excretion or both; or
d) treating hyperuricemia; or
e) treating a subject suffering from a condition characterized by high tissue or organ levels of uric acid in a subject; or
f) treating a condition selected from gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis or sarcoidosis
comprising administering to the subject an effective amount of a compound of Formula (I), Formula (II), Formula (III) or Formula (IV) or a metabolite, pharmaceutically acceptable salt, solvate, polymorph, ester, tautomer or prodrug thereof.

7. The method of claim 6, wherein said condition is gout.

8. The method of claim 6, wherein said condition is joint inflammation.

9. The method of claim 6, further comprising administering an additional agent effective for the treatment of the condition.

10. The method of claim 6, wherein the agent is effective in reducing tissue levels of uric acid.

11. The method of claim 9, wherein the agent is a nonsteroidal anti-inflammatory drugs (NSAIDs), colchicine, a corticosteroid, adrenocorticotropic hormone (ACTH), probenecid, sulfinpyrazone, febuxostat or allopurinol.

12. The method of claim 9, wherein the agent is allopurinol.

13. The method of claim 9, wherein the agent is febuxostat.

14. A pharmaceutical composition comprising:
i) a compound of Formula (I), Formula (II), Formula (III) or Formula (IV) or a metabolite, pharmaceutically acceptable salt, solvate, polymorph, ester, tautomer or prodrug thereof;
ii) allopurinol; and
iii) optionally one or more pharmaceutically acceptable carriers.

15. A pharmaceutical composition comprising:
i) a compound of Formula (I), Formula (II), Formula (III) or Formula (IV) or a metabolite, pharmaceutically acceptable salt, solvate, polymorph, ester, tautomer or prodrug thereof;
ii) febuxostat; and
iii) optionally one or more pharmaceutically acceptable carriers.

* * * * *